(12) United States Patent
Goodall et al.

(10) Patent No.: US 7,172,986 B2
(45) Date of Patent: Feb. 6, 2007

(54) CATALYTIC COMPOSITION AND ITS PREPARATION AND USE FOR PREPARING POLYMERS FROM ETHYLENICALLY UNSATURATED MONOMERS

(75) Inventors: Brian Leslie Goodall, Ambler, PA (US); Jennifer Lynn Petoff, Yardley, PA (US); Han Shen, Lansdale, PA (US)

(73) Assignee: Rohm and Haas Company, Philadelphia, PA (US)

( * ) Notice: Subject to any disclaimer, the term of this patent is extended or adjusted under 35 U.S.C. 154(b) by 0 days.

(21) Appl. No.: 11/139,874

(22) Filed: May 27, 2005

(65) Prior Publication Data

US 2005/0277569 A1    Dec. 15, 2005

Related U.S. Application Data

(60) Provisional application No. 60/579,360, filed on Jun. 14, 2004.

(51) Int. Cl.
| | | |
|---|---|---|
| C07F 1/08 | (2006.01) | |
| C07F 15/00 | (2006.01) | |
| C07F 11/00 | (2006.01) | |
| B01J 31/18 | (2006.01) | |
| C08F 4/70 | (2006.01) | |

(52) U.S. Cl. ............... 502/103; 502/162; 502/167; 526/113; 526/117; 526/171; 526/172; 526/319; 556/28

(58) Field of Classification Search ............... 502/113, 502/162, 167, 103; 526/113, 117, 171, 172, 526/319; 556/35, 37, 110, 136, 137, 138, 556/28
See application file for complete search history.

(56) References Cited

U.S. PATENT DOCUMENTS

| | | |
|---|---|---|
| 3,821,181 A | 6/1974 | Jufa et al. |
| 5,442,020 A | 8/1995 | Davis |
| 5,929,181 A | 7/1999 | Makovetsky et al. |
| 6,037,297 A | 3/2000 | Stibrany et al. |
| 6,242,622 B1 | 6/2001 | Oda et al. |
| 6,265,506 B1 | 7/2001 | Goodall et al. |
| 6,300,440 B1 | 10/2001 | Sen et al. |
| 6,303,724 B1 | 10/2001 | Goodall et al. |
| 6,350,832 B1 | 2/2002 | Bell et al. |
| 6,417,303 B1 | 7/2002 | Stibrany et al. |
| 6,455,650 B1 | 9/2002 | Lipian et al. |
| 6,506,861 B2 | 1/2003 | Wang et al. |
| 6,541,585 B2 | 4/2003 | Johnson et al. |
| 6,544,919 B1 | 4/2003 | Tagge et al. |
| 6,593,440 B2 | 7/2003 | Sen et al. |
| 6,677,419 B1 | 1/2004 | Brock et al. |
| 6,723,486 B2 | 4/2004 | Goodall et al. |
| 2002/0040115 A1 | 4/2002 | Sen et al. |
| 2003/0144441 A1 | 7/2003 | Sen et al. |
| 2003/0171209 A1 | 9/2003 | Wang et al. |
| 2004/0054207 A1 | 3/2004 | Kim et al. |
| 2004/0063885 A1 | 4/2004 | Rhodes et al. |

FOREIGN PATENT DOCUMENTS

| | | |
|---|---|---|
| EP | 0 589 527 B1 | 7/1999 |
| EP | 1 508 577 A | 2/2005 |
| WO | WO 00/06615 A1 | 10/2000 |
| WO | WO 01/92354 A2 | 6/2001 |
| WO | WO 03/102038 A | 12/2003 |

OTHER PUBLICATIONS (XP-002309203) Britovsek, George J. P. et al., "Cationic Methylpalladium(II) Complexes Containing Bidentate N-O and P-O Ligands and a Tridentate P-O-N Ligand: Synthesis, Carbonylation and Catalytic Applications in the Copolymerisation of Carbon Monoxide and Ethene", *Journal of Organometallic Chemistry*, 533, 201-212, (1997).

(XP-002309202) Thomas Rüether et al., "Novel Methylpalladium(II) Complexes Bearing Tridententate Imidazole-Based Chelate Ligands: Synthesis Structural Characterization, and Reactivity", *Organometallics*, 20, 5522-5531 (2001).

(XP-002253038) Pickel, Marco et al., "Facile Preparation and Activation of High Productivity Single-Site Nickel Catalysts for Highly Linear Polyethylene", *Helvetica Chimica Acta, Verlag Helvetica Chimica Acta* 85, 4337-4352, (2002).

Elite Drent et al., "Palladium Catalysed Copolymerization of Ethene with Alkylacrylates: Polar Comonomer Built into the Linear Polymer Chain," *ChemComm*, www.rsc.org/chemcomm, Dec. 10, 2001.

Ilia A. Guzei et al., "Benzenedicarbonyl and Benzenetriacarbonyl Linker Pyrazolyl Complexes of Palladium(II): Synthesis, X-ray Structures and Evaluation as Ethylene Polymerization Catalyst," *Dalton*, www.rsc.org/dalton, Aug. 28, 2002.

Christine Elia et al., "Palladium-Based System for the Polymerization of Acrylates," *Organometallics* 2002, 21, 4229-4256, Jun. 3, 2002.

John Lipian et al., "Addition Polymerization of Norbornene-Type Monomers. High Activity Cationic Allyl Palladium Catalysts," *Macromolecules* 2002, 35, 8969-8977, Sep. 3, 2002.

George M. Benedikt, "Copolymerization of Ethene with Norbornene Derivatives Using Neutral Nickel Catalysts," *Macromolecules* 2002, 35, 8978-8988, Sep. 17, 2002.

Dennis A. Barnes et al., "Addition Polymerization of Norbornene-Type Monomers Using Neutral Nickel Complexes Containing Fluorinated Aryl Ligands," *Macromolecules* 2003, 36, 2623-2632, Feb. 11, 2003.

(Continued)

*Primary Examiner*—Caixia Lu
(74) *Attorney, Agent, or Firm*—Richard R. Clikeman

(57) ABSTRACT

A catalytic composition, including a cationic metal-pair complex, is disclosed, along with a method for its preparation. A method for the polymerization of ethylenically unsaturated monomers using the catalytic composition, and the addition polymers produced thereby are also disclosed.

11 Claims, No Drawings

CATALYTIC COMPOSITION AND ITS PREPARATION AND USE FOR PREPARING POLYMERS FROM ETHYLENICALLY UNSATURATED MONOMERS

This patent application derives priority from U.S. patent application Ser. No. 60/579,360, filed, Jun. 14, 2004.

The present invention relates to a catalytic composition and a method of preparing that catalytic composition. The present invention further relates to a method for polymerizing ethylenically unsaturated monomers, including non-polar olefinic monomers, polar olefinic monomers, and combinations thereof, in the presence of the catalytic composition, and to the polymers produced thereby.

Both poly(non-polar)olefins and polyacrylates find their origins in the 1930's. At their inception, both families of polymers were made using free radical chemistry, and seventy years later acrylic polymers continue to be made predominately using free radical chemistry carried out predominately in batch mode. Ethylene polymerization, on the other hand, has enjoyed a number of breakthroughs so that today the preponderance of polyethylene produced (>80%) is prepared by continuous processes using transition metal catalysts. The use of transition metal catalysts has significantly improved economics (low energy, low pressure processes), greatly improved product properties (e.g., the strength of ultra-thin plastic bags), resulted in new products (new grades of polyethylene, elastomers, medical packaging) and even brand new polymers (e.g., polypropylene) by virtue of the molecular level control of polymer architecture endowed by these catalysts.

The evolution of olefin polymerization catalysis since Karl Ziegler's Nobel Prize-winning discovery of the transition metal catalyzed polymerization of ethylene in 1953 has involved a prolific coupling of polymer science with organometallic chemistry. Successes include the development of catalysts that rival the activities of enzymes, and of systems that yield polyolefins with controlled molecular weights and tacticities. In stark contrast, despite nearly 50 years of intense activity and progress spurred on by the predicted enormous profits associated with the new commercial products that would become accessible, there are no commercially viable catalysts for the polymerization of acrylates or the controlled copolymerization of simple olefins with polar functional monomers.

Currently, commercial processes for the copolymerization of ethylene with polar monomers such as acrylates, methacrylates, and vinyl acetate employ free radical processes in which the incorporation of the polar functionality is relatively random. The use of free radical initiators across the entire acrylic polymer market gives little or no control over polymer architecture (tacticity or crystallinity, blockiness, molecular weight, and molecular weight distribution) and thus limits the accessible range of materials performance properties. Because these free radical processes require extreme pressures, they are associated with high capital investment and manufacturing costs, and, of course, increased safety hazards.

Industry-wide, a need exists for new molecular catalysts capable of polymerizing polar monomers in a controlled fashion and for copolymerizing the same monomers with olefins (e.g. ethylene, propylene, styrene, octene, norbornene) under mild reaction conditions and in a stereoregular ("tactic") fashion. Of the many approaches to modifying the properties of a polymer that are available, the incorporation of functional groups into an otherwise non-polar material is of paramount importance. Polar groups exercise control over important polymer properties such as toughness, adhesion, barrier properties, and surface properties. These polymer properties manifest themselves in the properties of materials incorporating the polymer, such as solvent resistance, miscibility with other polymers, and rheological properties, leading to product performance such as paintability, printability, gloss, hardness, and mar resistance. By incorporating polar groups into hydrocarbon polymers such as polyethylene, polypropylene and polystyrene, not only would the important properties related to crystallinity (modulus, strength, solvent resistance, etc.) be maintained, but new properties would also be expressed.

In recent years, late transition metal catalysts have attracted attention not only for the polymerization of α-olefins, but more importantly for the copolymerization of hydrocarbon monomers with readily available polar monomers such as acrylates and vinyl acetate. Only very recently have these single metal centered catalysts provided the very first examples of the transition-metal catalyzed incorporation of acrylate monomers into linear polyethylene been demonstrated. Unfortunately, all of these reports describe catalysts with poor performance; low productivity, low molecular weight copolymers and low levels of polar monomer incorporation.

The total focus on single metal centered catalysts is apparent from myriad papers and reviews of the area. For example, Rolf Muelhaupt in "Catalytic Polymerization and Post Polymerization Catalysis Fifty Years After the Discovery of Ziegler's Catalysts", *Macromol. Chem. Phys.* 2003, 204, 289–327 elegantly and comprehensively reviews fifty years of developments and again we highlight that exclusively single metal or monometallic catalysts are described and reviewed—regardless of whether the catalysts are based on early transition metals such as titanium or zirconium, or late transition metals such as nickel and palladium, or whether the catalysts were studied in the 1950's, 60's, 70's, 80's, 90's or the present day. FIGS. 12 and 13 on page 298 of the Muelhaupt reference (vide supra) clearly summarize this concentration on single metal centers rather than the metal atom pair containing complexes of the present invention.

U.S. Pat. No. 6,303,724 discloses the use of specific monometallic cationic Pd complexes to polymerize mixtures of norbornene and acrylate monomers to make norbornene/acrylate compositions. Unfortunately, the method of U.S. Pat. No. 6,303,724 produces mixtures, the copolymer content of which is low (see Comparative Examples herein), so low, in fact, that these mixtures of polymers are ineffectual in uses for which a pure copolymer could be employed with advantageous result. In fact, in the presence of both norbornene and acrylate monomers, those monometallic cationic Pd complexes give only homopolymers of norbornene with no acrylate incorporation or, at most, homopolymers having a single acrylate monomer incorporated as an end group.

We have surprisingly discovered a catalytic composition including a new family of cationic metal-pair complexes which are very active in the homo- and co-polymerization of ethylenically unsaturated monomers. The ethylenically unsaturated monomers polymerizable by catalysis using the catalytic composition of the present invention include non-polar olefinic monomers, polar olefinic monomers, and combinations thereof. This new family of catalytic compositions includes cationic metal-pair complexes wherein the cationic metal-pair complex includes at least one metal atom pair, and one metal of the metal atom pair has six (6)

occupied coordination sites and the other metal of the metal atom pair has four (4), five (5), or six (6) occupied coordination sites.

One aspect of the present invention is directed to a catalytic composition comprising at least one cationic metal-pair complex, wherein:

said cationic metal-pair complex comprises at least one metal atom pair, said pair comprising a first metal atom, $M^1$, and a second metal atom, $M^2$;

said first metal atom and said second metal atom of said pair have a through-space internuclear distance of at least 1.5 Angstroms and no more than 20 Angstroms; and said cationic metal-pair complex is a complex according to formula I,

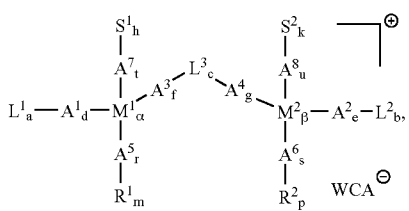

wherein:
$M^1$ represents a first metal atom selected from copper, iron, cobalt, ruthenium, rhodium, chromium, and manganese;
$L^1$ represents a set of first ligands;
$L^2$ represents a set of second ligands;
$L^3$ represents a set of third ligands;
$R^1$ represents a set of first anionic hydrocarbyl containing radicals;
$R^2$ represents a set of second anionic hydrocarbyl containing radicals;
$S^1$ represents a set of first labile ligands;
$S^2$ represents a set of second labile ligands;
$A^1$–$A^8$ each represent a set of coordination bonds;
WCA represents a weakly coordinating anion;
a, b, h, k, m, and p are each selected from 0 or 1;
$\alpha$, $\beta$, and c each equal 1;
d, r, and t are each selected from 0, 1, 2, 3, 4, or 5;
f is selected from 1, 2, 3, 4, 5, or 6;
$1 \leq m+p \leq 2$;
the sum $d+f+r+t=6$; and
sum $e+g+s+u=4$, 5, or 6; and
wherein:
when the sum $e+g+s+u=4$,
$M^2$ represents a second metal atom selected from nickel, palladium, copper, iron, cobalt, rhodium, chromium, and manganese;
e, s, and u are each selected from 0, 1, 2, or 3;
g is selected from 1, 2, 3, or 4;
$0 \leq d+e \leq 7$; $1 \leq r+s \leq 7$; $0 \leq t+u \leq 7$; and $2 \leq f+g \leq 9$;
when the sum $e+g+s+u=5$,
$M^2$ represents a second metal atom selected from iron, cobalt, ruthenium, rhodium, chromium, and manganese;
e, s, and u are each selected from 0, 1, 2, 3, or 4;
g is selected from 1, 2, 3, 4, or 5;
$0 \leq d+e \leq 8$; $1 \leq r+s \leq 8$; $0 \leq t+u \leq 8$; and $2 \leq f+g \leq 10$; or when the sum $e+g+s+u=6$,
$M^2$ represents a second metal atom selected from copper, iron, cobalt, ruthenium, rhodium, chromium, and manganese;
e, s, and u are each selected from 0, 1, 2, 3, 4, or 5;
g is selected from 1, 2, 3, 4, 5, or 6;
$0 \leq d+e \leq 9$; $1 \leq r+s \leq 9$; $0 \leq t+u \leq 9$; and $2 \leq f+g \leq 11$.

A second aspect of the present invention is directed to a method for preparing a catalytic composition, comprising:
(i) providing a full-(metal pair) precursor complex according to said formula II

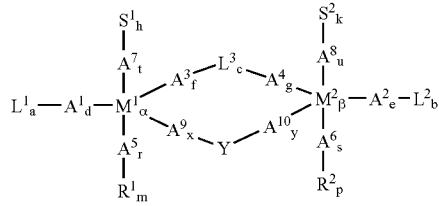

wherein:
$M^1$ represents a first metal atom selected from copper, iron, cobalt, ruthenium, rhodium, chromium, and manganese;
$L^1$ represents a set of first ligands;
$L^2$ represents a set of second ligands;
$L^3$ represents a set of third ligands;
$R^1$ represents a set of first anionic hydrocarbyl containing radicals;
$R^2$ represents a set of second anionic hydrocarbyl containing radicals;
$S^1$ represents a set of first labile ligands;
$S^2$ represents a set of second labile ligands;
$A^1$–$A^{10}$ each represents a set of coordination bonds;
WCA represents a weakly coordinating anion;
Y represents a leaving group;
$d+f+r+t+x=6$; and
the sum $e+g+s+u+y=4$, 5, or 6;
(ii) combining said full-(metal pair) precursor complex with at least one activator component;
(iii) removing said leaving group Y from said full-(metal pair) precursor complex; and
(iv) replacing said leaving group Y with at least one replacement moiety;

wherein for said full-(metal pair) precursor complex
$\alpha$, $\beta$, and c each equal 1;
a, b, h, k, m, p, x, and y are each selected from 0 or 1;
d, r, and t are each selected from 0, 1, 2, 3, 4, or 5;
f is selected from 1, 2, 3, 4, 5, or 6;
$1 \leq m+p \leq 2$; and
$1 \leq x+y \leq 2$; and
wherein:
when the sum $e+g+s+u+y=4$,
$M^2$ represents a second metal atom selected from nickel, palladium, copper, iron, cobalt, rhodium, chromium, and manganese;
e, s, and u are selected from 0, 1, 2, or 3;
g is selected from 1, 2, 3, or 4;
$0 \leq d+e \leq 6$; $1 \leq r+s \leq 7$; $0 \leq t+u \leq 6$; and $2 \leq f+g \leq 8$;
when the sum $e+g+s+u+y=5$,
$M^1$ represents a second metal atom selected from iron, cobalt, ruthenium, rhodium, chromium, and manganese;
e, s, and u are selected from 0, 1, 2, 3, or 4;

g is selected from 1, 2, 3, 4, or 5;
$0 \leq d+e \leq 7$; $1 \leq r+s \leq 8$; $0 \leq t+u \leq 7$; and $2 \leq f+g \leq 9$; or
when the sum $e+g+s+u+y=6$,
  $M^2$ represents a second metal atom selected from copper, iron, cobalt, ruthenium, rhodium, chromium, and manganese;
  e, s, and u are each selected from 0, 1, 2, 3, 4, or 5;
  g is selected from 1, 2, 3, 4, 5, or 6;
  $0 \leq d+e \leq 8$; $1 \leq r+s \leq 9$; $0 \leq t+u \leq 8$; and $2 \leq f+g \leq 10$.

A third aspect of the present invention is directed to a method for preparing a catalytic composition, comprising:
(i) providing a first semi-(metal pair) precursor complex and a second semi-(metal pair) precursor complex both according to formula II

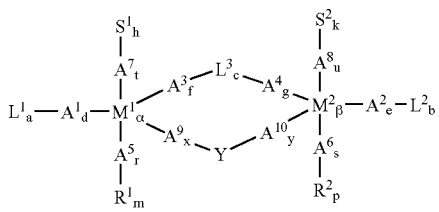

wherein:
$M^1$ represents a first metal atom selected from copper, iron, cobalt, ruthernium, rhodium, chromium, and manganese;
$L^1$ represents a set of first ligands;
$L^2$ represents a set of second ligands;
$L^3$ represents a set of third ligands;
$R^1$ represents a set of first anionic hydrocarbyl containing radicals;
$R^2$ represents a set of second anionic hydrocarbyl containing radicals;
$S^1$ represents a set of first labile ligands;
$S^2$ represents a set of second labile ligands;
$A^1$–$A^{10}$ each represents a set of coordination bonds;
WCA represents a weakly coordinating anion;
Y represents a leaving group;
$d+f+r+t+x=0$ or 6; and
the sum $e+g+s+u+y=4$, 5, or 6;
(ii) combining said first semi-(metal pair) precursor complex with at least one activator component;
(iii) removing said leaving group Y from said first semi-(metal pair) precursor complex; and
(iv) replacing said leaving group Y with said second semi-(metal pair) precursor complex;

wherein for said first semi-(metal pair) precursor complex
  α and x each equal 1;
  β, b, c, k, p, e, f, g, s, u, and y each equal 0;
  a, h, and m are each selected from 0 or 1;
  d, r, and t are each selected from 0, 1, 2, 3, 4, or 5; and
  the sum $d+f+r+t+x=6$; and wherein for said second semi-(metal pair) precursor complex
  β equals 1;
  α, a, c, h, m, d, f, g, r, t, x, and y each equal 0;
  b, k, and p are each selected from 0 or 1; and
  the sum $e+g+s+u+y=4$, 5 or 6; and wherein:
  when the sum $e+g+s+u+y=4$,
    $M^2$ represents a second metal atom selected from nickel, palladium, copper, iron, cobalt, rhodium, chromium, and manganese;
    e is selected from 0, 1, 2, 3, or 4; and
    s and u are each selected from 0, 1, 2, or 3;
  when the sum $e+g+s+u+y=5$,
    $M^2$ represents a second metal atom selected from iron, cobalt, ruthenium, rhodium, chromium, and manganese;
    e is selected from 0, 1, 2, 3, 4, or 5; and
    s and u are each selected from 0, 1, 2, 3, or 4; or
  when the sum $e+g+s+u+y=6$
    $M^2$ represents a second metal atom selected from copper, iron, cobalt, ruthenium, rhodium, chromium, and manganese;
    e is selected from 0, 1, 2, 3, 4, 5, or 6; and
    s and u are each selected from 0, 1, 2, 3, 4, or 5; and
wherein the sum of m of said first semi-(metal pair) precursor complex+p of said second semi-(metal pair) precursor complex is selected from 1 or 2.

A fourth aspect of the present invention is directed to a method for preparing a catalytic composition, comprising:
(i) providing a first semi-(metal pair) precursor complex and a second semi-(metal pair) precursor complex both according to formula II

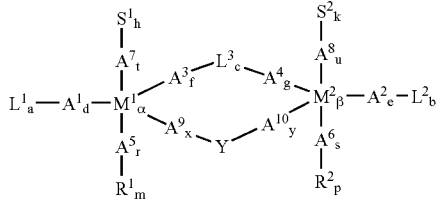

wherein:
$M^1$ represents a first metal atom selected from copper, iron, cobalt, ruthenium, rhodium, chromium, and manganese;
$L^1$ represents a set of first ligands;
$L^2$ represents a set of second ligands;
$L^3$ represents a set of third ligands;
$R^1$ represents a set of first anionic hydrocarbyl containing radicals;
$R^2$ represents a set of second anionic hydrocarbyl containing radicals;
$S^1$ represents a set of first labile ligands;
$S^2$ represents a set of second labile ligands;
$A^1$–$A^{10}$ each represents a set of coordination bonds;
WCA represents a weakly coordinating anion;
Y represents a leaving group;
$d+f+r+t+x=6$; and
the sum $e+g+s+u+y=4$, 5, or 6;
(ii) combining said first semi-(metal pair) precursor complex with at least one activator component;
(iii) removing said leaving group Y from said first semi-(metal pair) precursor complex; and
(iv) replacing said leaving group Y with said second semi-(metal pair) precursor complex;

wherein for said first semi-(metal pair) precursor complex
  β and y each equal 1;
  β, a, c, h, m, d, f, g, r, t, and x each equal 0;
  b, k, and p are each selected from 0 or 1; and the sum e+g+s+u+y=4, 5 or 6; and
wherein:
when the sum e+g+s+u+y=4,
$M^2$ represents a second metal atom selected from nickel, palladium, copper, iron, cobalt, rhodium, chromium, and manganese; and
e, s and u are each selected from 0, 1, 2, or 3;
when the sum e+g+s+u+y=5,
$M^2$ represents a second metal atom selected from iron, cobalt, ruthenium, rhodium, chromium, and manganese; and
e, s and u are each selected from 0, 1, 2, 3, or 4; or
when the sum e+g+s+u+y=6
$M^2$ represents a second metal atom selected from copper, iron, cobalt, ruthenium, rhodium, chromium, and manganese; and
e, s and u are each selected from 0, 1, 2, 3, 4, or 5; and wherein for said second semi-(metal pair) precursor complex
α equals 1;
β, b, c, k, p, e, f; g, s, u, x, and y each equal 0;
a, h, and m are each selected from 0 or 1;
d is selected from 0, 1, 2, 3, 4, 5, or 6;
r and t are each selected from 0, 1, 2, 3, 4, or 5; and
the sum d+f+r+t+x=6; and
wherein the sum of m of said first semi-(metal pair) precursor complex+p of said second semi-(metal pair) precursor complex is selected from 1 or 2.

A still further aspect of the present invention is directed to a method for preparing at least one addition polymer comprising
(a) combining:
(i) catalytic composition according to claim 1; and
(ii) at least one ethylenically unsaturated monomer; and
(b) polymerizing said at least one ethylenically unsaturated monomer in the presence of said catalytic composition to form said addition polymer.

Used herein, the following terms have these definitions:
"Range". Disclosures of ranges herein take the form of lower and upper limits. There may be one or more lower limits and, independently, one or more upper limits. A given range is defined by selecting one lower limit and one upper limit. The selected lower and upper limits then define the boundaries of that particular range. All ranges that can be defined in this way are inclusive and combinable, meaning that any lower limit may be combined with any upper limit to delineate a range.

A "catalytic composition" is a composition including at least one "cationic metal-pair complex", wherein the cationic metal-pair complex includes at least one "metal atom pair". Each metal atom pair includes a single "first metal atom" represented by the symbol "$M^1$" ("metal atom $M^1$") and a single "second metal atom" represented by the symbol "$M^2$" ("metal atom $M^2$").

The "through-space internuclear metal atom pair distance" (referred to interchangeably, herein, as "through-space internuclear distance") for a metal atom pair of a cationic metal-pair complex is the distance between the nucleus of the first metal atom $M^1$ of a metal atom pair and the nucleus of the second metal atom $M^2$ of that pair. This through-space internuclear distance is equal to or less than the "through-bond internuclear distance", which is the distance traced along connecting bonds. For example, if a metal-metal bond exists between $M^1$ and $M^2$ of a metal atom pair, the through-space internuclear distance and the metal-metal through-bond distance are the same. If this metal atom pair also had a third ligand as a bridging moiety between $M^1$ and $M^2$, the distance from $M^1$ to $M^2$ along the bonds of that third ligand would be greater than the through-space distance.

The "through-space internuclear metal atom pair distance" for a metal pair of a cationic metal-pair complex may be determined using quantum chemical calculation methods known to those of ordinary skill in the art of computational chemistry. For example, a quantum chemical calculation method suitable for use with the present invention includes density functional methods such as JAGUAR™ software, Version 5.0. For a given cationic metal-pair complex, one of ordinary skill in the art of computational chemistry can utilize accepted rules of chemical connectivity, the "LACVP basis set", and the "B3LYP functional" to calculate the interatomic metal-metal distance (i.e., the through-space internuclear metal atom pair distance) for a metal pair of that cationic metal-pair complex. Using JAGUAR™ software, Version 5.0, the structure of the cationic metal-pair complex is geometry optimized, using as a starting point a structure having the proper atomic connectivity. The metal-metal interatomic distance for a metal pair of that complex (i.e., the "through-space internuclear metal pair distance") can then be determined from the atomic cartesian coordinates of the geometry optimized structure. JAGUAR™ Verion 5.0 software and the Jaguar 5.0 Operating Manual, January 2003, are available from Schrödinger, L. L. C., 120 West $45^{th}$ Street, $32^{nd}$ Floor, New York, N.Y. 10036.

The first metal atom and the second metal atom of a metal atom pair may further exhibit "cooperativity" during the polymerization of ethylenically unsaturated monomers, wherein cooperativity means that the first metal atom will positively influence the ability of the second metal atom to polymerize ethylenically unsaturated monomer, or the second metal atom will positively influence the ability of the first metal atom to polymerize ethylenically unsaturated monomer, or both. Not wishing to be bound by any particular theory, it is thought that, when the two metals of a metal atom pair exhibit cooperativity, that cooperativity may, for example, take the form wherein a metal of the pair favorably modifies the electronic, steric, or other spatial environment of the other metal of the pair, or of the inserting ethylenically unsaturated monomer, or of the portion of any polymer chain growing from, or otherwise associated with, the metal atom pair. In certain embodiments, a single ethylenically unsaturated monomer may become attached to, or otherwise associated with, each of the members of a metal atom pair, either sequentially or simultaneously, during its incorporation into a polymer by insertion polymerization catalyzed by that metal atom pair.

A "coordination bond" can be a bond between a "coordination site" of a first metal atom, $M^1$, and any one of the following: first ligand; bridging moiety; first anionic hydrocarbyl radical; first labile ligand; or metal atom $M^2$. A "coordination bond" can also be a bond between a "coordination site" of a second metal atom, $M^2$, and any one of the following: second ligand; bridging moiety; second anionic hydrocarbyl radical; second labile ligand; or metal atom $M^1$. A set of coordination bonds is represented by the symbol "A", having a superscript denoting the position of that bond in the "cationic metal-pair complex formula" (vide infra) and a subscript denoting the number of coordination bonds.

The term "ligand" has its usual meaning in organometallic chemistry. A "ligand" is a moiety bearing one or more "donor sites", wherein a "donor site" is an electron rich site (e.g., lone electron pair) capable of forming a "coordination bond" with a metal atom by donating electron density to an unoccupied (i.e., electron deficient) "coordination site" on that metal atom. The ligand is said to be "occupying that coordination site" on that metal atom. Alternatively, the ligand is said to be "coordinately bound" to the metal atom. When one or more coordination bonds exist between a ligand and a metal atom, both that ligand and that metal atom are said to be "participating" in each of those coordination bonds.

A "neutral electron donor ligand" is any ligand which, when removed from a metal atom (i.e., one or more coordination bonds are broken) in its closed shell electron configuration, has a neutral charge. For example, triphenylphosphine is a neutral electron donor ligand.

A "monodentate ligand" is a ligand bearing a single "donor site". For example, triphenylphosphine is a monodentate ligand, the phosphorus lone electron pair of which is a donor site capable of coordinating to (i.e., occupying a coordination site of) a metal atom.

A "bidentate ligand" is a ligand bearing two donor sites. For example, 1,2-bis(diphenylphosphino)ethane is a bidentate ligand. Each of the two donor sites of a bidentate ligand may be able to form a coordination bond to the same metal atom. Alternatively, one donor site of a bidentate ligand may form a coordination bond to one metal atom, while the other donor site of the same bidentate ligand may form a coordination bond to a different metal atom.

A "multi-dentate ligand" bears two or more donor sites, each of which is capable of coordinating to a metal atom. For example, pentamethyldiethylenetriamine is a multi-dentate ligand having three such donor sites. Provided that such considerations as steric and electronic factors allow it, each of the donor sites of a multi-dentate ligand may be able to form a coordination bond to the same metal atom. Alternatively, at least one donor site of a multi-dentate ligand may form a coordination bond to one metal atom, while at least one other donor site of the same multi-dentate ligand may form a coordination bond to a different metal atom, and each of those two metal atom could be in the same metal-atom pair, or in two different metal-atom pairs of the complex that contains one or more metal-atom pairs. A "bidentate ligand" is a special case of a "multi-dentate ligand".

It is further possible that fewer than all of the donor sites of a ligand may actually participate in coordination bonds. Therefore, for any ligand, the "effective number of donor sites" of that ligand is equal to the number of donor sites actually participating in coordination bonds. It follows that an "effectively monodentate ligand" is a ligand having a total of one donor site participating in a coordination bond. Similarly, for example. "effectively bidentate", "effectively tridentate", "effectively tetradentate", "effectively pentadentate", and "effectively hexadentate" ligands have, respectively, two, three, four, five, and six donor sites participating in coordination bonds. As a further example, pentamethyldiethylenetriamine has three amine lone electron pairs as donor sites, and is therefore a tridentate ligand. If only two of the amine lone electron pairs of this triamine were participating in coordination bonds with one metal, or two metals of a metal atom pair, the triamine would be effectively bidentate with respect to that metal atom pair. If only one of those electron pairs were participating in a coordination bond with a metal, the triamine would be effectively monodentate. As a further example, the allyl anion is effectively monodentate in its $\eta^1$-allyl form, but effectively bidentate in its $\eta^3$-allyl form.

A "first ligand" may be any ligand capable of participating in one or more coordination bonds with metal atom $M^1$ of a metal atom pair, while not simultaneously participating in a coordination bond with metal atom $M^2$ of that same metal atom pair.

A "second ligand" may be any ligand capable of participating in one or more coordination bonds with metal atom $M^2$ of a metal atom pair, while not simultaneously participating in a coordination bond with metal atom $M^1$ of that same metal atom pair.

A "third ligand" of the present invention may be any ligand capable of participating, simultaneously, in at least one coordination bond with each of metal atom $M^1$ and metal atom $M^2$, of the same metal atom pair. The terms "third ligand" and "bridging moiety" are used interchangeably herein.

A "labile neutral electron donor ligand" is any neutral electron donor ligand which is not strongly bound to a metal atom (e.g., $M^1$ or $M^2$), and is easily displaced therefrom. The terms "labile neutral electron donor ligand" and "labile ligand" are used interchangeably herein.

A "first labile ligand" is a labile ligand capable of participating in a coordination bond with metal atom $M^1$, while not simultaneously participating in a coordination bond with metal atom $M^2$.

A "second labile ligand" is a labile ligand capable of participating in a coordination bond with metal atom $M^2$, while not simultaneously participating in a coordination bond with metal atom $M^1$.

An anionic ligand, is any ligand which, when removed from a metal atom (e.g., $M^1$ or $M^2$) in its closed shell electron configuration, has a negative charge.

A "multi-(metal pair) coupling moiety", referred to herein, interchangeably, as a "pair-coupling moiety" is any multi-dentate moiety capable of participating, simultaneously, in at least one coordination bond with each of at least two metal atom pairs of a single complex. A "pair-coupling moiety" includes multiple donor sites having constraints (for example, steric constraints, electronic constraints, or both) allowing one or more of those donor sites to participate in coordination bonds with one metal pair while, simultaneously, one or more of its other donor sites is participating in coordination bonds with another metal pair. Though not wishing to be bound by any particular theory, it is believed that the number of metal pairs that can simultaneously participate in one or more coordination bonds with the same pair-coupling moiety is governed by such considerations as, for example: steric constraints of the pair-coupling moiety; electronic constraints of the donor sites of the pair-coupling moiety; electronic and spatial characteristics of metal atoms $M^1$ and $M^2$ within and, where there are multiple metal-atom pairs in the same complex, between metal atom pairs; steric and electronic characteristics of any other first ligand, second ligand, bridging moiety, first anionic hydrocarbyl containing radical, second anionic hydrocarbyl containing radical, first labile ligand, second labile ligand, or leaving group that is simultaneously participating in a coordination bond, or bonds, with either metal atom $M^1$ or $M^2$ of each metal atom pair; the mole ratios of the pair-coupling moiety to the metal pairs; and the accessibility of donor sites (e.g., a pair-coupling moiety may be a porous polymeric structure, wherein some donor sites may be inaccessible to metal atom pairs). Further, the maximum number of metal atom pairs that may possibly be coordinately bound to a single pair-coupling moiety is equal to the number of donor sites on that pair-coupling moiety. However, one or more of the constraints listed supra may intervene to limit the number of metal atom pairs that are actually bound to a single pair-coupling moiety to a number less than that maximum value. It may also be the case that a single pair-coupling moiety may participate in multiple coordination bonds with one or both of metal atoms $M^1$ and $M^2$ of a single metal pair. There is no particular limit on the size of the pair-coupling moiety. For example, the pair-coupling moiety may be a macroreticular resin bearing donor sites (vide infra), a crown ether, or other macrostructure bearing multiple donor sites.

A "pair-coupling moiety" is a moiety capable of participating in coordination bonds with two or more metal atom pairs of a complex of the present invention, provided, of course, that the complex has at least two metal atom pairs and that constraints such as those just enumerated allow coordination bonds to multiple metal atom pairs. The following complexes of the present invention may contain one or more pair-coupling moieties: cationic metal-pair complex; and precursor complexes, including full-(metal pair) precursor complex; first semi-(metal pair) precursor complex; and second semi-(metal pair) precursor complex. When two or more metal atom pairs are present in a complex of the present invention: all of metal atoms $M^1$ may be identical (e.g., all might be Ni); all of metal atoms $M^2$ may be identical; metal atom $M^1$ may differ from pair to pair (e.g., one might be Ni, while another would be Pd); and metal atom $M^2$ may differ from pair to pair. In the case of first and second semi-(metal pair) complexes, either metal atom $M^1$ or $M^2$, but not both, will be present in each pair of the semi-(metal pair) complex. A "pair-coupling moiety" may be any of the following: first ligand, second ligand, third ligand, first labile ligand, second labile ligand, first hydrocarbyl radical, second hydrocarbyl radical, or combinations thereof.

A "weakly coordinating anion" ("WCA") is an anion which is only weakly associated with the cationic metal-pair complex. The WCA is sufficiently labile to be displaced by a neutral Lewis base, solvent or monomer. More specifically, the WCA functions as a stabilizing anion to the cationic metal-pair complex and does not transfer sufficient electron density to the cationic metal-pair complex to form a neutral product. The WCA is relatively inert in that it is non-oxidative, non-reducing, and non-nucleophilic.

A "cationic metal-pair complex" is a complex represented by the following "cationic metal-pair complex formula" ("formula I"):

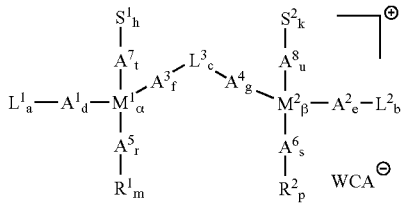

(formula I)

and the following symbols and subscripts have these meanings in the cationic metal-pair complex formula:

The symbols "$M^1$" and "$M^2$" represent, respectively, a first metal atom of a metal atom pair and a second metal atom of a metal atom pair. The cationic metal-pair formula subscript "$\alpha$" on the symbol "$M^1_\alpha$", indicates whether metal atom $M^1$ is present in ($\alpha$=1) or absent from ($\alpha$=0) a metal atom pair of a cationic metal-pair complex. The cationic metal-pair formula subscript "$\beta$" on the symbol "$M^2_\beta$", indicates whether metal atom $M^2$ is present in ($\beta$=1) or absent from ($\beta$=0) a metal atom pair of a cationic metal-pair complex. Because both of metal atoms $M^1$ and $M^2$ must be present in any metal atom pair of a cationic metal-pair complex, the following relationship exists: $\alpha=\beta=1$.

The symbol "$L^1$" represents a "set of first ligands", wherein a "first ligand" is a ligand coordinately bound to metal atom $M^1$, but not coordinately bound to metal atom $M^2$. This set of first ligands may, interchangeably, be referred to as "set $L^1$". The cationic metal pair-complex formula subscript "a", of "$L^1_a$", equals either the integer 0 or 1. When "a"=1, set $L^1$ includes one or more first ligands. When "a"=0, set $L^1$ is "empty". When a ligand set is empty, that ligand set contains no ligands. For example, when "a"=0, set $L^1$ contains no first ligands.

The symbol "$L^2$" represents a "set of second ligands", wherein a "second ligand" is a ligand coordinately bound to metal atom $M^2$, but not coordinately bound to metal atom $M^1$. This set of second ligands may, interchangeably, be referred to as "set $L^2$". The cationic metal pair-complex formula subscript "b", of "$L^2_b$", equals either 0 or 1. When "b"=1, set $L^2$ includes one or more second ligands. When "b"=0, set $L^2$ is empty.

The symbol "$L^3$" represents a "set of bridging moieties". A "bridging moiety" is a moiety coordinately bound to both metal atom $M^1$ and metal atom $M^2$ of the same metal atom pair. A metal-metal bond is a special case of a bridging moiety wherein the moiety is the bond itself, and involves no other atoms beyond the two metal atoms of the metal-metal bond. This set of bridging moieties may, interchangeably, be referred to as "set $L^3$". The cationic metal pair-complex formula subscript "c", of "$L^3_c$", equals 1 in the cationic metal-pair complex formula, indicating that set $L^3$ includes one or more bridging moieties. The terms "bridging moiety" and "third ligand" are used interchangeably herein. Bridging moieties include any multi-dentate ligand capable of being simultaneously coordinately bound to both metal atom $M^1$ and metal atom $M^2$. A crown ligand (e.g., "cationic metal-pair complex 1" infra) is therefor a bridging moiety and a member of set $L^3$ if it is simultaneously coordinately bound to both metal atom $M^1$ and metal atom $M^2$. "Third labile ligands", "third anionic hydrocarbyl containing radicals", and "metal-metal bonds" between metal atom $M^1$ and metal-atom $M^2$ of a metal atom pair are included in the definition of "third ligand" ("bridging moiety").

The symbol "$R^1$" represents a "set of first anionic hydrocarbyl containing radicals" coordinately bound to metal atom $M^1$, but not to metal atom $M^2$. This set of first anionic hydrocarbyl containing radicals may, interchangeably, be referred to as "set $R^1$". Herein, the term "first hydrocarbyl radical" is used interchangeably with the term "first anionic hydrocarbyl containing radical". The cationic metal pair-complex formula subscript "m", of "$R^1_m$", equals either 0 or 1. When "m"=1, set $R^1$ includes one or more first hydrocarbyl radicals. When "m"=0, set $R^1$ is empty.

The symbol "$R^2$" represents a "set of second anionic hydrocarbyl containing radicals" coordinately bound to metal atom $M^2$, but not to metal atom $M^1$. This set of second anionic hydrocarbyl containing radicals may, interchangeably, be referred to as "set $R^2$". Herein, the term "second hydrocarbyl radical" is used interchangeably with the term "second anionic hydrocarbyl containing radical". The subscript "p", of "$R^2_p$", equals either the integer 0 or 1. When subscript "p"=1, set $R^2$ includes one or more second hydrocarbyl radicals. When subscript "p"=0, set $R^2$ is empty. The relationship that, if one of the sets $R^1$ and $R^2$ is empty, then the other set must contain at least one hydrocarbyl radical is represented by the following relationship: $1 \leq m+p \leq 2$.

It is also possible for a hydrocarbyl radical to simultaneously participate in at least one coordination bond of each of first metal atom, $M^1$, and second metal atom, $M^2$, of the same metal atom pair. This case is described herein as a "third anionic hydrocarbyl containing radical", alternatively "third hydrocarbyl radical". A "third hydrocarbyl radical" is a special case of a "bridging moiety", $L^3$.

An "anionic hydrocarbyl containing radical" (interchangeably, "hydrocarbyl radical") is any hydrocarbyl radical which, when removed from a metal atom (e.g., $M^1$ or $M^2$) in its closed shell electron configuration, has a negative charge. In any complex of the present invention in which they both are present, a first hydrocarbyl radical and a second hydrocarbyl radical may be the same or different. When a set $R^1$ contains more than one first hydrocarbyl radical, those first hydrocarbyl radicals may all be the same, or one or more may be different from at least one other first hydrocarbyl radical of that set $R^1$. When a set $R^2$ contains more than one second hydrocarbyl radical, those second hydrocarbyl radicals may all be the same, or one or more may be different from at least one other second hydrocarbyl radical of that set $R^2$.

The symbol "$S^1$" represents a "set of first labile ligands", wherein a "first labile ligand" is a labile ligand coordinately bound to: metal atom $M^1$, but not coordinately bound to metal atom $M^2$. This set of first labile ligands may, interchangeably, be referred to as "set $S^1$". The cationic metal pair-complex formula subscript "h", of "$S^1_h$", equals either 0 or 1. When "h"=1, set $S^1$ includes one or more first labile ligands. When "h"=0, set $S^1$ is "empty". When a labile ligand set is empty, that labile ligand set contains no ligands. For example, when "h"=0, set $S^1$ is empty. When set $S^1$ contains more than one first labile ligand, those first labile ligands may all be the same, or one or more may be different from at least one other first labile ligand of that set $S^1$.

The symbol "$S^2$" represents a "set of second labile ligands", wherein a "second labile ligand" is a labile ligand coordinately bound to metal atom $M^2$, but not coordinately bound to metal atom $M^1$. This set of second labile ligands may, interchangeably, be referred to as "set $S^2$". The cationic metal pair-complex formula subscript "k", of "$S^2_k$", equals either 0 or 1. When "k"=1, set $S^2$ includes one or more second labile ligands. When "k"=0, set $S^2$ is empty. When a set $S^2$ contains more than one second labile ligand, those second labile ligands may be all the same, or one or more may be different from at least one other second labile ligand of that set $S^2$. In any cationic metal-pair complex of the present invention in which they both are present, a first labile ligand and a second labile ligand may be the same or different.

It is also possible for a labile ligand to simultaneously participate in at least one coordination bond of each of first metal atom, $M^1$, and second metal atom, $M^2$, of the same metal atom pair. This case is described herein as a "third labile ligand". A "third labile ligand" is a special case of a "bridging moiety", $L^3$.

The symbol "$A^1$" represents a set of coordination bonds between any first ligands of set $L^1$ and first metal atom $M^1$ of a metal atom pair of the cationic metal-pair complex.

The symbol "$A^2$" represents a set of coordination bonds between any second ligands of set $L^2$ and second metal atom, $M^2$ of a metal atom pair of the cationic metal-pair complex.

The symbol "$A^3$" represents a set of coordination bonds between any bridging moieties of set $L^3$ and first metal atom, $M^1$ of a metal atom pair of the cationic metal-pair complex.

The symbol "$A^4$" represents a set of coordination bonds between any bridging moieties of set $L^3$ and second metal atom, $M^2$ of a metal atom pair of the cationic metal-pair complex.

The symbol "$A^5$" represents a set of coordination bonds between any first hydrocarbyl radicals of set $R^1$ and first metal atom, $M^1$ of a metal atom pair of the cationic metal-pair complex.

The symbol "$A^6$" represents a set of coordination bonds between any second hydrocarbyl radicals of set $R^2$ and second metal atom, $M^2$ of a metal atom pair of the cationic metal-pair complex.

The symbol "$A^7$" represents a set of coordination bonds between any first labile ligands of set $S^1$ and first metal atom, $M^1$ of a metal atom pair of the cationic metal-pair complex.

The symbol "$A^8$" represents a set of coordination bonds between any second labile ligands of set $S^2$ and second metal atom $M^2$ of a metal atom pair of the cationic metal-pair complex.

Any of the sets of coordination bonds represented by the symbol "A" may, interchangeably, be referred to as "set A". For example, the set of coordination bonds represented by the symbol "$A^1$" may, interchangeably, be referred to as "set $A^1$".

If any of sets $L^1$, $L^2$, $R^1$, $R^2$, $S^1$, and $S^2$ is empty, the cation formula subscript of any symbol "A" representing any coordination bonds directly associated with that set will equal 0. For example, if set $L^1$ is empty, "a" of "$L^1_a$" equals 0, and "d" of "$A^1_d$", also equals 0. It follows that, if any of cationic metal pair-complex formula subscripts "a", "b", "h", "k", "m", and "p" equal 0, then the corresponding cationic metal pair-complex formula subscripts "d", "e", "t", "u", "r", and "s" will, respectively, equal 0. These relationships also exist among the precursor formula subscripts of the "precursor complex formula" (vide infra).

If any of sets $L^1$, $L^2$, $L^3$, $R^1$, $R^2$, $S^1$, and $S^2$ is occupied, i.e., contains at least one member of its set, the cationic metal pair-complex formula subscript of any symbol "A", representing any coordination bonds directly associated with a member of that set, will equal at least 1. That is, for any of sets $L^1$, $L^2$, $L^3$, $R^1$, $R^2$, $S^1$, and $S^2$ that are occupied, the corresponding cationic metal pair-complex formula subscripts d, e, f, g, r, s, t, or u will, respectively, equal at least 1. For example, if set $L^1$ of a "cationic metal-pair complex" is occupied, "a" of "$L^1_a$" equals 1, and "d" of "$A^1_d$", equals at least 1. Further, if any of sets $L^1$, $L^2$, $L^3$, $R^1$, $R^2$, $S^1$, and $S^2$ is occupied, and the cationic metal pair-complex formula subscript of a symbol "A" representing coordination bonds directly associated with a member, or members, of that set equals at least 2, the plural coordination bonds indicated by that subscript may all emanate from a single member of that set, or, alternatively, emanate from more than one member of that set. For example, if "e", of "$A^2_e$", equals the integer 3, then set $L^2$ may contain one, two, or three second ligands. In this example, set $L^2$ may contain any of these combinations: three effectively monodentate second ligands (vide supra); one effectively monodentate second ligand and one effectively bidentate second ligand; or one effectively tridentate second ligand.

When a "metal-metal bond" exists between first metal atom, $M^1$, and second metal atom, $M^2$, of a metal atom pair of a cationic metal-pair complex, the presence of that metal-metal bond is indicated in the cationic metal-pair complex formula by incrementing both of subscripts "f" and "g" by 1. In this specific case of a metal-metal bond, the combination of an $A^3$ bond and an $A^4$ bond represents one single bond because there exist no atoms in the bridging moiety, that is, the electron cloud of the bond between metal atom $M^1$ and metal atom $M^2$ is the bridging moiety. This same formalism, wherein both subscripts "f" and "g" are incremented by 1 to indicate a metal-metal bond, holds when a metal-metal bond exists between a first metal atom, $M^1$, and a second metal atom, $M^2$, of a "precursor complex" of the present invention (i.e., when the precursor complex is a full-(metal pair) precursor complex).

The "cationic metal-pair complex formula subscripts" have values which are either positive integers or zero. $M^1$ and $M^2$, and cationic metal pair-complex formula subscripts have these definitions: a, b, h, k, m, and p are selected from 0 or 1; $\alpha$, $\beta$, and c each equal 1; d, r, and t are each selected from 0, 1, 2, 3, 4 or 5; f is selected from 1, 2, 3, 4, 5, or 6; $1 \leq m+p \leq 2$; the sum $d+f+r+t=6$; and sum $e+g+s+u=4$, 5, or 6; and wherein:

$M^1$ represents a first metal atom selected from iron, cobalt, ruthenium, rhodium, chromium, and manganese; and when the sum $e+g+s+u=4$, $M^2$ represents a second metal atom selected from nickel, palladium, copper, iron, cobalt, rhodium, chromium, and manganese; e, s, and u are each selected from 0, 1, 2, or 3; g is selected from 1, 2, 3, or 4; $0 \leq d+e \leq 7$; $1 \leq r+s \leq 7$; $0 \leq t+u \leq 7$; and $2 \leq f+g \leq 9$;

when the sum $e+g+S+u=5$, $M^2$ represents a second metal atom selected from iron, cobalt, ruthenium, rhodium, chromium, and manganese; e, s, and u are each selected from 0, 1, 2, 3, or 4; g is selected from 1, 2, 3, 4, or 5; $0 \leq d+e \leq 8$; $1 \leq r+s \leq 8$; $0 \leq t+u \leq 8$; and $2 \leq f+g \leq 10$; or when the sum $e+g+s+u=6$, $M^2$ represents a second metal atom selected from copper, iron, cobalt, ruthenium, rhodium, chromium, and manganese; e, s, and u are each selected from 0, 1, 2, 3, 4, or 5; g is selected from 1, 2, 3, 4, 5, or 6; $0 \leq d+e \leq 9$; $1 \leq r+s \leq 9$; $0 \leq t+u \leq 9$; and $2 \leq f+g \leq 11$.

A "precursor complex" is a complex according to the following "precursor complex formula" ("formula II"):

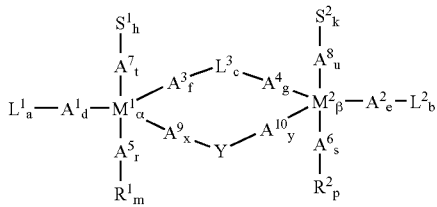

(formula II)

Symbols "$M^1$", "$M^2$", "$R^1$", "$R^2$", "$L^1$", "$L^2$", "$L^3$", "$S^1$", and "$S^2$", of the "precursor complex formula" have, respectively, the same meaning as the symbols $M^1$, $M^2$, $R^1$, $R^2$, $L^1$, $L^2$, $L^3$, $S^1$, and $S^2$ of the "cationic metal-pair complex formula".

Symbols "$A^1$", "$A^2$", "$A^3$", "$A^4$", "$A^5$", "$A^6$", "$A^7$" and "$A^8$", of the "precursor complex formula" have, respectively, the same meaning as the symbols $A^1$, $A^2$, $A^3$, $A^4$, $A^5$, $A^6$, $A^7$, and $A^8$ of the "cationic metal-pair complex formula".

Although both $M^1$ and $M^2$ of the at least one metal atom pair of the "cationic metal-pair complex" are always present in the "cationic metal-pair complex", one member of the at least one metal atom pair of the "precursor complex" may be absent. For that reason precursor formula subscripts "$\alpha$" and "$\beta$" have, respectively been added to "$M^1$" and "$M^2$" in the "precursor complex formula". The precursor formula subscript "a" on the symbol "$M^1_\alpha$", indicates whether metal atom $M^1$ is present in ($\alpha=1$) or absent from ($\alpha=0$) a metal atom pair of a precursor complex. The precursor formula subscript "$\beta$" on the symbol "$M^2_\beta$", indicates whether metal atom $M^2$ is present in ($\beta=1$) or absent from ($\beta=0$) a metal atom pair of a precursor complex. Because either one or both of metal atoms $M^1$ and $M^2$ must be present in any metal atom pair of a precursor complex, the following relationship exists: $1 \leq \alpha+\beta \leq 2$. The "precursor complex subscripts" have values which are either positive integers or zero.

Symbol "Y" represents a leaving group of the precursor complex.

A "leaving group" is a moiety capable of being removed from the precursor complex of the present invention by the action of an "activator component".

Symbol "$A^9$" represents a set of coordination bonds between leaving group Y and first metal atom, $M^1$ of a metal atom pair of a precursor complex.

Symbol "$A^{10}$" represents a set of coordination bonds between leaving group Y and second metal atom, $M^2$ of a metal atom pair of a precursor complex.

An "activator component" is a moiety capable of removing a leaving group Y from a "coordination site" of: metal atom $M^1$ of a precursor complex; metal atom $M^2$ of the precursor complex; or each of metal atom $M^1$ and metal atom $M^2$ of the precursor complex.

A "full-(metal-pair) precursor complex" is a precursor complex according to the precursor complex formula (formula II) wherein $M^1$ represents a first metal atom selected from copper, iron, cobalt, ruthenium, rhodium, chromium, and manganese, and $M^2$ and the precursor formula subscripts have these definitions: $d+f+r+t+x=6$; the sum $e+g+s+u+y=4$, 5, or 6; $\alpha$, $\beta$, and c each equal 1; a, b, h, k, m, p, x, and y are each selected from 0 and 1; d, r, and t are each selected from 0, 1, 2, 3, 4, and 5; f is selected from 1, 2, 3, 4, 5, and 6; $1 \leq m+p \leq 2$; and $1 \leq x+y \leq 2$; and wherein: when the sum $e+g+s+u+y=4$, $M^2$ represents a second metal atom selected from nickel, palladium, copper, iron, cobalt, rhodium, chromium, and manganese;

e, s, and u are selected from 0, 1, 2, and 3;

g is selected from 1, 2, 3, and 4;

$0 \leq d+e \leq 6$; $1 \leq r+s \leq 7$; $0 \leq t+u \leq 6$; and $2 \leq f+g \leq 8$;

when the sum $e+g+s+u+y=5$, $M^2$ represents a second metal atom selected from iron, cobalt, ruthenium, rhodium, chromium, and manganese;

e, s, and u are selected from 0, 1, 2, 3, and 4;

g is selected from 1, 2, 3, 4, and 5;

$0 \leq d+e \leq 7$; $1 \leq r+s \leq 8$; $0 \leq t+u \leq 7$; and $2 \leq f+g \leq 9$; or when the sum $e+g+s+u+y=6$, $M^2$ represents a second metal atom selected from copper, iron, cobalt, ruthenium, rhodium, chromium, and manganese;

e, s, and u are each selected from 0, 1, 2, 3, 4, and 5;

g is selected from 1, 2, 3, 4, 5, and 6;

$0 \leq d+e \leq 8$; $1 \leq r+s \leq 9$; $0 \leq t+u \leq 8$; and $2 \leq f+g \leq 10$.

A "first semi-(metal-pair) precursor complex" is a precursor complex according to the precursor complex formula (formula II) wherein $M^1$ and $M^2$, and the precursor formula subscripts have these definitions:

when $\alpha$ equals 1:

$M^1$ represents a first metal atom selected from copper, iron, cobalt, ruthenium, rhodium, chromium, and manganese; x equals 1; $\beta$, b, c, k, p, e, f, g, s, u, and y each equal 0; a, h, and m are each selected from 0 and 1; and d, r, and t are each selected from 0, 1, 2, 3, 4, and 5; and $d+f+r+t+x=6$; and when β equals 1;
  y equals 1; α, a, c, h, m, d, f, g, r, t, and x each equal 0;
  b, k, and p are each selected from 0 and 1; and
  the sum e+g+s+u+y=4, 5 or 6; and
  wherein:
    when the sum e+g+s+u+y=4,
      $M^2$ represents a second metal atom selected from nickel, palladium, copper, iron, cobalt, rhodium, chromium, and manganese; and
      e, s and u are each selected from 0, 1, 2, and 3;
    when the sum e+g+s+u+y=5,
      $M^2$ represents a second metal atom selected from iron, cobalt, ruthenium, rhodium, chromium, and manganese; and
      e, s and u are each selected from 0, 1, 2, 3, and 4; or
    when the sum e+g+s+u+y=6
      $M^2$ represents a second metal atom selected from copper, iron, cobalt, ruthenium, rhodium, chromium, and manganese; and
      e, s and u are each selected from 0, 1, 2, 3, 4, and 5.

A "second semi-(metal-pair) precursor complex" is a precursor complex according to the precursor complex formula (formula II) wherein $M^1$ and $M^2$, and the precursor formula subscripts have these definitions:
when β equals 1:
  α, a, c, h, m, d, f, g, r, t, x, and y each equal 0; b, k, and p are each selected from 0 or 1; and
  the sum e+g+s+u+y=4, 5 or 6; and
  wherein:
    when the sum e+g+s+u+y=4,
      $M^2$ represents a second metal atom selected from nickel, palladium, copper, iron, cobalt, rhodium, chromium, and manganese;
      e is selected from 0, 1, 2, 3, or 4; and
      s and u are each selected from 0, 1, 2, or 3;
    when the sum e+g+s+u+y=5,
      $M^2$ represents a second metal atom selected from iron, cobalt, ruthenium, rhodium, chromium, and manganese;
      e is selected from 0, 1, 2, 3, 4, or 5; and
      s and u are each selected from 0, 1, 2, 3, or 4; or
    when the sum e+g+s+u+y=6
      $M^2$ represents a second metal atom selected from copper, iron, cobalt, ruthenium, rhodium, chromium, and manganese;
      e is selected from 0, 1, 2, 3, 4, 5, or 6; and
      s and u are each selected from 0, 1, 2, 3, 4, or 5; and
when α equals 1;
  $M^1$ represents a first metal atom selected from copper, iron, cobalt, ruthenium, rhodium, chromium, and manganese;
  β, b, c, k, p, e, f, g, s, u, x, and y each equal 0; a, h, and m are each selected from 0 or 1; d is selected from 0, 1, 2, 3, 4, 5, or 6; and r and t are each selected from 0, 1, 2, 3, 4, or 5; and the sum d+f+r+t+x=6.

When a first semi-(metal-pair) precursor complex and a second semi-(metal-pair) precursor complex are used to prepare a cationic metal-pair complex in the method of preparation of the cationic metal-pair complex of the present invention, that first semi-(metal-pair) precursor complex and that second semi-(metal-pair) precursor complex are related in the following ways:

the sum of "m" of said first semi-(metal pair) complex+"p" of said second semi-(metal pair) complex is selected from 1 or 2;
when α=x=1 for the first semi-(metal pair) complex, at least one second ligand of the second semi-(metal pair) complex (β=1, y=0) has at least one donor site available to fill a metal coordination site vacated by the leaving group Y; and, similarly,
when β=y=1 for the first semi-(metal pair) complex, at least one first ligand of the second semi-(metal pair) complex (α=1, x=0) has at least one donor site available to replace Y.

A "replacement moiety" is any moiety capable of becoming any of the following: first ligand, second ligand, first hydrocarbyl-containing radical, second hydrocarbyl-containing radical, first labile ligand, second labile ligand, and bridging moiety. A "replacement moiety" is capable of replacing a leaving group during or after removal of that leaving group from a full-(metal pair) precursor comple or a first semi-(metal pair) precursor complex.

The term "ethylenically unsaturated monomer" refers to a molecule having one or more carbon-carbon double bonds, and capable of insertion addition polymerization. The term "monoethylenically unsaturated monomer" refers to an ethylenically unsaturated monomer having one carbon-carbon double bond capable of insertion addition polymerization. The term "multiethylenically unsaturated monomer" refers to an ethylenically unsaturated monomer having two or more carbon-carbon double bonds capable of insertion addition polymerization.

The term "non-polar olefinic monomer" (alternatively "non-polar olefin") refers to an ethylenically unsaturated monomer consisting exclusively of hydrogen and carbon atoms. The non-polar olefinic monomers of the present invention are any non-polar olefinic monomers capable of being polymerized using the cationic metal-pair complex of the present invention to form "poly(non-polar olefin)s" or "poly[(polar olefin)-(non-polar olefin)]s".

The term "polar olefinic monomer" (alternatively "polar olefin") refers to an ethylenically unsaturated monomer including at least one atom other than carbon or hydrogen. The polar olefinic monomers of the present invention are any polar olefinic monomers capable of being polymerized using the cationic metal-pair complex of the present invention to form "poly(polar olefin)s" or "poly[(polar olefin)-(non-polar olefin)]s".

The term "(meth)acryl" refers to both "acryl" and "methacryl". For example, "butyl (meth)acrylate" refers to both "butyl acrylate" and "butyl methacrylate". "(Meth)acryl" type monomers are examples of the "polar olefinic monomer" of the present invention.

An "addition polymer" is a polymer capable of being prepared by addition polymerization, and selected from the group consisting of poly(non-polar olefin), poly(polar olefin), poly[(polar olefin)-(non-polar olefin)], and combinations thereof.

A "poly(non-polar olefin)" is a polymer comprising one or more non-polar olefinic monomers, as polymerized units. As such, a "poly(non-polar olefin)" may be a homopolymer or a copolymer, and the copolymer may be, for example, a random, alternating, or block copolymer.

A "poly(polar olefin)" is a polymer comprising, as polymerized units, one or more polar olefinic monomers. As such, a "poly(polar olefin)" may be a homopolymer or a copolymer, and the copolymer may be, for example, a random, alternating, or block copolymer.

A "poly[(polar olefin)-(non-polar olefin)]" is a copolymer comprising one or more non-polar olefinic monomers and one or more polar olefinic monomers, as polymerized units, and the copolymer may be, for example, a random, alternating, or block copolymer. The addition polymer of the present invention is a polymer selected from the group consisting of poly(non-polar olefin), poly(polar olefin), poly [(polar olefin)-(non-polar olefin)], and combinations thereof.

The following expressions describe the molecular weight of a collection of polymer chains "weight average molecular weight", "$M_w$," and the "number average molecular weight", "$M_n$". These are defined as follows:

$$M_w = \Sigma(W_i M_i)/\Sigma W_i = \Sigma(N_i M_i^2)/\Sigma N_i M_i$$

$$M_n = \Sigma W_i/\Sigma(W_i/M_i) = \Sigma(N_i M_i)/\Sigma N_i$$

where:
$M_i$=molar mass of $i^{th}$ component of distribution
$W_i$=weight of $i^{th}$ component of distribution
$N_i$=number of chains of $i^{th}$ component and the summations are over all the components in the distribution. $M_w$ and $M_n$ are typically computed from the MWD as measured by Gel Permeation Chromatography (see the Experimental Section). The value for "$M_w/M_n$" is referred to as the "MWD polydispersity".

The "average particle size" determined for a collection of polymer particles, varies somewhat according to method of determination (e.g., by DCP or BI-90, as described herein below), but is approximately, or identically, "the weight average particle size", "$d_w$", also described herein below.

Herein, the term "particle size distribution" and the acronym "PSD" are used interchangeably. Used herein, "PSD polydispersity" is a description of the distribution of particle sizes for the plural polymer particles of the invention. PSD polydispersity is calculated from the weight average particle size, $d_w$, and the number average particle size, $d_n$, according to the expressions:

$$PSD \text{ Polydispersity} = (d_w)/(d_n),$$

where $d_n = \Sigma n_i d_i / \Sigma n_i$ $d_w = \Sigma n_i d_i d_i / \Sigma n_i d_i$, and where $n_i$ is the number of particles having the particle size $d_i$ A "monodisperse" distribution (herein, MIWD or PSD) refers to a distribution having a polydispersity of exactly 1.

A "supercritical fluid" ("SCF") is a substance above its critical temperature and critical pressure (i.e., its "critical point"). For carbon dioxide, the critical temperature is 31° C. and the critical pressure is 1070 psi. Above the critical point of a fluid, further compression does not cause formation of a liquid (see *Chem. Rev.*, 1999, 99, pp. 565–602.

Each metal atom pair of the cationic metal-pair complex of the present invention includes a single "first metal atom" represented by the symbol "$M^1$" ("metal atom $M^1$") and a single "second metal atom" represented by the symbol "$M^2$" ("metal atom $M^2$"). The first metal atom of the cationic metal-pair complex has six (6) occupied coordination sites, and is a metal atom selected from: copper, iron, cobalt, ruthenium, rhodium, chromium, and manganese; or copper, iron, cobalt, and chromium. The second metal atom of the cationic metal-pair complex can have: four (4) occupied coordination sites; five (5) occupied coordination sites; or six (6) occupied coordination sites. When the second metal atom of the cationic metal-pair complex has four (4) occupied coordination sites, that second metal atom is a metal atom selected from: nickel, palladium, copper, iron, cobalt, rhodium, chromium, and manganese; nickel, palladium, copper, iron, and cobalt; or nickel and palladium. When the second metal atom of the cationic metal-pair complex has five (5) occupied coordination sites, that second metal atom is a metal atom selected from: iron, cobalt, ruthenium, rhodium, chromium, and manganese; or iron, cobalt, and chromium. When the second metal atom of the cationic metal-pair complex has six (6) occupied coordination sites, that second metal atom is a metal atom selected from: copper, iron, cobalt, ruthenium, rhodium, chromium, and manganese; or copper, iron, cobalt, and chromium.

Because the cationic metal-pair complex of the present invention is made from the precursor complex of the present invention, it follows that when a cationic complex is made from one or more precursor complexes, metal atoms $M^1$ and $M^2$ of a cationic metal-pair complex will be, respectively, the same as any metal atoms $M^1$ and $M^2$ of the precursor complex(es), from which that cationic metal-pair complex was made. It is further the case that when the precursor complex is a "full-(metal-pair) precursor complex", both $M^1$ and $M^2$ will be present in the precursor complex. When the precursor complex is either a "first semi-(metal-pair) precursor complex" or a "second semi-(metal-pair) precursor complex", a single metal atom, either $M^1$ or $M^2$ will be present. Therefore, the first metal atom of the precursor complex, has six (6) occupied coordination sites, and is a metal atom selected from copper, iron, cobalt, ruthenium, rhodium, chromium, and manganese; or copper, iron, cobalt, and chromium. The second metal atom of the precursor complex can have: four (4) occupied coordination sites; five (5) occupied coordination sites; or six (6) occupied coordination sites. When the second metal atom of the precursor complex has four (4) occupied coordination sites, that second metal atom is a metal atom selected from: nickel, palladium, copper, iron, cobalt, rhodium, chromium, and manganese; nickel, palladium, copper, iron, and cobalt; or nickel and palladium. When the second metal atom of the precursor complex has five (5) occupied coordination sites, that second metal atom is a metal atom selected from: iron, cobalt, ruthenium, rhodium, chromium, and manganese; or iron, cobalt, and chromium. When the second metal atom of the precursor complex has six (6) occupied coordination sites, that second metal atom is a metal atom selected from: copper, iron, cobalt, ruthenium, rhodium, chromium, and manganese; or copper, iron, cobalt, and chromium.

A precursor complex may be a full-(metal pair) precursor complex, a first semi-(metal pair) precursor complex, or a second semi-(metal pair) precursor complex. Both first metal atom, $M_1$, and second metal atom, $M^2$, are present in the full-(metal pair) precursor complex. In contrast, only first metal atom, $M_1$, is present in a first semi-(metal pair) precursor complex, and only second metal atom, $M^2$, is present in a second semi-(metal pair) precursor complex.

The combined molar percentage of first metal atom, $M_1$, and second metal atom, $M^2$, present in the cationic metal-pair complex of the present invention, based on the total of all $M_1$-type metal atoms and $M^2$-type metal atoms present in any catalyst complexes of the catalytic composition of the present invention, is: at least 25, at least 50, at least 75, at least 90, or at least 95; and no more than 100; no more than 99; or no more than 97, based on the total moles of $M^1$ and $M^2$ The "through-space internuclear distance" for a metal atom pair of the present invention is: at least 1.5 Angstroms (Å=0.0001 micron), at least 2 Å, at least 3 Å, or at least 4 Å; and no more than 20 Å, no more than 15 Å, no more than 10 Å, or no more than 6 Å.

Any monodentate or multidentate ligand may be a first ligand of set $L^1$ or a second ligand of set $L^2$ of the present invention, provided that constraints (e.g., electronic, steric, and other spatial constraints) which exist for the ligand in any given cationic metal-pair complex, or precursor complex allow that monodentate or multidentate ligand to participate in at least one coordination bond with the corresponding metal atom ($M^1$ for ligand set $L^1$; and $M^2$ for ligand set $L^2$) of a metal-atom pair.

When both set $L^1$ and set $L^2$ are present in the same cationic metal-pair complex or in the same precursor complex, the first and second ligands that are, respectively, members of those sets may be identical or different ligands within a given set (i.e., $L^1$, $L^2$), and the ligands of set $L^1$ may be the same or different from those of set $L^2$. First ligands and second ligands may be, independently, selected from the following non-exhaustive lists of ligand types wherein at least one atom selected from Group 14, 15, 16, and 17 participates in at least one coordination bond of the present invention.

Any multidentate ligand may also be a third ligand of set $L^3$ of the present invention, provided that constraints (e.g., electronic, steric, and other spatial constraints) which obtain for the ligand in any specific cationic metal-pair complex, or full-(metal pair) precursor complex allow that multidentate ligand to simultaneously participate in at least one coordination bond with each of the metals of a metal-atom pair of that complex.

Similarly, lists of labile ligand, hemi-labile ligand, anionic hydrocarbyl containing radical, activator, weakly coordinating anion, diluents, and monomer types, as well as specific example, provided herein are meant to be illustrative and not exhaustive. Further, the ability of a given labile ligand, hemi-labile ligand, or anionic hydrocarbyl containing radical to form a coordination bond with one, or both, metal atoms of a metal atoms pair of a particular cationic metal-pair complex or precursor complex of the present invention, will depend upon the constraints (e.g., electronic, steric, and other spatial constraints) which exist for that labile ligand, hemi-labile ligand, or anionic hydrocarbyl containing radical.

When mono- and multi-dentate ligands are indicated structurally or by chemical name herein, usage may be made of the designation of one or more substituents on a ligand as an "R-group" indicated by a capital "R", with or without a superscript. Although such notation, common in the art of organometallic chemistry and chemistry in general, is retained herein for describing substituents of ligands, it is understood, herein, that these "R-group" notations do not refer to the first or second anionic hydrocarbyl containing radicals of set $R^1$ and set $R^2$, respectively, of the cationic complex, or of the precursor complex, of the present invention. Similarly, it is understood that any R-group notations used herein to describe, for example, substituents of labile ligands, or substituents of hemi-labile ligands, or substituents of activators, or substituents of weakly coordinating anions, or substituents of ethylenically unsaturated monomers, do not refer to the first or second anionic hydrocarbyl containing radicals of set $R^1$ and set $R^2$, respectively, of the present invention.

Representative neutral electron donor ligands include amines, pyridines, organophosphorus containing compounds, and arsines and stibines, of the formula: $E(R^3)_3$, wherein E is arsenic or antimony, and $R^3$ is independently selected from hydrogen, linear and branched C1–C10 alkyl, C5–C10 cycloalkyl, linear and branched C1–C10 alkoxy, allyl, linear and branched C2–C10 alkenyl, C6–C12 aryl, C6–C12 aryloxy, C6–C12 arylsufides (e.g., PhS), C7–C18 aralkyl, cyclic ethers and thioethers, tri(linear and branched C1–C10 alkyl)silyl, tri(C6–C2 aryl)silyl, tri(linear and branched C1–C10 alkoxy)silyl, triaryloxysilyl, tri(linear and branched C1–C10 alkyl)siloxy, and tri(C6–C12 aryl)siloxy, each of the foregoing substituents can be optionally substituted with linear or branched C1–C5 alkyl, linear or branched C1–C5 haloalkyl, C1–C5 alkoxy, halogen, and combinations thereof.

Representative pyridines include pyridine, lutidine (including 2,3-; 2,4-; 2,5-; 2,6-; 3,4-; and 3,5-substituted), picoline (including 2-, 3-, or 4-substituted), 2,6-di-t-butylpyridine, and 2,4-di-t-butylpyridine.

Representative arsines include triphenylarsine, triethylarsine, and triethoxysilylarsine.

Representative stibines include triphenylstibine and trithiophenylstibine.

Suitable amine ligands can be selected from amines of the formula $N(R^4)_3$, wherein $R^4$ independently represents hydrogen, linear and branched $C_1$–$C_{20}$ alkyl, linear and branched $C_1$–$C_{20}$ haloalkyl, substituted and unsubstituted $C_3$–$C_{20}$ cycloalkyl, substituted and unsubstituted $C_6$–$C_{18}$ aryl, and substituted and unsubstituted $C_7$–$C_{18}$ aralkyl. When substituted, the cycloalkyl, aryl and aralkyl groups can be monosubstituted or multisubstituted, wherein the substituents are independently selected from hydrogen, linear and branched $C_1$–$C_{12}$ alkyl, linear and branched $C_1$–$C_5$ haloalkyl, linear and branched $C_1$–$C_5$ alkoxy, $C_6$–$C_{12}$ aryl, and halogen selected from chlorine, bromine, and fluorine. Representative amines include but are not limited to ethylamine, triethylamine, diisopropylamine, tributylamine, N,N-dimethylaniline, N,N-dimethyl-4-t-butylaniline, N,N-dimethyl-4-t-octylaniline, and N,N-dimethyl-4-hexadecylaniline.

The organophosphorus containing ligands include phosphines, phosphites, phosphonites, phosphinites and phosphorus containing compounds of the formula: $P(R^3)_g[X'(R^3)h]_{3-g}$, wherein X' is oxygen, nitrogen, or silicon, $R^3$ is as defined above and each $R^3$ substituent is independent of the other, g is 0, 1, 2, or 3, and h is 1, 2, or 3, with the proviso that when X' is a silicon atom, h is 3, when X' is an oxygen atom h is 1, and when X' is a nitrogen atom, h is 2. When g is 0 and X' is oxygen, any two or 3 of $R^3$ can be taken together with the oxygen atoms to which they are attached to form a cyclic moiety. When g is 3 any two of R3 can be taken together with the phosphorus atom to which they are attached to represent a phosphacycle.

Illustrative phosphine ligands include, but are not limited to trimethylphosphine, triphenylphosphine, tri(trifluoromethylphenyl)phosphine, allyldiphenylphosphine, tris(trimethylsilyl)phosphine, and tris(pentafluorophenyl)phosphine.

The phosphine ligands can also be selected from phosphine compounds that are water soluble thereby imparting the resulting cationic metal-pair complexes with solubility in aqueous media. Illustrative phosphines of this type include but are not limited to ionic or ionizable substituted phosphines such as 4-(diphenylphosphine)benzoic acid, sodium 2-(dicyclohexylphosphino)ethanesulfonate, and 2-(dicyclohexylphosphino)-N,N,N-trimethylethanaminium iodide.

Illustrative phosphite ligands include triethylphosphite, dicyclohexylphosphite, and tri(hexafluoroisopropyl)phosphite.

Illustrative phosphinite ligands include methyl diphenylphosphinite and ethyl diphenylphosphinite.

Illustrative phosphonite ligands include diphenyl phenylphosphonite and diethyl phenylphosphonite.

The multidentate ligands of the present invention include multidentate ligands containing identical or different donor atoms selected from Group 14, 15, 16, and 17 atoms. The substituents covalently bonded to those donor atoms selected from Group 14, 15, 16, and 17 atoms may be any of those bound to the Group-14, 15, 16, and 17 atoms of the monodentate ligands of the present invention.

Illustrative bidentate phosphine ligands of the present invention include (R)-(+)-2,2'-Bis(diphenylphosphino)-1,1'-binaphthy, and 1,2-bis(diphenylphosphino)ethane.

Additional neutral electron ligands useful in the present invention are disclosed in U.S. Pat. No. 6,455,650.

N-heterocyclic carbene ligands, suitable for use with the present invention include saturated and unsaturated substituted and unsubstituted imidazolidine having a structure according to one of structures (A)–(D):

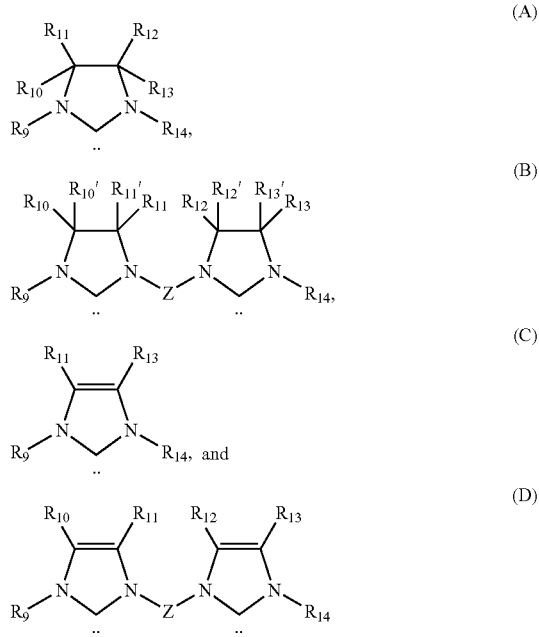

wherein $R^9, R^{10}, R^{10'}, R^{11}, R^{11'}, R^{12}, R^{12'}, R^{13}, R^{13'}$ and $R^{14}$ are each independently a hydrogen or a substituted or unsubstituted substituent selected from C1–C20 alkyl, C2–C20 alkenyl, C2–C20 alkynyl, aryl, C1–C20 carboxylate, C1–C20 alkoxy, C2–C20 alkenyloxy, C2–C20 alkynyloxy, aryloxy, C2–C20 alkoxycarbonyl, C1–C20 alkylthio, C1–C20 alkylsulfonyl, C1–C20 alkylsulfinyl, and silyl; and connecting group Z may be selected from C1–C20 alkyl, aryl, C1–C20 carboxylate, C1–C20 alkoxy, C2–C20 alkenyloxy, C2–C20 alkynyloxy, aryloxy, C2–C20 alkoxycarbonyl, C1–C20 alkylthio, C1–C20 alkylsulfonyl, C1–C20 alkylsulfinyl, and silyl.

In one aspect, at least one of the $R^9, R^{10}, R^{10'}, R^{11}, R^{11'}, R^{12}, R^{12'}, R^{13}, R^{13'}$ and $R^{14}$ substituent groups is substituted with at least one moiety selected from C1–C10 alkyl, C1–C10 alkoxy, and aryl which in turn may each be further substituted with at least one group selected from a halogen, a C1–C5 alkyl, C1–C5 alkoxy and phenyl.

In another aspect, at least one of the $R^9, R^{10}, R^{10'}, R^1, R^{11'}, R^{12}, R^{12'}, R^{13}, R^{13'}$ and $R^{14}$ substituent groups further includes at least one functional group. Functional groups suitable for use in these substituent groups include, for example, hydroxyl, thiol, alcohol, sulfonic acid, phosphine, thioether, ketone, aldehyde, ester, ether, amine, imine, amide, imide, imido, nitro, carboxylic acid, disulfide, carbonate, isocyanate, carbodiimide, carboalkoxy, carbamate, acetal, ketal, boronate, cyano, cyanohydrin, hydrazine, oxime, hydrazide, enamine, sulfone, sulfide, sulfenyl and halogen.

In another aspect, $R^{10}, R^{10'}, R^{11}, R^{11'}, R^{12}, R^{12'}, R^{13}, R^{13'}$ are each independently selected from hydrogen, methyl, aralkyl and aryl and $R^9$ and $R^{14}$ are each independently selected from substituted or unsubstituted C1–C10 alkyl, C1–C10 cycloalkyl, C2–C10 alkenyl, aralkyl and aryl.

In another aspect, $R^{10}, R^{10'}, R^{11}, R^{11'}, R^{12}, R^{12'}, R^{13}, R^{13'}$ are each hydrogen and $R^9$ and $R^{14}$ substituents are each independently substituted or unsubstituted and are selected from phenyl, vinyl, methyl, isopropyl, tert-butyl, neopentyl and benzyl.

In another aspect, $R^{10}, R^{10'}, R^{11}, R^{11'}, R^{12}, R^{12'}, R^{13}, R^{13'}$ are each hydrogen and $R^9$ and $R^{14}$ substituents are each independently substituted or unsubstituted and are selected from phenyl, vinyl, methyl, isopropyl, tert-butyl, neopentyl and benzyl; and wherein at least one of the substituents $R^9$ and $R^{14}$ is substituted with at least one moiety selected from C1–C5 alkyl, C1–C5 alkoxy, phenyl and a functional group. Functional groups suitable for use with this aspect of the present invention include, for example, hydroxyl, thiol, thioether, ketone, aldehyde, ester, ether, amine, imine, amide, nitro, carboxylic acid, disulfide, carbonate, isocyanate, carbodiimide, carboalkoxy, carbamate and halogen.

In another aspect, $R^9$ and $R^{14}$ are each independently substituted or unsubstituted aryl.

In another aspect, $R^9, R^{10}, R^{10'}, R^{11}, R^{11'}, R^{12}, R^{12'}, R^{13}, R^{13'}$ and $R^{14}$ are linked to form a substituted or unsubstituted, saturated or unsaturated ring structure.

In another aspect, $R^9, R^{10}, R^{10'}, R^{11}, R^{11'}, R^{12}, R^{12'}, R^{13}, R^{13'}$ and $R^{14}$ are linked to form a substituted or unsubstituted, saturated or unsaturated ring structure, wherein the ring structure contains substituents selected from hydrogen, methyl and substituted or unsubstituted aryl, aralkyl, C2–C10 alkenyl, C1–C10 cycloalkyl and C1–C10 alkyl.

In another aspect, $R^9, R^{10}, R^{10'}, R^{11}, R^{11'}, R^{12}, R^{12'}, R^{13}, R^{13'}$ and $R^{14}$ are linked to form a substituted or unsubstituted, saturated or unsaturated ring structure, wherein the ring structure contains substituents selected from alkoxy, aryloxy and functional groups selected from hydroxyl, thiol, thioether, ketone, aldehyde, ester, ether, amine, imine, amide, nitro, carboxylic acid, disulfide, carbonate, isocyanate, carbodiimide, carboalkoxy, carbamate and halogen.

In another aspect, $R^{10}, R^{10'}, R^{13}$ and $R^{13'}$ are each independently a hydrogen, a phenyl or together form a cycloalkyl or an aryl optionally substituted with at least one moiety selected from C1–C10 alkyl, C1–C10 alkoxy, aryl and a functional group selected from hydroxyl, thiol, thioether, ketone, aldehyde, ester, ether, amine, imine, amide, nitro, carboxylic acid, disulfide, carbonate, isocyanate, carbodiimide, carboalkoxy, carbamate, and halogen; and $R^9$ and $R^{14}$ are each independently C1–C10 alkyl or aryl optionally substituted with C1–C5 alkyl, C1–C5 alkoxy, aryl or a functional group selected from hydroxyl, thiol, thioether, ketone, aldehyde, ester, ether, amine, imine, amide, nitro, carboxylic acid, disulfide, carbonate, isocyanate, carbodiimide, carboalkoxy, carbamate and halogen.

In another aspect, $R^{10}$, $R^{10'}$, $R^{14}$ and $R^{14'}$ are both hydrogen or phenyl, or together form a cycloalkyl group; if present, $R^{11}$, $R^{11'}$, $R^{12}$ and $R^{12'}$ are each hydrogen; and $R^9$ and $R^{14}$ are each selected from substituted or unsubstituted aryl.

In another aspect, $R^9$ and $R^{14}$ are independently of structure (E):

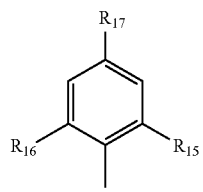

(E)

wherein $R^{15}$, $R^{16}$, and $R^{17}$ are each independently hydrogen, $C_1$–$C10$ alkyl, C1–C10 alkoxy, aryl or a functional group selected from hydroxyl, thiol, thioether, ketone, aldehyde, ester, ether, amine, imine, amide, nitro, carboxylic acid, disulfide, carbonate, isocyanate, carbodimide, carboalkoxy, carbamate and halogen.

In another aspect, $R^9$ and $R^{14}$ are independently of structure (E), wherein $R^{15}$, $R^{16}$, and $R^{17}$ are each independently selected from hydrogen, methyl, ethyl, propyl, isopropyl, hydroxyl and halogen.

In another aspect, $R^9$ and $R^{14}$ are independently of structure (E), wherein $R^{15}$, $R^{16}$, and $R^{17}$ are each methyl.

In another aspect, the connecting group, Z, may be substituted with one or more moieties selected from C1–C10 alkyl, C1–C10 alkoxy and aryl; which in turn may each be further substituted with one or more groups selected from a halogen, a C1–C5 alkyl, C1–C5 alkoxy and phenyl.

In another aspect, the connecting group, Z, may further include one or more functional groups. Functional groups suitable for use in connecting group, Z, include, for example, hydroxyl, thiol, alcohol, sulfonic acid, phosphine, thioether, ketone, aldehyde, ester, ether, amine, imine, amide, imide, imido, nitro, carboxylic acid, disulfide, carbonate, isocyanate, carbodiimide, carboalkoxy, carbamate, acetal, ketal, boronate, cyano, cyanohydrin, hydrazine, oxime, hydrazide, enamine, sulfone, sulfide, sulfenyl and halogen.

Additional moieties suitable as bridging moieties include methylenes, alkylenes, halides, and pseudohalides. The methylenes (i.e., $CR_2$) and alkylenes (i.e., $(CR_2)n$, n=1–24), may have R-groups which, independently, may be C1–C20 alkyl or branched alkyl, mono and multi-ring aryl. Further, any of the carbons of these methylenes and alkylenes may be further substituted with functional groups. Halides and pseudohalides may be and first ligand, second ligands, or bridging moieties. Suitable halides include, for example, fluoride, chloride, bromide, and iodide. Suitable pseudohalides include, for example, cyanide, isocyanide, alkoxides, thioalkoxides, amines, and phosphides. Hydride may further be a bridging moiety.

Hemilabile ligands contain at least two different types of donor sites, wherein at least one donor site is capable of acting as a "non-labile donor site", and at least one donor site is capable of acting as a "labile donor site". Typically, a labile donor site is easily displaced from a coordination bond with a metal by, for example, the donor sites of labile ligands (e.g., solvent molecules) and by ethylenically unsaturated monomer. It, therefore, follows that a labile donor site of a hemi-labile ligand is easily displaced strongly coordinating donor sites of strongly coordinating ligands. In contrast, a non-labile donor site is difficult to displace from a coordination bond with a metal. Therefore, when a hemilabile ligand is attached to a metal pair of a cationic metal-pair complex or precursor complex of the present invention, the formalism for assigning subscripts to any cationic metal-pair complex formula or precursor complex formula is as follows: when a hemilabile ligand is bound to a single metal atom of a metal atom pair, any coordination bonds formed by any of the donor sites (labile or non-labile) of that hemilabile ligand will be treated as coordination bonds of first or second ligands; when a hemilabile ligand is bound to both metal atoms of a metal atom pair, any coordination bonds formed by any of the donor sites (labile or non-labile) of that hemilabile ligand will be treated as coordination bonds of a bridging moiety. Further description of hemilabile ligands may be found in: Braunstein, P.; Naud, F. *Angew. Chem. Int. Ed.* 2001, 40, 680; Slone, C. S.; Weinberger, D. A.; Mirkin, C. A. *Prog. Inorg. Chem.* 1999, 48, 233, and the hemilabile ligands of the present invention include those described therein.

One skilled in the art of organometallic chemistry will recognize that the hemilabile ligands of the present invention may be any hemilabile ligand. For illustrative purposes, a non-exhaustive list of hemi-labile phosphine ligands is described. Similar lists exist for other Group 14, 15, 16, and 17 atom containing ligands. By hemilabile phosphine ligand is meant a phosphine ligand containing an additional heteroatom substituent, (e.g., oxygen or sulfur), capable of weakly complexing a metal atom. Included in the hemilabile phosphine ligands of the present invention are hemilabile phosphine ligands represented by the formula P(R24)2Q wherein R24 independently represents linear and branched (C1–C12) alkyl, cycloalkyl and (C6–C14) aryl and substituted aryl, and Q represents an organic moiety containing a heteroatom, selected from phosphorous, oxygen, and sulfur and combinations thereof. Examples of the Q substituent include but are not limited to -dibenzothiophene, ortho-alkoxyphenyl-, ortho-alkoxycarbonylphenyl-, wherein the alkoxy group is linear or branched (C1–C5) alkoxy; —(CH2)qS(=O)C6H5, —(CH2)qSC6H5, —(CH2)qP(=O)(C6H5)2, —(CH2)qP(=S)(C6H5)2, wherein q is 2 or 3. Example of ligands excluded from this class of hemiligands are the strongly chelating ligands, e.g., the diphosphines such as diphenylphosphinoethane and diphenylphosphinopropane. Specific examples of suitable hemilabile phosphine ligands are illustrated below:

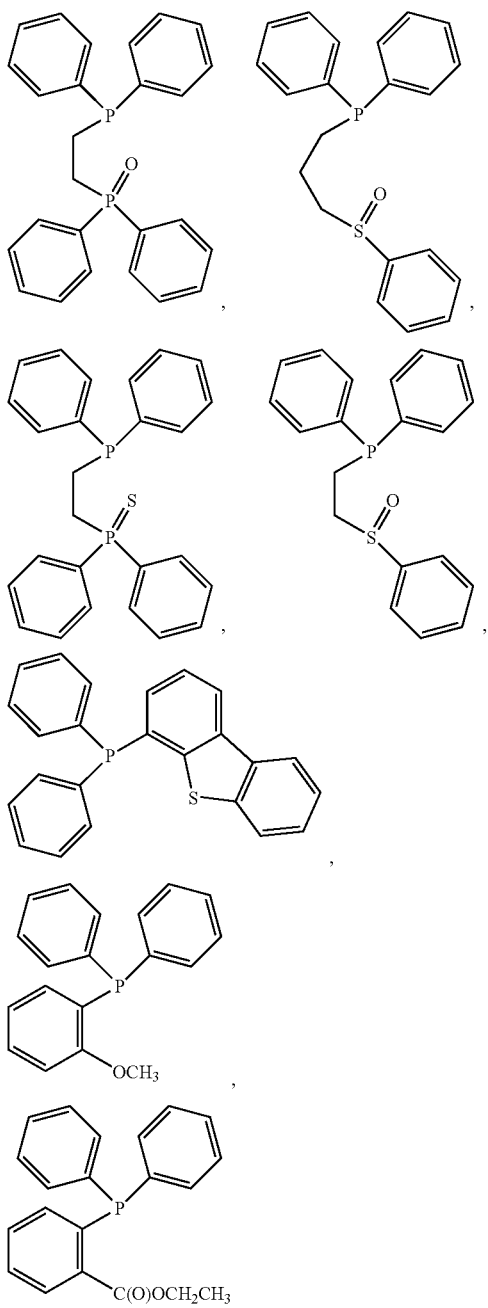

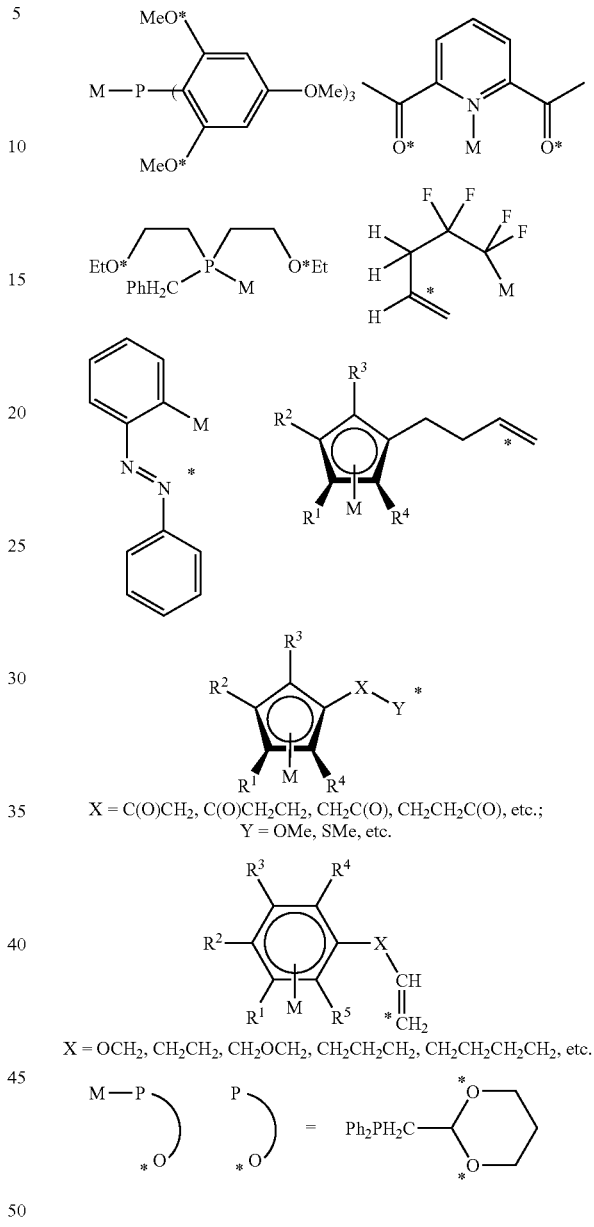

The following hemilabile ligands are shown coordinated to a metal atom, M, through a non-labile donor site. Labile donor sites, available for weak bonding to the same metal atom, or another metal atom are indicated by asterisk.

A non-exhaustive list of ligands further illustrating bridging moieties of the present invention, is found in Table I. These and other suitable bridging moieties are disclosed in Gavrilova, A. L.; Bosnich, B. *Chem. Rev.* 2004, 104, 349.

TABLE I

Examples of bridging moieties of the present invention.

| Bridging unit name | Bridging unit | Metal binding mode |
|---|---|---|
| Halide, Pseudohalide | $\overset{\ominus}{X}$<br>X = F, Cl, Br, I, NCO, NCS, $N_3$, etc. | $M^1 \overset{X}{\diagdown} M^2$<br>X = F, Cl, Br, I, NCO, NCS, $N_3$, etc. |

TABLE I-continued
Examples of bridging moieties of the present invention.
| Bridging unit name | Bridging unit | Metal binding mode |
|---|---|---|
| Methylene, (methylene)$_n$ | 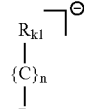 $n = 1, 2, 3, 4, \ldots, 24$ $CH_2, k = 1, \ldots, n$ | 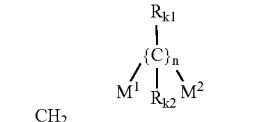 $n = 1, 2, 3, 4, \ldots, 24$ $k = 1, \ldots, n$ |
| Carboxylate |  | 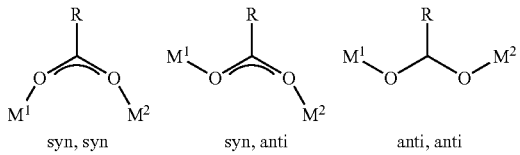 syn, syn    syn, anti    anti, anti |
| Formamidinate | 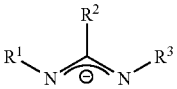 | 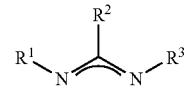 syn, syn |
| Pyrazolate | 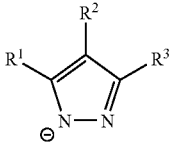 | 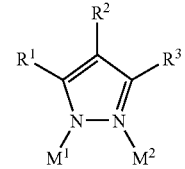 |
| Triazolate | 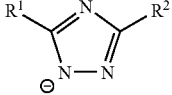 | 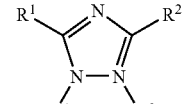 |
| Oxadiazole | 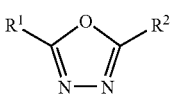 | 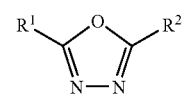 |
| Triadiazole | 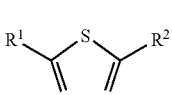 | 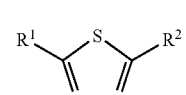 |
| Pyridazine and Phthalazine | 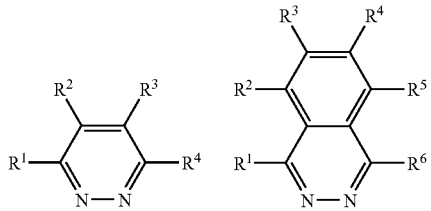 | 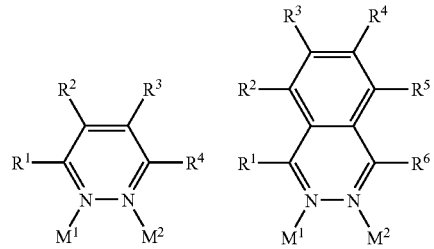 |

TABLE I-continued
Examples of bridging moieties of the present invention.
| Bridging unit name | Bridging unit | Metal binding mode |
|---|---|---|
| 1,8-Naphthyridine | | |
| Phenolate, Alkoxide | | |
| Thiophenolate | | |
| Disulfide | | |
| Phosphide | | |
An additional illustrative example of a bridging moiety is "NON":
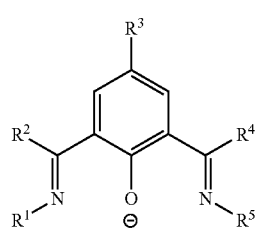
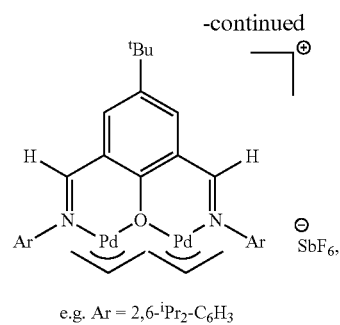
e.g. Ar = 2,6-$^i$Pr$_2$-C$_6$H$_3$ depicted here in a cationic metal-pair complex, in which both, $M^1$ and $M^2$ are palladium.

Any monodentate or multidentate labile ligand may be a first labile ligand of set $S^1$ or a second ligand of set $S^2$ of the present invention, provided that constraints (e.g., electronic, steric, and other spatial constraints) which exist for that labile ligand in any given cationic metal-pair complex, or precursor complex allow that monodentate or multidentate ligand to participate in at least one coordination bond with the corresponding metal atom ($M^1$ for labile ligand set $S^1$; and $M^2$ for labile ligand set $S^2$) of a metal-atom pair. Further, any multidentate labile ligand may simultaneously participate in at least one coordination bond of each metal atom in a metal atom pair. In such case, the labile ligand is acting as a bridging moiety, so the formalism for assigning subscripts to any cationic metal-pair complex formula or precursor complex formula is as follows: when a labile ligand is bound to both metal atoms of a metal atom pair, any coordination bonds formed by labile donor sites of that labile ligand will be treated as coordination bonds of a bridging moiety (ie., of set $L^3$).

A non-exhaustive list of the labile neutral electron donor ligands of the present invention includes solvents such as methylene chloride, CHCl3, ClCH2CH2Cl, acrylonitrile, tetrahydrofuran, toluene, benzene, chlorobenzene, and polar monomers, as well as any other diluents typified by those found in the list of diluents, herein, which are able to donate electron density to a metal atom coordination site to form a coordination bond. Further, molecules such as, for example, dioxane, crown ethers, other polyethers, and cyclodextrins typify labile ligands capable of bridging between the metal atoms of a metal atom pair, and, where electronic, steric, and special constraints permit, between, or among metal atom pairs. One skilled in the art of organometallic chemisty will understand that a labile ligand may participate in a coordination bond with a one or both metal atoms of a metal atom pair. Alternatively, a labile ligand may be more loosely associated as part of a solvation sphere which may, in some cases, surround any of the cationic metal-pair complexes or precursor complexes of the present invention. According to common practice in the art, these more loosely associated molecules of the solvation sphere are not explicitly indicated in the cationic metal-pair complex formula or the precursor complex formula.

$R^1$ and $R^2$ represent anionic hydrocarbyl containing radicals, and appear in the formulae for the precursor complexes and for the cationic metal-pair complex of the present invention. When both $R^1$ and $R^2$ are present in the same precursor complex or in the same cationic metal-pair complex, they may be identical or different entities $R^1$ and $R^2$ may be, independently, selected from the following non-exhaustive lists of types of anionic hydrocarbyl containing radical and of specific examples of anionic hydrocarbyl containing radical.

First and second anionic hydrocarbyl containing radicals include, but are not limited to, hydrogen, linear and branched C1–C20 alkyl, C5–C10 cycloalkyl, linear and branched C2–C20 alkenyl, C6–C15 cycloalkenyl, allylic and methallylic ligands, crotyl ligands, or canonical forms thereof, C6–C30 aryl, C6–C30 heteroatom containing aryl, and C7–C30 aralkyl, each of the foregoing groups can be optionally substituted with hydrocarbyl containing and/or heteroatom substituents preferably selected from linear or branched C1–C5 alkyl, linear or branched C1–C5 haloalkyl, linear or branched C2–C5 alkenyl and haloalkenyl, halogen, sulfur, oxygen, nitrogen, phosphorus, and phenyl optionally substituted with linear or branched C 1–C5 alkyl, linear or branched C1–C5 haloalkyl, and halogen. $R^1$ and $R^2$ also represent anionic hydrocarbyl containing radicals of the formula R"C(O)O, R"C(O)CHC(O)R", R"C(O)S, R"C(S)O, R"C(S)S, R"O, and R" 2 N.

Additional representative examples of anionic ligands:

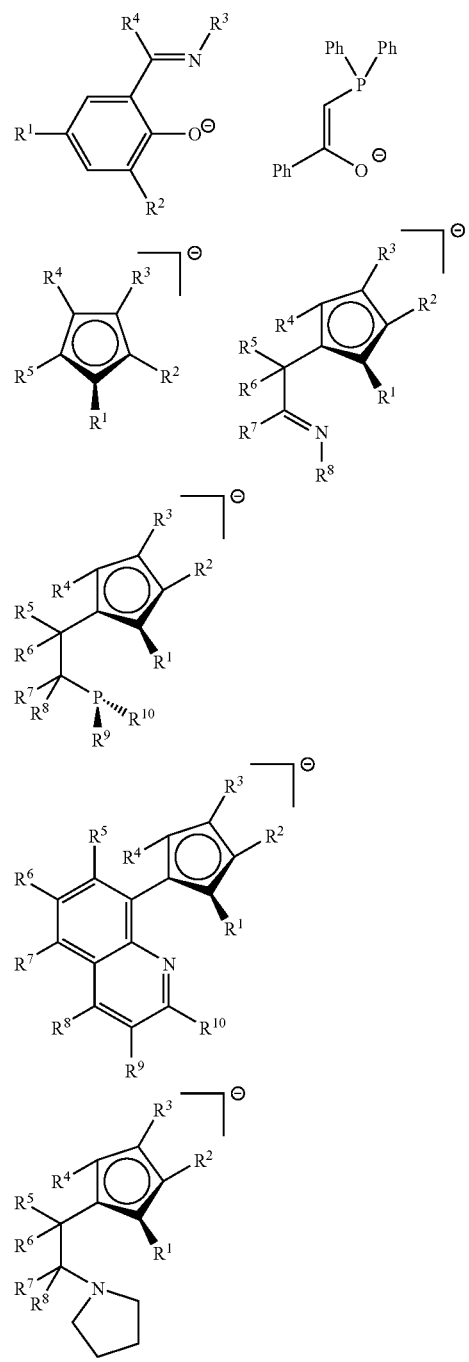

wherein the various R-groups may be: C1–C12 linear, branched, or cyclic and polycyclic alkyl; aryl or polycyclic aryl; or functional groups; and the alkyl and aryl groups may be further substituted with functional groups.

A "leaving group" ("Y") is capable of being removed from a precursor complex of the present invention by the action of an activator component. A leaving group (e.g., a halide or pseudohalide) may be bound to both metals or a single metal of a metal pair of a full-(metal pair) precursor complex, or bound to the single metal atom of a semi-(metal pair) precursor complex.

Additional examples of anionic hydrocarbyl containing ligands are disclosed in U.S. Pat. No. 6,455,650; R. G. Guy and B. L. Shaw, Advances in Inorganic Chemistry and Radiochemistry, Vol. 4, Academic Press Inc., New York, 1962; J. Birmingham, E. de Boer, M. L. H. Green, R. B. King, R. Köster, P. L. I. Nagy, G. N. Schrauzer, Advances in Organometallic Chemistry, Vol. 2, Academic Press Inc., New York, 1964; W. T. Dent, R. Long and A. J. Wilkinson, *J. Chem. Soc.* 1964 1585; and H. C. Volger, *Rec. Trav. Chim. Pay Bas* 1969 88 225.

A "WCA" is a "weakly coordinating anion". The weakly coordinating anion is an anion that is only weakly coordinated to the cationic metal-pair complex. The WCA is sufficiently labile to be displaced by a neutral Lewis base, solvent or monomer. More specifically, the WCA functions as a stabilizing anion to the cationic metal-pair complex and does not transfer to the cationic metal-pair complex to form a neutral product. The WCA is relatively inert in that it is non-oxidative, non-reducing, and non-nucleophilic.

The weakly coordinating anion can be selected, for example, from borates and aluminates, boratobenzene anions, carborane halocarborane anions, antimony halide anions (e.g., SbF6), phosphorus halide anions (e.g., PF6), and boron halide anions (e.g., BF4). The borate and aluminate weakly coordinating anions are represented by the structures II and III below:

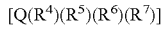   structure II

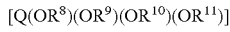   III wherein, in structure II, Q is boron or aluminum and $R^4$, $R^5$, $R^6$, and $R^7$ independently represent fluorine, linear and branched C1–C10 alkyl, linear and branched C1–C10 alkoxy, linear and branched C3–C5 haloalkenyl, linear and branched C3–C12 trialkylsiloxy, C18–C36 triarylsiloxy, substituted and unsubstituted C6–C30 aryl, and substituted and unsubstituted C6–C30 aryloxy groups wherein $R^4$ to $R^7$ can not all simultaneously represent alkoxy or aryloxy groups. When substituted the aryl groups can be monosubstituted or multisubstituted, wherein the substituents are independently selected from linear and branched C1–C5 alkyl, linear and branched C1–C5 alkoxy, linear and branched C1–C5 haloalkyl, linear and branched C1–C5 haloalkoxy, linear and branched C1–C12 trialkylsilyl, C6–C18 triarylsilyl, and halogen selected from chlorine, bromine, and fluorine, preferably fluorine. Representative borate anions under Structure II include but are not limited to tetrakis(pentafluorophenyl)borate, tetrakis(3,5-bis(trifluoromethyl)phenyl)borate, tetrakis(2-fluorophenyl) borate, tetrakis(3-fluorophenyl)borate, tetrakis(4-fluorophenyl)borate, tetrakis(3,5-difluorophenyl)borate, tetrakis(2,3,4,5-tetrafluorophenyl) borate, tetrakis(3,4,5,6-tetrafluorophenyl)borate, tetrakis(3,4,5-trifluorophenyl)borate, methyltris(perfluorophenyl)borate, ethyltris(perfluorophenyl)borate, phenyltris(perfluorophenyl)borate, tetrakis(1,2,2-trifluoroethylenyl)borate, tetrakis(4-tri-1-propylsilyltetrafluorophenyl)borate, tetrakis(4-dimethyl-tert-butylsilyltetrafluorophenyl)borate, (triphenylsiloxy)tris(pentafluorophenyl)borate, (octyloxy)tris(pentafluorophenyl)borate, tetrakis[3,5-bis[1-methoxy-2,2,2-trifluoro-1-(trifluoromethyl)ethyl]phenyl] borate, tetrakis[3-[1-methoxy-2,2,2-trifluoro-1-(trifluoromethyl)ethyl]ethyl]-5-(trifluoromethyl)phenyl]borate, and tetrakis [3-[2,2,2-trifluoro-1-(2,2,2-trifluoroethoxy)-1-(trifluoromethyl)ethyl]-5-(trifluoromethyl) phenyl]borate.

Representative aluminate anions under Structure II include but are not limited to tetrakis(pentafluorophenyl) aluminate, tris(perfluorobiphenyl)fluoroaluminate, (octyloxy)tris(pentafluorophenyl)aluminate, tetrakis(3,5-bis(trifluoromethyl)phenyl)aluminate, and methyltris (pentafluorophenyl)aluminate.

In Structure III Q is boron or aluminum, $R^8$, $R^9$, $R^{10}$, and $R^{11}$ independently represent linear and branched C1–C10 alkyl, linear and branched C1–C10 haloalkyl, C2–C10 haloalkenyl, substituted and unsubstituted C6–C30 aryl, and substituted and unsubstituted C7–C30 aralkyl groups, subject to the proviso that at least three of $R^8$ to $R^{11}$ must contain a halogen containing substituent. When substituted the aryl and aralkyl groups can be monosubstituted or multisubstituted, wherein the substituents are independently selected from linear and branched C1–C5 alkyl, linear and branched C1–C5 haloalkyl, linear and branched C1–C5 alkoxy, linear and branched C1–C10 haloalkoxy, and halogen selected from chlorine, bromine, and fluorine, preferably fluorine. The groups O $R^8$ and O $R^9$ can be taken together to form a chelating substituent represented by —O—R $R^{12}$—O—, wherein the oxygen atoms are bonded to Q and $R^{12}$ is a divalent radical selected from substituted and unsubstituted C6–C30 aryl and substituted and unsubstituted C7–C30 aralkyl. Preferably, the oxygen atoms are bonded, either directly or through an alkyl group, to the aromatic ring in the ortho or meta position. When substituted the aryl and aralkyl groups can be monosubstituted or multisubstituted, wherein the substituents are independently selected from linear and branched C1–C5 alkyl, linear and branched C1–C5 haloalkyl, linear and branched C1–C5 alkoxy, linear and branched C1–C10 haloalkoxy, and halogen selected from chlorine, bromine, and fluorine, preferably fluorine.

Representative borate and aluminate anions under Structure III include but are not limited to [B(OC(CF3)3)4]-, [B(OC(CF3)2(CH3))4]-, [B(OC(CF3)2H)4]-, [B(OC(CF3)(CH3)H)4]-, [Al(OC(CF3)2Ph)4]-, [B(OCH2(CF3)2)4]-, [Al(OC(CF3)2C6H4CH3)4]-, [Al(OC(CF3)3)4]-, [Al(OC(CF3)(CH3)H)4]-, [Al(OC(CF3)2H)4]-, [Al(OC(CF3)2C6H4-4-i-Pr)4]-, [Al(OC(CF3)2C6H4-4-t-butyl)4]-, [Al(OC(CF3)2C6H4-4-SiMe3)4]-, [Al(OC(CF3)2C6H4-4-Si-i-Pr3)4]-, [Al(OC(CF3)2C6H2-2,6-(CF3)2-4-Si-i-Pr3)4]-, [Al(OC(CF3)2C6H3-3,5-(CF3)2)4]-, [Al(OC(CF3)2C6H2-2,4,6-(CF3)3)4]-, and [Al(OC(CF3)2C6F5)4]-.

Representative boratobenzene anions include but are not limited to [1,4-dihydro-4-methyl-1-(pentafluorophenyl)]-2-borate, 4-(1,1-dimethyl)-1,2-dihydro-1-(pentafluorophenyl)-2-borate, 1-fluoro-1,2-dihydro-4-(pentafluorophenyl)-2-borate, and 1-[3,5-bis(trifluoromethyl)phenyl]-1,2-dihydro-4-(pentafluorophenyl)-2-borate.

The carborane and halocarborane anions useful as the weakly coordinating anion include but are not limited to CB11(CH3)12-, CB11H12-, 1-C2H5CB11H11, 1-Ph3SiCB11H11-, 1-CF3CB11H11-, 12-BrCB11H11-, 12-BrCB11H11-, 7,12-Br2CB11H10, 12-CB11H11-, 7,12-C12CB11H10-, 1-H-CB11F11-, 1-CH3-CB11F11-, 1-CF3-CB11F11-, 12-CB11H11F—, 7,12-CB11H11F12-, 7,9,12-CB11H11F3-, CB11H6Br6-, 6-CB9H9F—, 6,8-CB9H8F2-, 6,7,8-CB9H7F3-, 6,7,8,9-CB9H6F4-, 2,6,7,8,9-CB9H5F5-, CB9H5Br5-, CB11H6Cl6-, CB11H6F6-, CB11H6F6-, CB11H6I6-, CB11H6Br6-, 6,7,9,10,11,12-CB11H6F6-, 2,6,7,8,9,10-CB9H5F5-, 1-H-CB9F9-, 12-CB11H11 (C6H5)-, 1-C6F5-CB11H5Br6-, CB11Me12-, CB11(CF3)12-, Co(B9C2H11)2-, CB11(CH3)12-, CB11(C4H9)12-, CB11(C6H13)12-, Co(C2B9H11)2-, Co(Br3C2B9H8)2- and dodecahydro-1-carbadodecaborate. The weakly coordinating anion of the present invention further includes any of those disclosed in U.S. Pat. No. 6,455,650.

Illustrative, but non-limiting examples of the "activator component" of the present invention are disclosed in publications of: Chen and Marks, such as *Chem. Rev.* 2000 100, 1391–1434; Coates, such as *Chem. Rev.* 2000 100, 1223–1252; Resconi et al, such as *Chem. Rev.* 2000, 100, 1253–1346; Fink et al, such as *Chem. Rev.* 2000 100, 1377–1390; Alt and Koeppl, such as *Chem. Rev.* 2000 100, 1205–1222; and Hlatky, *Chem. Rev.* 2000 100, 1347–1376, the contents of which are usefully employed in accordance with the present invention. Activator components useful in the method of preparing the cationic metal-pair complex of the present invention, for example, include: aluminum alkyls such as $Al(C2H5)3$, $Al(CH2CH(CH3)2)3$, $Al(C3H7)3$, $Al((CH2)3CH3)3$, $Al((CH2)5CH3)3$, $Al(C6F5)3$, $Al(C2H5)2Cl$, $Al2(C2H5)3Cl2$, $AlCl3$; aluminoxanes such as methylaluminoxane (MAO), modified methyl aluminoxane (MMAO), isobutylaluminoxane, butylaluminoxane, heptylaluminoxane and methylbutylaluminoxane; and combinations thereof. Both stoichiometric and non-stoichiometric quantities of activator components are usefully employed in the present invention. Chemically and structurally useful aluminum compounds as well as other activator components of Group 13 elements would be apparent to those skilled in the art based on their respective chemical structures and activities in preparing cationic metal-pair complexes.

The activator component further comprises hydroxyaluminoxanes. Hydroxyaluminoxanes, and methods of preparing them, are disclosed in U.S. Pat. No. 6,160,145. The hydroxyaluminoxane has a hydroxyl group bonded to at least one of its aluminum atoms.

The alkyl aluminum compound used in forming the hydroxyaluminoxane reactant can be any suitable alkyl aluminum compound other than trimethylaluminum. Thus at least one alkyl group has two or more carbon atoms. Preferably each alkyl group in the alkyl aluminum compound has at least two carbon atoms. More preferably each alkyl group has in the range of 2 to about 24, and still more preferably in the range of 2 to about 16 carbon atoms. Most preferred are alkyl groups that have in the range of 2 to about 9 carbon atoms each. The alkyl groups can be cyclic (e.g., cycloalkyl, alkyl-substituted cycloalkyl, or cycloalkyl-substituted alkyl groups) or acyclic, linear or branched chain alkyl groups. Preferably the alkyl aluminum compound contains at least one, desirably at least two, and most preferably three branched chained alkyl groups in the molecule. Most preferably each alkyl group of the aluminum alkyl is a primary alkyl group, i.e., the alpha-carbon atom of each alkyl group carries two hydrogen atoms.

Suitable aluminum alkyl compounds which may be used to form the hydroxyaluminoxane reactant include dialkylaluminum hydrides and aluminum trialkyls. Examples of the dialkylaluminum hydrides include diethylaluminum hydride, dipropylaluminum hydride, diisobutylaluminum hydride, di(2,4,4-trimethylpentyl)aluminum hydride, di(2-ethylhexyl)aluminum hydride, di(2-butyloctyl)aluminum hydride, di(2,4,4,6,6-pentamethylheptyl)aluminum hydride, di(2-hexyldecyl)aluminum hydride, dicyclopropylcarbinylaluminum hydride, dicyclohexylaluminum hydride, dicyclopentylcarbinylaluminum hydride, and analogous dialkylaluminum hydrides. Examples of trialkylaluminum compounds which may be used to form the hydroxyaluminoxane include triethylaluminum, tripropylaluminum, tributylaluminum, tripentylaluminum, trihexylaluminum, triheptylaluminum, trioctylaluminum, and their higher straight chain homologs; triisobutylaluminum, tris(2,4,4-trimethylpentyl)aluminum, tri-2-ethylhexylaluminum, tris(2,4,4,6,6-pentamethylheptyl)aluminum, tris(2-butyloctyl)aluminum, tris(2-hexyldecyl)aluminum, tris(2-heptylundecyl)aluminum, and their higher branched chain homologs; tri(cyclohexylcarbinyl)aluminum, tri(2-cyclohexylethyl)aluminum and analogous cycloaliphatic aluminum trialkyls; and tri (pentafluoro)aluminum. Triisobutylaluminum has proven to be an especially desirable alkyl aluminum compound for producing a hydroxyaluminoxane. Hydroxyisobutylaluminoxane (HOIBAO) is a preferred hydroxyaluminoxane. The hydroxyisobutylaluminoxane is essentially devoid of unreacted triisobutylaluminum.

Useful activator components further include aluminoxane salt compositions (aluminoxinates) as disclosed in U.S. Pat. No. 5,922,631. Useful activator components still further include any of the liquid clathrate aluminoxanes disclosed in U.S. Pat. No. 5,670,682.

Activator components useful in the present invention further include organic borane compounds, inorganic borane compounds, and borate anions. Preferred examples of boron containing activator components employed in the method of preparing the cationic metal-pair complex of the present invention are trifluoroborane, triphenylborane, tris(4-fluorophenyl)borane, tris(3,5-difluorophenyl)borane, tris(4-fluoromethylphenyl)borane, tris(pentafluorophenyl)borane, tris(tolyl)borane, tris(3,5-dimethylphenyl)borane, tris(3,5-difluorophenyl)borane, tris(3,4,5-trifluorophenyl)borane, dimethylanilinium(pentafluorophenyl) borate, sodium[B{3, 5-(CF3)2C6F3 }4], [H(OEt2)2[B{3,5-(CF3)2C6F3}4]. Both stoichiometric and non-stoichiometric quantities of activators are usefully employed using triaryl carbenium tetraarylborates, N,N-dialkylanilinium salts such as N,N-dimethylanilinium tetra(pentafluorophenyl)borate, N,N-diethylanilinium tetra(phenyl)borate, N,N-2,4,6-pentamethylanilinium tetraphenylborate and chemically related Group 13 compounds; dialkyl ammonium salts such as di(i-propyl) ammonium tetra(pentafluorophenyl)borate, dicyclohexylammonium tetra(phenyl)boron and chemically related Group 13 compounds; triaryl phosphonium salts such as triphenylphosphonium tetraphenylborate, tri(methylphenyl) phosphonium tetra(phenyl)borate, tri(dimethylphenyl)phosphonium tetra(phenyl)borate and chemically related Group 13 compounds. Any complex anions or compounds forming such anions that exhibit an ability to abstract and activate the metal compounds would be within the scope of the "activator component" of the present invention. Chemically and structurally useful boron compounds would be apparent to those skilled in the art based on their respective chemical structures and activities in olefin polymerizations.

In the method of the present invention, the activator component is present in an amount of: at least 0.1 molar equivalent, at least 0.3 molar equivalent, at least 0.7 molar equivalent, or at least 1.0 molar equivalent, based on leaving group Y; and no more than 5,000 molar equivalent, no more than 500 molar equivalent, no more than 5 molar equivalent, or no more than 2 molar equivalents, based on leaving group Y.

The non-polar olefinic monomers of the present invention include, for example, unbranched aliphatic olefins having from 2 to 12 carbon atoms, branched aliphatic olefins having from 4 to 12 carbon atoms, unbranched and branched aliphatic α-olefins having from 2 to 12 carbon atoms, conjugated olefins-having 4 to 12 carbon atoms, aromatic olefins having from 8 to 20 carbons, unbranched and branched cycloolefins having 3 to 12 carbon atoms, unbranched and branched acetylenes having 2 to 12 carbon atoms, and combinations thereof. A non-exhaustive list of examples of non-polar olefinic monomers of the present invention includes ethylene, propene, 1-butene, 1-hexene, butadiene, 1,5-hexadiene, isoprene, styrene, alpha-methylstyrene, cyclopentene, cyclohexene, cyclohexadiene, norbornene, norbornadiene, cyclooctadiene, divinylbenzeite, trivinylbenzene, acetylene, diacetylene, alkynylbenzene, dialkynylbenzene, ethylene/1-butene, ethylene/isopropene, ethylene/1-hexene, ethylene/1-octene, ethylene/propene, ethylene/cyclopentene, ethylene/cyclohexene, ethylene/butadiene, ethylene/1,5-hexadiene, ethylene/styrene, ethylene/acetylene, propene/1-butene, propene/styrene, propene/butadiene, propylene/1-hexene, propene/acetylene, ethylene/propene/1-butene, ethylene/propene/1-hexene, ethylene/propene/1-octene, and various combinations thereof.

Polar olefinic monomers of the present invention include ethylenically unsaturated monomers having from 2 to 60 carbon atoms and at least one atom such as O, N, B, Al, S, P, Si, F, Cl, Br, and combinations thereof. These polar olefinic monomers include, for example: C1–C22 linear or branched chain alkyl (meth)acrylates, bornyl (meth)acrylate, and isobornyl (meth)acrylate; hydroxyethyl (meth)acrylate, hydroxypropyl (meth)acrylate; (meth)acrylamide or substituted (meth)acrylamides; epoxy containing (meth)acrylates such as glycidyl (meth)acrylate; styrene or substituted styrenes; butadiene; vinyl acetate or other vinyl ester; vinyl chloride; vinylidene chloride; vinylidene fluoride; N-butylaminoethyl (meth)acrylate, N,N-di(methyl)aminoethyl (meth)acrylate; monomers containing α,β-unsaturated carbonyl functional groups such as fumarate, maleate, cinnamate and crotonate; and (meth)acrylonitrile. Acid-functional methacrylic monomers include, for example, (meth)acrylic acid, itaconic acid, crotonic acid, phosphoethyl (meth)acrylate, sulfoethyl (meth)acrylate, 2-acrylamido-2-methyl-1-propanesulfonic acid, fumaric acid, maleic anhydride, monomethyl maleate, and maleic acid.

Polar olefinic monomers of the present invention further include: acrylic acid 5-oxo-tetrahydro-furan-3-yl ester, acrylic acid 1,1,2-trimethyl-propyl ester, acrylic acid 2-ethyl-1,3,3-trimethyl-bicyclo[2.2.1]hept-2-yl ester, acrylic acid 2-ethyl-adamantan-2-yl ester, acrylic acid 2-methyl-adamantan-2-yl ester, acrylic acid 4-hydroxy-adamantan-1-yl ester, acrylic acid 3-hydroxy-adamantan-1-yl ester, acrylic acid 5-hydroxy-2-methyl-adamantan-2-yl ester, 5H-Furan-2-one, 3-Methylene-dihydro-furan-2-one, acrylic acid 1,7,7-trimethyl-bicyclo[2.2.1]hept-2-yl ester, acrylic acid 1-methyl-cyclopentyl ester, acrylic acid 5-oxo-4-oxa-tricyclo[4.2.1.03,7]non-2-yl ester, acrylic acid 1,2,3,3-tetramethyl-bicyclo[2.2.1]hept-2-yl ester, acrylic acid tert-butyl ester, acrylic acid I-ethyl-cyclopentyl ester, acrylic acid 3-oxo-4-oxa-tricyclo[5.2.1.02,6]dec-8-yl ester, and acrylic acid 1-(2-oxo-tetrahydro-furan-3-yl)-ethyl ester.

Suitable fluorinated (meth)acrylic monomers useful in the present invention include, but are not limited to: fluoroalkyl (meth)acrylate; fluoroalkylsulfoamidoethyl (meth)acrylate; fluoroalkylatnidoethyl (meth)acrylate; fluoroalkyl (meth)acrylamide; fluoroalkylpropyl (meth)acrylate; fluoroalkylethyl poly(alkyleneoxide)-(meth)acrylate; fluoroalkylsulfoethyl (meth)acrylate; fluoroalkylethyl vinyl ether; fluoroalkylethyl poly(ethyleneoxide) vinyl ether; pentafluoro styrene; fluoroalkyl styrene; vinylidene fluoride; fluorinated α-olefins; perfluorobutadiene; 1-fluoroalkylperfluorobutadiene; co-H-perfluoroalkanediol di(meth)acrylate; and β-substituted fluoroalkyl (meth)acrylate. The fluoroalkyl groups used as substituents have from 1 to 20 carbon atoms and the fluoroalkyl groups may be mono-, di, tri, or tetra-fluorinated, or contain any number of fluoro-atoms, up to and including perfluorinated compositions.

Silicon containing polar olefinic monomers useful in the present invention include, for example, trimethoxysilylethyl (meth)acrylate and trimethoxysilylpropyl (meth)acrylate.

The terms "cyclic olefin,", "polycyclic", "polycyclicolefin," and "norbornene-type" monomer as used herein are interchangeable and mean that the monomer contains at least one norbornene moiety as follows:

wherein W''' is selected from the group including, but by no means limited to, an oxygen, a nitrogen with a hydrogen attached thereto, a nitrogen with a linear C1 to C10 alkyl grouping attached thereto, a nitrogen with a branched C1 to C10 alkyl grouping attached thereto, a sulfur and a methylene group of having the formula —(CH2)n'- wherein n' is an integer from 1 to 5.

Polycyclic monomers of the present invention include both polycyclic monomers that are non-polar monomers and polycyclic monomer that are polar monomer.

Polycyclic monomers suitable for use with the present invention include bicyclic monomers, for example, bicyclo[2.2.1]hept-2-ene also referred to as norbornene.

The term "norbornene-type monomer" as used herein and in the appended claims is meant to encompass norbornene, substituted norbornene, as well as any substituted and unsubstituted higher cyclic derivatives thereof, provided that the subject monomer contains at least one norbornene-type moiety or substituted norbornene-type moiety.

Norbornene-type monomers suitable for use with the present invention include substituted norbornene-type monomers and higher cyclic derivatives thereof that contain a pendant hydrocarbon group or a pendant functional substituent containing an oxygen atom.

Norbornene-type monomers suitable for use with the present invention may include norbornene-type or polycycloolefin monomers are represented by the structure below:

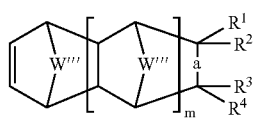

(A)

wherein each W''' is independently defined as above; "a" is a single or a double bond; $R^1$, $R^2$, $R^3$, and $R^4$ each independently represent a hydrogen, a hydrocarbyl or a functional substituent; m is an integer from 0 to 5, with the proviso that when "a" is a double bond, both (i) one of $R^1$ and $R^2$ is not present and (ii) one of $R^3$ and $R^4$ is not present.

The term "hydrocarbon groups" as used herein and in the appended claims encompasses hydrogen, hydrocarbon groups, halohydrocarbon groups, perhalohydrocarbon groups and perhalocarbyl groups. In one embodiment, $R^1$, $R^2$, $R^3$ and/or $R^4$, may independently represent hydrogen, linear or branched C1–C10 alkyl, linear or branched C2–C10 alkenyl, linear or branched C2–C10 alkynyl, C4–C12 cycloalkyl, C4–C12 cycloalkenyl, C6–C12 aryl, and C7–C24 aralkyl. In one embodiment, $R^1$ and $R^2$ or $R^3$ and $R^4$ may collectively represent a C1–C10 alkylidenyl group. Representative alkyl groups include, but are by no means limited to, methyl, ethyl, propyl, isopropyl, butyl, isobutyl, sec-butyl, tert-butyl, pentyl, neopentyl, hexyl, heptyl, octyl, nonyl and decyl. Representative alkenyl groups include, but are by no means limited to, vinyl, allyl, butenyl and cyclohexenyl. Representative alkynyl groups, include but are by no means limited to, ethynyl, 1-propynyl, 2-propynyl, 1-butynyl and 2-butynyl. Representative cycloalkyl groups include, but are by no means limited to, cyclopentyl, cyclohexyl and cyclooctyl substituents. Representative aryl groups include, but are by no means limited to, phenyl, naphthyl and anthracenyl. Representative aralkyl groups include, but are by no means limited to, benzyl and phenethyl. Representative alkylidenyl groups include, but are by no means limited to, methylidenyl and ethylidenyl groups.

In one embodiment, the perhalohydrocarbon groups may include perhalogenated phenyl and alkyl groups. The halogenated alkyl groups useful in the invention are partially or fully halogenated and are linear or branched, and have the formula $CzW"2z+1$ wherein $W"$ is independently selected from halogen and hydrogen and z is an integer of 1 to 20. In another embodiment, each $W"$ is independently selected from hydrogen, chlorine, fluorine and bromine. In another embodiment, each $W"$ is independently selected from hydrogen and fluorine.

In one embodiment, the perfluorinated substituents include perfluorophenyl, perfluoromethyl, perfluoroethyl, perfluoropropyl, perfluorobutyl and perfluorohexyl. In addition to the halogen substituents, the cycloalkyl, aryl, and aralkyl groups of the present invention may be further substituted with linear or branched C1–C5 alkyl and haloalkyl groups, aryl groups and cycloalkyl groups.

When the pendant group(s) is(are) a functional substituent, $R^1$, $R^2$, $R^3$ may $R^4$ independently represent a radical selected from (CH2)n-CH(CF3)2-O—Si(Me)3, —(CH2)n-CH(CF3)2-O—CH2-O—CH3, —(CH2)n-CH(CF3)2-O—C(O)—O—C(CH3)3, —(CH2)n-C(CF3)2-OH, —(CH2)nC(O)NH2, —(CH2)nC(O)Cl, —(CH2)nC(O)OR5, —(CH2)n-OR5, —(CH2)n-OC(O)R5, —(CH2)n-C(O)R5, —(CH2)n-OC(O)OR5, —(CH2)nSi(R5)3, —(CH2)nSi(OR5)3, —(CH2)n-O—Si(R5)3 and —(CH2)nC(O)OR6 wherein n independently represents an integer from 0 to 10 and R5 independently represents hydrogen, linear or branched C1–C20 alkyl, linear or branched C1–C20 halogenated or perhalogenated alkyl, linear or branched C2–C10 alkenyl, linear or branched C2–C10 alkynyl, C5–C12 cycloalkyl, C6–C14 aryl, C6–C14 halogenated or perhalogenated aryl, and C7–C24 aralkyl. Representative hydrocarbon groups set forth under the definition of $R^5$ are the same as those identified above under the definition of $R^1$ to $R^4$. As set forth above under $R^1$ to $R^4$ the hydrocarbon groups defined under $R^5$ may be halogenated and perhalogenated. For example, when $R^5$ is C1–C20 halogenated or perhalogenated alkyl, $R^5$ may be represented by the formula $CzW"2z+1$, wherein z and $W"$ are defined as above and at least one $W"$ on the alkyl group is a halogen. It is to be recognized that when the alkyl group is perhalogenated, all $W"$ substituents are halogenated. Examples of perhalogenated alkyl groups include, but are by no means limited to, trifluoromethyl, trichloromethyl, —C7F15, and —C11F23. Examples of perhalogenated aryl groups include, but are by no means limited to, pentachlorophenyl and pentafluorophenyl. The $R^6$ radical represents an acid labile moiety selected from —C(CH3)3, —Si(CH3)3, —CH(R7)OCH2CH3, —CH(R7)OC(CH3)3 or the following cyclic groups:

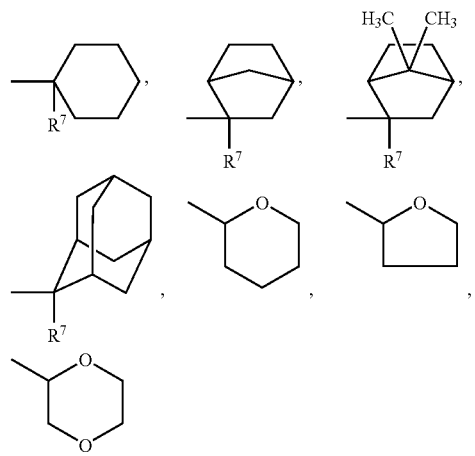

wherein $R^7$ represents hydrogen or a linear or branched ($C_6$–$C_5$) alkyl group. The alkyl groups may include methyl, ethyl, propyl, i-propyl, butyl, i-butyl, t-butyl, pentyl, t-pentyl and neopentyl. In the above structures, the single bond line projecting from the cyclic groups indicates the position where the cyclic protecting group is bonded to the acid substituent. Examples of $R^6$ radicals include 1-methyl-1-cyclohexyl, isobornyl, 2-methyl-2-isobornyl, 2-methyl-2-adamantyl, tetrahydrofuranyl, tetrahydropyranoyl, 3-oxocyclohexanonyl, mevalonic lactonyl, 1-ethoxyethyl and 1-t-butoxy ethyl.

The $R^6$ radical can also represent dicyclopropylmethyl (Dcpm), and dimethylcyclopropylmethyl (Dmcp) groups which are represented by the following structures:

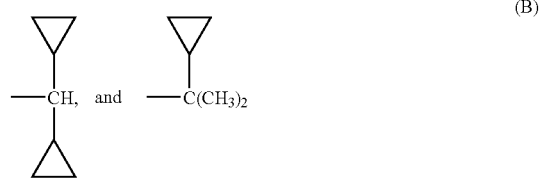

(B)

In the structure (B) above, $R^1$ and $R^4$ together with the two ring carbon atoms to which they are attached may represent a substituted or unsubstituted cycloaliphatic group containing 4 to 30 ring carbon atoms, a substituted or unsubstituted aryl group containing 6 to 18 ring carbon atoms, or a combination thereof. The cycloaliphatic group can be monocyclic or polycyclic. When unsaturated, the cyclic group may contain monounsaturation or multiunsaturation. In one embodiment, the unsaturated cyclic group may be a monounsaturated cyclic group. When substituted, the rings may contain monosubstitution or multisubstitution, wherein the substituents may independently be selected from hydrogen, linear or branched C1–C5 alkyl, linear or branched C1–C5 haloalkyl, linear or branched C1–C5 alkoxy, halogen and combinations thereof: R1 and R4 may be taken together to form the divalent bridging group, —C(O)-Q-(O)C—, which when taken together with the two ring carbon atoms to which they are attached form a pentacyclic ring, wherein Q represents an oxygen atom or the group N(R8), and R8 may be selected from hydrogen, halogen, linear or branched C1–C10 alkyl, and C6–C18 aryl. A representative structure is shown in below as Structure (C):

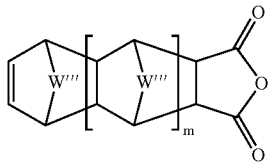

(C)

wherein each W''' is independently defined as above and m is an integer from 0 to 5.

Deuterium enriched norbornene-type monomers wherein at least one of the hydrogen atoms on the norbornene-type moiety and/or one at least one of the hydrogen atoms on a pendant hydrocarbon group described under $R^1$ to $R^4$ have been replaced by a deuterium atom are contemplated within the scope of the present invention. In one embodiment, at least 40 percent of the hydrogen atoms on the norbornene-type moiety and/or the hydrocarbon group are replaced by deuterium. In another embodiment, at least about 50 percent of the hydrogen atoms on the norbornene-type moiety and/or the hydrocarbon group are replaced by deuterium. In yet another embodiment, at least about 60 percent of the hydrogen atoms on the norbornene-type moiety and/or the hydrocarbon group are replaced by deuterium. In one embodiment, the deuterated monomers are represented by Structure (D) below:

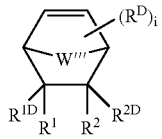

(D)

wherein W''' is defined as above, $R^D$ is deuterium, "i" is an integer from 0 to 6, $R^1$ and $R^2$ independently represent a hydrocarbyl or functional substituent as defined above and R1D and $R^{2D}$ may or may not be present and independently represent a deuterium atom or a deuterium enriched hydrocarbon group containing at least one deuterium atom; with the proviso that when "i" is 0, at least one of $R^{1D}$ and $R^{2D}$ must be present. In one embodiment, the deuterated hydrocarbon group is selected from linear or branched C1–C10 alkyl wherein at least 40 percent of the hydrogen atoms on the carbon backbone are replaced by deuterium. In another embodiment, the deuterated hydrocarbon group is selected from linear or branched C1–C10 alkyl wherein at least 50 percent of the hydrogen atoms on the carbon backbone are replaced by deuterium. In yet another embodiment, the deuterated hydrocarbon group is selected from linear or branched C1–C10 alkyl wherein at least 60 percent of the hydrogen atoms on the carbon backbone are replaced by deuterium.

A further illustrative list of norbornene-type monomers is shown below:

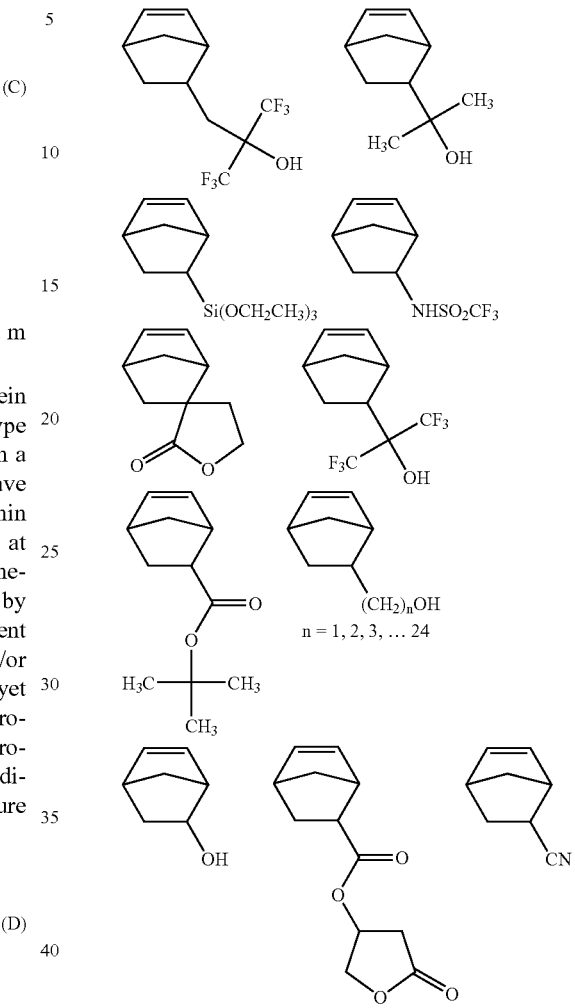

A still further illustrative list of norbornene-type monomers of the present invention includes: bicyclo[2.2.1]hept-5-ene-2-carboxylic acid 5-oxo-4-oxa-tricyclo[4.2.1.03,7]non-2-yl ester, bicyclo[2.2.1]hept-5-ene-2-carboxylic acid 2-methoxy-ethyl ester, bicyclo[2.2.1]hept-5-ene-2-carboxylic acid, bicyclo[2.2.1]hept-5-ene-2-carboxylic acid 2-oxo-tetrahydro-furan-3-yl ester, 4-Oxa-tricyclo[5.2.1.02,6]dec-8-ene-3,5-dione, 4-Oxa-tricyclo[5.2.1.02,6]dec-8-ene-3-one, 1,4,4a,5,6,7,8,8a-Octahydro-1,4-methano-naphthalen-5-ol, 2-bicyclo[2.2.1]hept-5-en-2-yl-propan-2-ol, 2-bicyclo[2.2.1]hept-5-en-2-ylmethyl-1,1,1,3,3,3-hexafluoro-propan-2-ol, 2-bicyclo[2.2.1]hept-5-ene-2-carboxylic acid 1,1,2-trimethyl-propyl ester, 2-bicyclo[2.2.1]hept-5-ene-2-carboxylic acid tert-butyl ester, 2-bicyclo[2.2.1]hept-5-ene-2-carboxylic acid 2-ethyl-adamantan-2-yl ester, 2-bicyclo[2.2.1]hept-5-ene-2-carboxylic acid 2-methyl-adamantan-2-yl ester, 2-bicyclo[2.2.1]hept-5-ene-2-carboxylic acid 1,2,3,3-tetramethyl-bicyclo[2.2.1]hept-2-yl ester, and 2-bicyclo[2.2.1]hept-5-ene-2-carboxylic acid 2-hydroxy-ethyl ester.

Multi-ethylenically unsaturated monomers of the present invention may be incorporated into the addition polymer of the present invention to provide crosslinking either during polymerization, or subsequent to polymerization, or both.

Multi-ethylenically unsaturated monomers may be polar olefinic or non-polar olefinic monomers, and the ethylenically unsaturated groups may be identical or different. Useful (meth)acrylic multi-ethylenically unsaturated monomers include, but are riot limited to, allyl (meth)acrylate, diallyl phthalate, 1,4-butylene glycol di(meth)acrylate, 1,6-hexanediol di(meth)acrylate, and 1,1,1-trimethylolpropane tri(methyl)acrylate. Useful non-polar olefins suitable as crosslinkers may be any multi-ethylenically unsaturated non-polar olefin capable of incorporation into more than one polymer chain of the addition polymer of the present invention, including, for example: (α,ω-alkadienes, such as 1,5-hexadiene; other non-conjugated alkadienes such as 1,4-hexadiene; and non-polar olefinic monomers containing three or more carbon-carbon double bonds.

Crosslinked polymers can be prepared by copolymerizing the norbornene-type monomer(s) set forth under Structure (B) above with a multifunctional norbornene-type crosslinking monomer(s). By multifunctional norbornene-type crosslinking monomer is meant that the crosslinking monomer contains at least two norbornene-type moieties (norbornene-type double bonds), each functionality being polymerizable in the presence of the catalyst system of the present invention. The crosslinkable monomers include fused multicyclic ring systems and linked multicyclic ring systems. Examples of fused crosslinking agents are illustrated in structures below. For brevity, norbornadiene is included as a fused multicyclic crosslinking agent and is considered to contain two polymerizable norbornene-type double bonds.

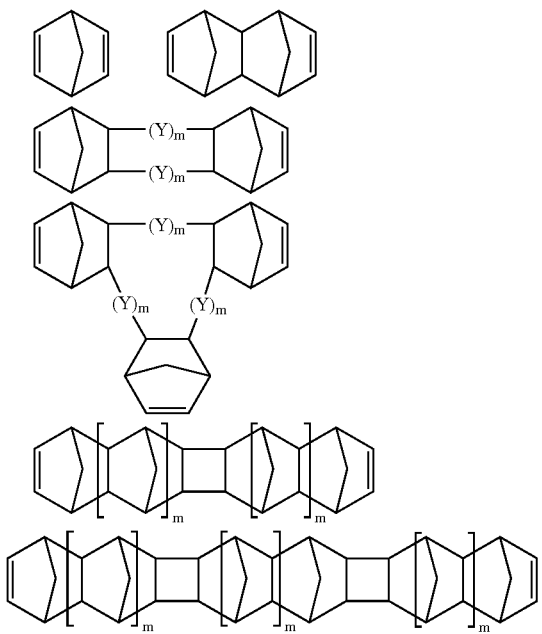

wherein Y represents a methylene (—CH$_2$—) group and m independently represents an integer from 0 to 5, and when m is 0, Y represents a single bond. Representative monomers under the forgoing formulae are disclosed by, for example, Bell et al. in U.S. Pat. No. 6,350,832.

Hydrocarbon groups, R, include, for example, hydrogen, linear and branched C1–C20 alkyl, C5–C10 cycloalkyl, linear and branched C2–C20 alkenyl, C6–C15 cycloalkenyl, allylic ligands or canonical forms thereof, C6–C30 aryl, C6–C30 heteroatom containing aryl and C7–C30 aralkyl; each of the foregoing groups can optionally be substituted with hydrocarbyl and/or heteroatom substituents selected from linear or branched C1–C5 alkyl, linear or branched C1–C5 haloalkyl, linear or branched C2–C5 alkenyl and haloalkenyl, halogen, sulfur, oxygen, nitrogen, phosphorus, and phenyl optionally substituted with linear or branched C1–C5 alkyl, linear or branched C1–C5 haloalkyl, and halogen; wherein the cycloalkyl and cycloalkenyl groups may be monocyclic or multicyclic; wherein the aryl groups can be a single ring (e.g., phenyl) or a fused ring system (e.g., naphthyl); wherein the cycloalkyl, cycloalkenyl and aryl groups can be taken together to form a fused ring system; and wherein each of the monocyclic, multicyclic and aryl ring systems may optionally be monosubstituted or multisubstituted with a substituent independently selected from hydrogen, linear and branched C1–C5 alkyl, linear and branched C1–C5 haloalkyl, and linear and branched C1–C5 alkoxy, chlorine, fluorine, iodine, bromine, C5–C10 cycloalkyl, C6–C15 cycloalkenyl and C6–C30 aryl.

In the method of polymerizing of the present invention, the cationic metal-pair complex can be used to polymerize: one or more "non-polar olefinic monomers"; one or more "polar olefinic monomers"; or combinations of one or more non-polar olefinic monomers and one or more polar olefinic monomers to form the addition polymer of the present invention. The number average molecular weight, Mn, of the addition polymer of the present invention is: at least 500, at least 1,000, at least 10,000, or at least 20,000; and no more than 5,000,000, no more than 1,000,000, no more than 500,000, or no more than 200,000. The polydispersity of the MWD of the addition polymer of the present invention is: at least 1.000, at least 1.001, at least 1.01, or at least 1.05; and no more than 10, no more than 2.5, no more than 1.5, or no more than 1.1. The MWD of the addition polymer of the present invention may be unimodal or multi-modal, wherein multi-modal includes bimodal and trimodal, as well as higher degrees of modality, and wherein the polydispersity of the MWD for each mode may have the upper and lower limits defined supra.

The "poly(non-polar olefin)" of the present invention is any polymer that can be made from any of the non-polar olefinic monomers of the present invention. The following is a short, non-exhaustive, list of illustrative examples poly (non-polar olefin)s, which may be homopolymers or copolymers: polyethylene, polypropylene, ethylene-propylene copolymers, ethylene-propylene-(non-conjugated diene monomer) ("EPDM") copolymers, LLDPE, polystyrene homo- and copolymers, polybutadiene homo- and copolymers, and polynorbornene. In fact, the poly(non-polar olefin) may include, as polymerized units, any non-polar olefin capable of insertion addition polymerization in the presence of the cationic metal-pair complex of the present invention.

The "poly(polar olefin)" of the present invention is any polymer that can be made from the polar olefinic monomers of the present invention. The following is short, non-exhaustive, list of illustrative examples poly(polar olefin)s, which may be homopolymers or copolymers: poly[(meth) acrylates] such as poly(methyl methacrylate), poly(butyl acrylate-co-methyl methacrylate), poly[vinylidene halide(s)], poly(vinyl acetate), and poly(vinyl ether). In fact, the poly(polar olefin) may include, as polymerized units, any polar olefin capable of insertion addition polymerization in the presence of the cationic metal-pair complex of the present invention.

A "poly[(polar olefin)-(non-polar olefin)]" of the present invention is any polymer that can be made from at least one of the non-polar olefinic monomers and at least one of the polar olefinic monomers of the present invention. The following is short, non-exhaustive, list of illustrative examples of poly[(polar olefin)-(non-polar olefin) which copolymers: poly[ethylene-co-methyl(meth)acrylate], poly[octene-co-methyl(meth)acrylate], poly[propylene-co-(meth)acrylate], poly[norbornene-co-(meth)acrylate]. In fact, the poly[(polar olefin)-(non-polar olefin)] may include, as polymerized units, any polar olefin and any non-polar olefin capable of insertion addition polymerization in the presence of the cationic metal-pair complex of the present invention. The molar ratio of polar olefinic monomers to non-polar olefinic monomers, present as polymerized units in the poly[(polar olefin)-(non-polar olefin)] of the present invention is: at least 0.05:99.95, at least 0.5:99.5, at least 10:90, at least 20:80, or at least 40:60; or no more than 99.95:0.05, no more than 99.5:0.5, no more than 90:10, no more than 80:20, or no more than 60:40.

When the addition polymer of the present invention is a copolymer, that copolymer may include, as polymerized units, two, three, four, or more than four different monomers, with no particular limit to the number of different monomers. For example, in one embodiment of the present invention, the poly[(polar olefin)-(non-polar olefin)] is a terpolymer including, as polymerized units, norbornene, 1-octene, and methyl acrylate.

When at least one polar monomer polymerized by the method of the present invention to form a "poly[(polar olefin)-(non-polar olefin)]" is a (meth)acrylate monomer, the molar ratio of (meth)acrylate monomers to non-polar olefinic monomers, present as polymerized units in the poly[(polar olefin)-(non-polar olefin)] of the present invention is: at least 0.05:99.95, at least 0.5:99.5, at least 10:90, at least 20:80, or at least 40:60; or no more than 99.95:0.05, no more than 99.5:0.5, no more than 90:10, no more than 80:20, or no more than 60:40.

Further, when both polar olefinic monomers and non-polar olefinic monomers are polymerized together in the polymerization method of the present invention, the molar percentage of monomer incorporated into poly[(polar olefin)-(non-polar olefin)], based on total moles of monomer incorporated into all polymer produced in the polymerization, is: at least 70, at least 80, at least 90 or at least 95; no more than 100, no more than 99, no more than 97.

In particular, when both polar olefinic monomers and non-polar olefinic monomers are polymerized together in the polymerization method of the present invention, and at least one of the polar olefinic monomers is a (meth)acrylate monomer, the molar percentage of monomer incorporated into poly[(polar olefin)-(non-polar olefin)], based on total moles of monomer incorporated into all polymer produced in the polymerization, is: at least 70, at least 80, at least 90 or at least 95; no more than 100, no more than 99, no more than 97.

Still further, when the addition polymer of the present invention is a poly(polar olefin) and at least one of the polar olefinic monomers, incorporated as polymerized units, is a (meth)acrylate monomer, the molar ratio of all (meth)acrylate monomers, present as polymerized units, to all non-(meth)acrylate monomers, present as polymerized units, is: at least 0.05:99.95, at least 0.5:99.5, at least 10:90, at least 20:80, or at least 40:60; or no more than 100:0, no more than 99.5:0.5, no more than 90:10, no more than 80:20, or no more than 60:40.

Similarly, when the addition polymer of the present invention is a poly[(polar olefin)-non-polar olefin)] and at least one of the polar olefinic monomers, incorporated as polymerized units, is a (meth)acrylate monomer, the molar ratio of all (meth)acrylate monomers, present as polymerized units, to all non-(meth)acrylate monomers, present as polymerized units, is: at least 0.05:99.95, at least 0.5:99.5, at least 10:90, at least 20:80, or at least 40:60; or no more than 99.95:0.05, no more than 99.5:0.5, no more than 90:10, no more than 80:20, or no more than 60:40.

When the addition polymer of the present invention includes, as polymerized units, at least one cyclic olefin, incorporated as polymerized units, the molar ratio of all cyclic olefin monomers, present as polymerized units, to all non-(cyclic olefin) monomers, present as polymerized units, is: at least 0.05:99.05, at least 0.5:99.5, at least 10:90, at least 20:80, or at least 40:60; or no more than 100:0, no more than 99.5:0.5, no more than 90:10, no more than 80:20, or no more than 60:40.

Crosslinked polymers can be prepared by copolymerizing the norbornene-type monomer(s) set forth under Structure (B) above with a multifunctional norbornene-type crosslinking monomer(s). By multifunctional norbornene-type crosslinking monomer is meant that the crosslinking monomer contains at least two norbornene-type moieties (norbornene-type double bonds), each functionality being polymerizable in the presence of the catalyst system of the present invention. The crosslinkable monomers include fused multicyclic ring systems and linked multicyclic ring systems. Examples of fused crosslinking agents are illustrated in structures below. For brevity, norbornadiene is included as a fused multicyclic crosslinking agent and is considered to contain two polymerizable norbornene-type double bonds.

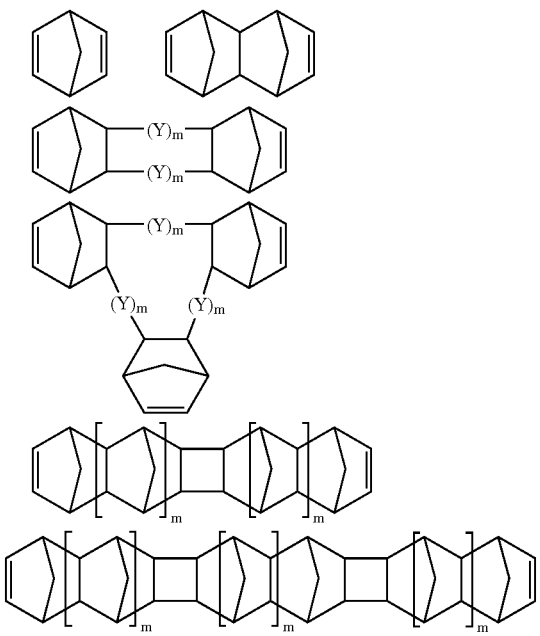

wherein Y represents a methylene (—CH$_2$—) group and m independently represents an integer from 0 to 5, and when m is 0, Y represents a single bond. Representative monomers tinder the forgoing formulae are disclosed by, for example, Bell et al. in U.S. Pat. No. 6,350,832.

Hydrocarbon groups, R, suitable for use with the present invention include, for example, hydrogen, linear and branched C1–C20 alkyl, C5–C10 cycloalkyl, linear and branched C2–C20 alkenyl, C6–C15 cycloalkenyl, allylic ligands or canonical forms thereof, C6–C30 aryl, C6–C30 heteroatom containing aryl and C7–C30 aralkyl; each of the foregoing groups can optionally be substituted with hydrocarbyl and/or heteroatom substituents selected from linear or branched C1–C5 alkyl, linear or branched C1–C5 haloalkyl, linear or branched C2–C5 alkenyl and haloalkenyl, halogen, sulfur, oxygen, nitrogen, phosphorus, and phenyl optionally substituted with linear or branched C1–C5 alkyl, linear or branched C1–C5 haloalkyl, and halogen; wherein the cycloalkyl and cycloalkenyl groups may be monocyclic or multicyclic; wherein the aryl groups can be a single ring (e.g., phenyl) or a fused ring system (e.g., naphthyl); wherein the cycloalkyl, cycloalkenyl and aryl groups can be taken together to form a fused ring system; and wherein each of the monocyclic, multicyclic and aryl ring systems may optionally be monosubstituted or multisubstituted with a substituent independently selected from hydrogen, linear and branched C1–C5 alkyl, linear and branched C1–C5 haloalkyl, linear and branched C1–C5 alkoxy, chlorine, fluorine, iodine, bromine, C5–C10 cycloalkyl, C6–C15 cycloalkenyl and C6–C30 aryl.

The method of preparing the addition polymer of the present invention can be carried out at a reaction temperature (° C.) of: at least −100° C., at least −50° C., at least 0° C., or at least 20° C.; and no more than 200° C., no more than 160° C., no more than 140° C., or no more than 120° C. This method can be carried out at a pressure (in atmospheres, i.e., the pressure inside the reactor is 1.0 atmosphere for a value of 1.0) of: at least 0.01, at least 0.1, at least 0.5, or at least 1.0, and no more than 1,000, no more than 100, no more than 10, or no more than 5. Further, the molar ratio of ethylenically unsaturated monomer to the cationic metal-pair complex of present invention is: at least 50:1, at least 200:1, at least 250:1, or at least 1,000:1, and no more than 5,000,000:1, no more than 2,000,000:1, or no more than 500,000:1, no more than 250,000:1, or no more than 100,000:1. For gaseous monomers at high pressures, in particular constant high pressures, e.g., equal to or greater than 400 psi, the molar ratio of ethylenically unsaturated monomer to the cationic metal-pair complex of present invention may be even higher than 5,000,000:1, for example, no more than 6,000,000:1, no more than 8,000,000:1, or even higher the method of polymerization of the present invention, the amount of diluent, expressed as volume (milliliters) of diluent per millimole of the cationic metal-pair complex of the present invention, is: at least 0.0, at least 10, at least 50, or at least 100; and no more than 10,000,000, no more than 1,000,000, no more than 100,000, no more than 10,000, or no more than 5,000.

When particles of the addition polymer are produced by the method of preparing the addition polymer of the present invention, depending on the particular details of that method, the polymer particles have a mean particle diameter (i.e., mean particle size), expressed in microns, of: at least 0.002, at least 0.04, at least 0.1, or at least 0.8; and no more than 500, no more than 20, no more than 10, no more than 5, or no more than 3. The PSD polydispersity of the particles is: at least 1, at least 1.001, at least 1.01, or at least 1.05; and no more than 10, no more than 5, no more than 1, no more than 1.3, or no more than 1.1. The PSD of the addition polymer of the present invention may be unimodal or multi-modal, wherein multi-modal includes bimodal and trimodal, tetramodal, as well as higher degrees of modality, and wherein the polydispersity of the PSD for each particle size mode may have the upper and lower limits defined supra. One skilled in the art of catalytic polymerization will further recognize that it is even possible to prepare particles having a mean particle diameter greater than 1000 microns (1 millimeter). This may happen, for example, as the result of evaporation during or after solution or bulk polymerization, or polymerization involving polymer precipitation. In this way, even larger monolithic polymer structures may be formed.

The method for preparing the addition polymer of the present invention may be carried out in bulk or in a diluent. If the catalytic composition is soluble in the one or more ethylenically unsaturated monomers to be polymerized, it may be convenient to carry out the polymerization in bulk. Such bulk polymerizations may be carried out, for example, in batch or continuous mode, or by reaction injection molding or other mold based techniques. In another embodiment of the present invention, the polymerization is carried out in a diluent. Any organic or aqueous diluent which does not adversely interfere with the catalytic composition and is a solvent for the monomers may be employed. Illustrative examples of organic solvents are: aliphatic (non-polar) hydrocarbons, e.g., hexane and heptane; alicyclic hydrocarbons, e.g., cyclohexane; aromatic hydrocarbons, e.g., toluene; halogenated (polar) hydrocarbons, e.g., methylene chloride and chlorobenzene. For polymerization systems in which the catalytic composition is not degraded, the diluent may be water, solvents miscible with water, and combinations thereof. The diluent may further include, for example, any of the fugitive substances disclosed in US patent application U.S. Pat. No. 6,632,531, e.g., 2,2-dimethylpropane, 1,1-difluoroethane, 1,1,1,2-tetrafluoroethylene propane (−42.1° C.), carbon dioxide, and tetrafluoromethane (−130° C.), wherein the reaction is carried out under supercritical or below supercritical conditions.

The suitability of a given atmosphere for carrying out any of the reactions of the present invention will depend upon the stability of the reactants, intermediates and by-products to that atmosphere. Typically gases, including nitrogen or argon, for example, are utilized. Choice of atmosphere gases for a given polymerization will be apparent to one of ordinary skill in the art.

The diluent of the present invention may also be an "ionic liquid". Ionic liquids are either organic salts or mixtures of salts that are fluid at room or near-room temperature (see: Dupont, *J. Chem. Rev.* 2002, 102, 3667; Kabisa, *P. Prog. Poly. Sci.* 2004, 29, 3). A property of ionic liquids is their zero vapor pressure, making them potential solvents for zero-(volatile organic) chemical processes and possible alternative for supercritical CO2. Ionic liquids are, for example, composed of bulky 1,3-dialkylimidazolium, alkylammonium, alkylphosphonium or alkylpyridinium organic cations and inorganic anions such as most frequently AlCl4-, BF4- or PF6 but also NO3, ClO4, CF3COO2, CF3SO3 or CH3COO2 and other anions. The most commonly used neutral ionic liquids include 1-butyl-3-methylimidazolium hexafluorophospate or tetrafluoroborate abbreviated as [bmim][PF6] and [bmim][BF4] correspondingly.

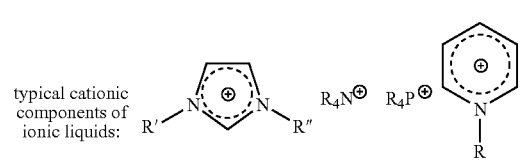

typical cationic components of ionic liquids:

-continued

| typical anionic components of ionic liquids: | $AlCl_4^\ominus$, $BF_4^\ominus$, $PF_6^\ominus$, $ClO_4^\ominus$, $NO_3^\ominus$ $CF_3COO^\ominus$, $CF_3SO_3^\ominus$, $CH_3COO^\ominus$, $(CF_3SO_2)_2N^\ominus$ |
|---|---|

When utilized in the preparation of the addition polymer of the present invention, the monomers and/or catalytic composition of the present invention may not be fully soluble, or may even be insoluble, in the diluent. This situation might, for example, occur in heterogeneous systems wherein the locus of polymerization must be accessed by both catalytic composition and ethylenically unsaturated monomer. In such cases, it may be advantageous to employ one or more transport agents to transport monomers, or the complexes of the catalytic composition, to the desired locus of polymerization. For example, transport agents such as cyclodextrins may be advantageously employed to transport ethylenically unsaturated monomers having low, or very low, water solubility, across the aqueous phase to polymer particles during aqueous emulsion polymerization.

In addition to being carried out as bulk and solution polymerizations, the polymerizations of the present reaction can be carried out in the gas phase in, for example fluidized bed or stirred tank reactors, optionally in the presence of prepolymer for control of the size and shape of polymers formed. Polyethylene, polybutene, polyhexene, and related copolymers, including copolymers containing, for example, methyl methacrylate may be prepared by gas phase polymerization.

A still further method for producing the addition polymer of the present invention may be any appropriate method known to the art, including, but not limited to aqueous solution polymerization, emulsion polymerization, suspension polymerization, microemulsion polymerization, miniemulsion, and slurry polymerization. Descriptions of emulsion polymerization methods are disclosed in Blackley, D. C. Emulsion Polymerisation; Applied Science Publishers: London, 1975; Odian, G. Principles of Polymerization; John Wiley & Sons: New York, 1991; Emulsion Polymerization of Acrylic Monomers; Rohm and Haas, 1967. The method of the present invention further includes methods disclosed in U.S. Pat. No. 6,632,531, and published U.S. patent application US2003/0007990.

The cationic metal-pair complex of the present invention is suitably employed as an unsupported material. Alternatively, any of the complexes of the present invention may be supported on an "inorganic solid carrier" ("inorganic carrier") or an "organic polymeric solid catalyst carrier" ("organic carrier") which is normally solid under reaction conditions and is heterogeneous, i.e., is substantially insoluble in the reaction medium. Used herein, the terms "carrier" and "support" are used interchangeably. Illustrative of suitable inorganic carriers are inorganic acidic oxides such as alumina and inorganic materials known as refractory oxides. Suitable refractory oxides include synthetic components as well as acid treated clays and similar materials such as kieselguhr or crystalline macroreticular aluminosilicates known in the art as molecular sieves. In general, synthetic catalyst carriers are preferred over natural occurring materials or molecular sieves. Exemplary synthetic catalyst carriers include alumina, silica-alumina, silica-magnesia, silica-alumina-titania, silica-alumina-zirconia, silica-titania-zirconia, silica-magnesia-alumina, magnesium chloride, and the like. Organic carriers include, for example, macroreticular resins which may, or may not, bear polar functional groups or carbon-carbon double bonds.

When the cationic metal-pair complex of the present invention is supported, its proportion to carrier is not critical. In general, proportions of cationic metal-pair complex, or precursor complex of the present invention, in percent by weight, based on the catalyst carrier, are: at least 0.001%, at least 0.01%, at least 0.1%, or at least 1.0%; and no more than 5%, no more than 10%, no more than 20%, or no more than 70%. The cationic metal-pair complex is introduced onto the carrier in any suitable manner. In one modification, the supported cationic metal-pair complex is prepared by intimately contacting the preformed cationic metal-pair complex and the carrier in an inert diluent, which may or may not be the same inert diluent employed for preparing the cationic metal-pair complex. In another modification, the cationic metal-pair complex can be prepared directly on the catalyst carrier support surface by contacting the cationic metal-pair complex precursors in the presence of the catalyst carrier in a suitable inert diluent. In addition to the supports enumerated supra, the cationic metal-pair complex of the present invention can be supported on any of the supports or matrices disclosed in published U.S. patent applications US2002/60226997, US2002/0052536, in U.S. patent applications U.S. Ser. No. 60/383,650 and U.S. Ser. No. 60/440, 142, and in Chen and Marks, Chem. Rev., 2000 100, 1391–1434.

One skilled in the art will recognize that, when aqueous emulsion polymerization and microemulsion polymerization are used to prepare the addition polymer of the present invention, surfactants will, optionally, be present in the reaction medium. Conventional surfactants may be used to stabilize the emulsion polymerization systems before, during, and after polymerization of monomers. For emulsion polymers, these conventional surfactants will usually be present at levels of 0.1 percent to 6 percent by weight based on the weight of total monomer, whereas microemulsion polymerizations may require level as high as 30 weight %. Useful surfactants include: anionic surfactants, for example, sodium lauryl sulfate and sodium dodecyl benzene sulfonate; nonionic surfactants, for example, glycerol aliphatic esters and polyoxyethylene aliphatic esters; and amphoteric surfactants, for example, aminocarboxylic acids, imidazoline derivatives, and betaines.

Methods for generating cationic mono-metallic complexes by treating their neutral precursors with stoichiometric (i.e., one equivalent per metal atom) or excess amounts of activator component are disclosed in Chen, E. Y. -X.; Marks, T. J. Chem. Rev. 2000, 100, 1391 and Mecking, S. Coord. Chem. Rev. 2000, 203, 325.

In the method of preparing the catalytic composition of the present invention, a cationic metal-pair complex is generated by treating a precursor complex using amounts of activator component suitable to remove leaving group Y. The leaving group Y is replaced with at least one replacement moiety in an amount sufficient to at least fill any coordination sites, of metal atoms $M^1$ and $M^2$, vacated by the removal of said leaving group Y, to form said cationic metal-pair complex.

The precursor complex from which the leaving group Y is removed may be a full-(metal pair) complex or a first semi-(metal pair) complex. When the precursor is a first semi-(metal pair) complex, the leaving group Y is replaced by a second semi-(metal pair) complex. The temperature (° C.) for the reaction generating the cationic metal-pair complex is: at least −100° C., at least −50° C., at least 0° C., or at least 20° C.; and no more than 200° C., no more than 160°

C., no more than 140° C., or no more than 120° C. In the method of preparation of the cationic metal-pair complex of the present invention, the amount of diluent, expressed as volume (milliliters) pre millimole of cationic metal-pair complex, is: at least 0.0, at least 2, at least 5, or at least 10; and no more than 1,000, no more than 500, no more than 200, or no more than 100. Useful diluents include any of the non-aqueous diluents (vide supra) useful in carrying out the polymerization of the ethylenically unsaturated monomers of the present invention. In cases in which neither the precursor complex nor the cationic metal-pair complex is adversely affected, water or water miscible diluents may be utilized as well.

In one embodiment of the method of the present invention for preparing, from a full-(metal-pair) precursor complex, a cationic metal-pair complex, the removal of leaving group Y is represented by the following reaction scheme:

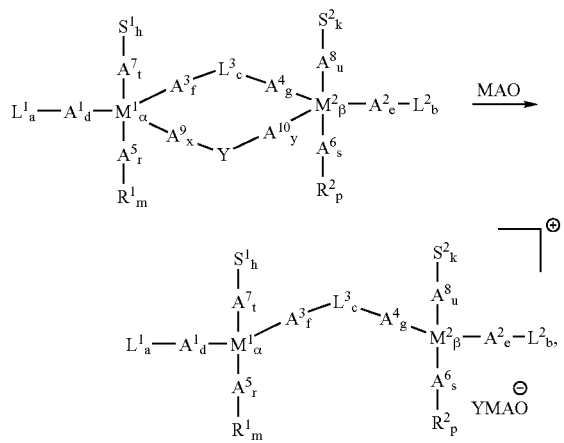

wherein the activator component is MAO or modified MAO.

In another embodiment of the method of the present invention, the cationic metal-pair complex is formed by: oxidative cleavage of the bond between first metal atom, $M^1$, and a leaving group Y and of the bond between second metal atom, $M^2$, and that leaving group Y of a full-(metal-pair) precursor complex. This embodiment is represented by the following reaction scheme:

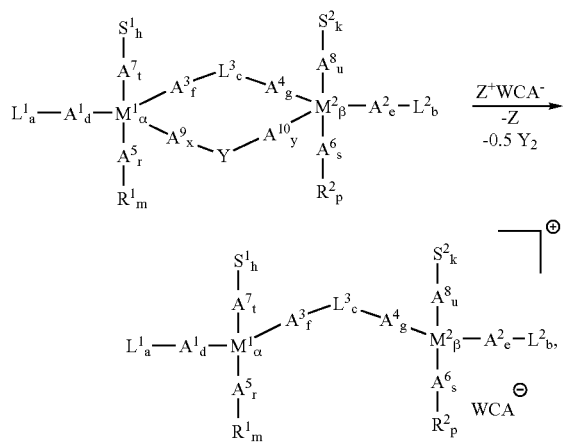

wherein the activator component is Z+WCA− and Z+ may be, for example, Ag+ or Cp2Fe+. Used herein, "Cp" denotes "cyclopentadienyl", and Cp2Fe+ denotes the "ferricenium ion".

In a further embodiment of the method of the present invention, the cationic metal-pair complex is formed by: abstractive cleavage of the bond between first metal atom, $M_1$, and the leaving group Y, and of the bond between second metal atom, $M^2$, and the leaving group Y of a full-(metal-pair) precursor complex. This embodiment is represented by the following reaction scheme:

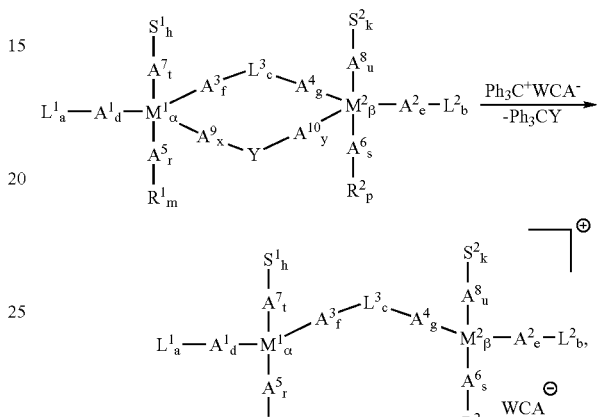

wherein the activator component is, for example, Ph3C+ WCA−. Used herein Ph3C+ is the "trityl cation", also denoted "triphenyl carbocation".

In a still further embodiment of the method of the present invention, the cationic metal-pair complex is formed by protonolysis of the bond between first metal atom, $M_1$, and the leaving group Y, and of the bond between second metal atom, $M^2$, and the leaving group Y of a full-(metal-pair) precursor complex. This embodiment is represented by the following reaction scheme:

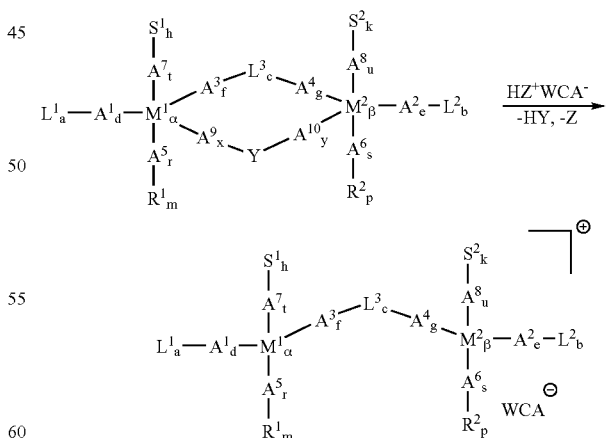

wherein, for example, Z is: $NR_jAr_k$ (wherein R is a methyl or other alkyl group; Ar is a phenyl or other aryl group); $(OEt_2)_2$; first or second labile ligand; some other labile neutral electron donor ligand that is present, but does not become part of the cationic metal-pair complex.

In yet another embodiment of the method of the present invention, the cationic metal-pair complex is formed by abstraction by a neutral Lewis acid of leaving group Y of a full-(metal-pair) precursor complex. This embodiment is represented by the following reaction scheme:

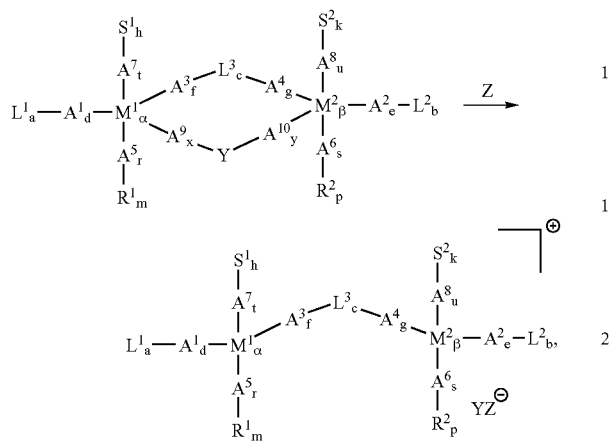

wherein Z is the Lewis acid and, for example, $Z=B(C_6F_5)_3$ or other $B(Ar^F)_3$ compounds. "$Ar^F$" denotes "fluoroaryl", and "YZ" serves as weakly coordinating anion, $WCA^-$.

In another embodiment of the method of the present invention, the cationic metal-pair complex is formed by abstraction by silver, thallium or alkali metal salts of leaving group Y of a full-(metal-pair) precursor complex. This embodiment is represented by the following reaction scheme:

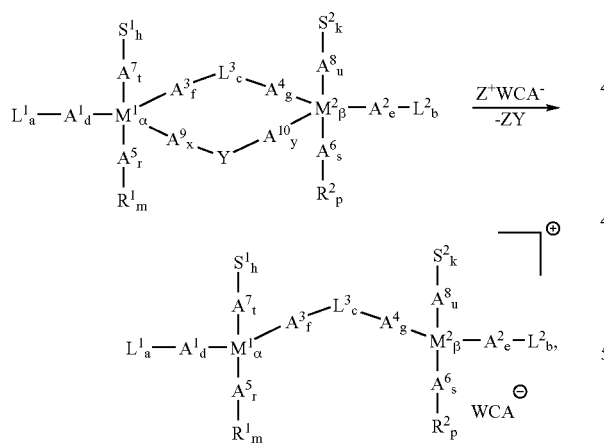

wherein, for example, Z=Ag, Tl, Li, Na, K, or Cs.

In another embodiment of the method of the present invention, a first semi-(metal pair) precursor complex is combined with any of the above activator components, (e.g., silver salt) to remove leaving group Y, and leaving group Y is replaced by a second semi-(metal pair) precursor complex during or after the removal of leaving group Y from the first semi-(metal pair) complex. It is understood for the equations of this paragraph, and the paragraph immediately fallowing, that bridging moiety $L^3$ is derived from a first ligand or first anionic hydrocarbyl radical of a precursor complex, or a second ligand or a second anoinic hydrocarbyl radical of a precursor complex. For example, a second ligand (i.e., a ligand of the set $L^2$), already bonded to $M^2$ and capable of forming a coordination bond with $M^1$, becomes a third ligand (i.e., a ligand of the set $L^3$) upon formation of that coordination bond with $M^1$. The weakly coordinating anion, $WCA^-$, may be formed, for example, by the combining of the activator with Y, or by the disniacement of $Y^-$ with a cationic moiety of an ionic activator, with the anionic moiety of that activator remaining as $WCA^-$.

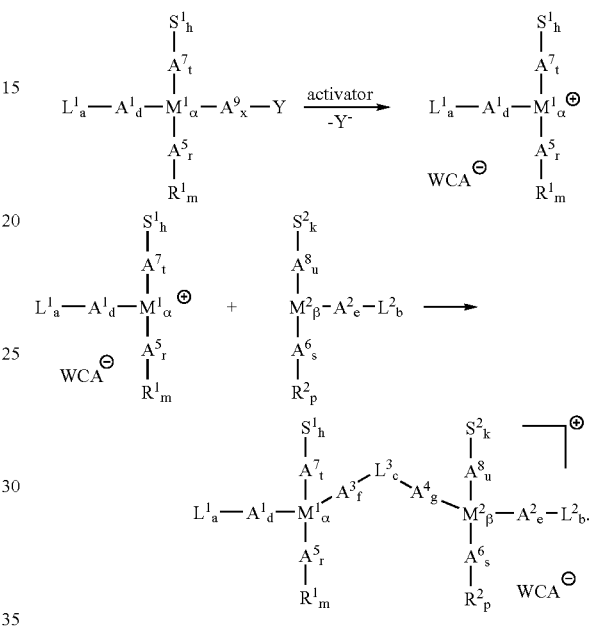

A non-exhaustive list of additional schemes of generation of the cationic metal-pair complex of the present invention includes:

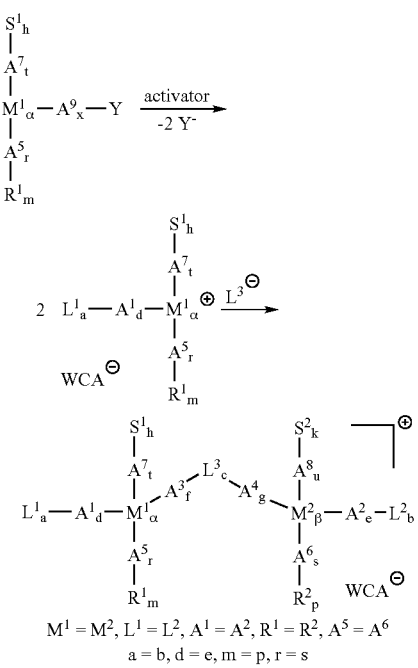

$M^1 = M^2, L^1 = L^2, A^1 = A^2, R^1 = R^2, A^5 = A^6$
$a = b, d = e, m = p, r = s$

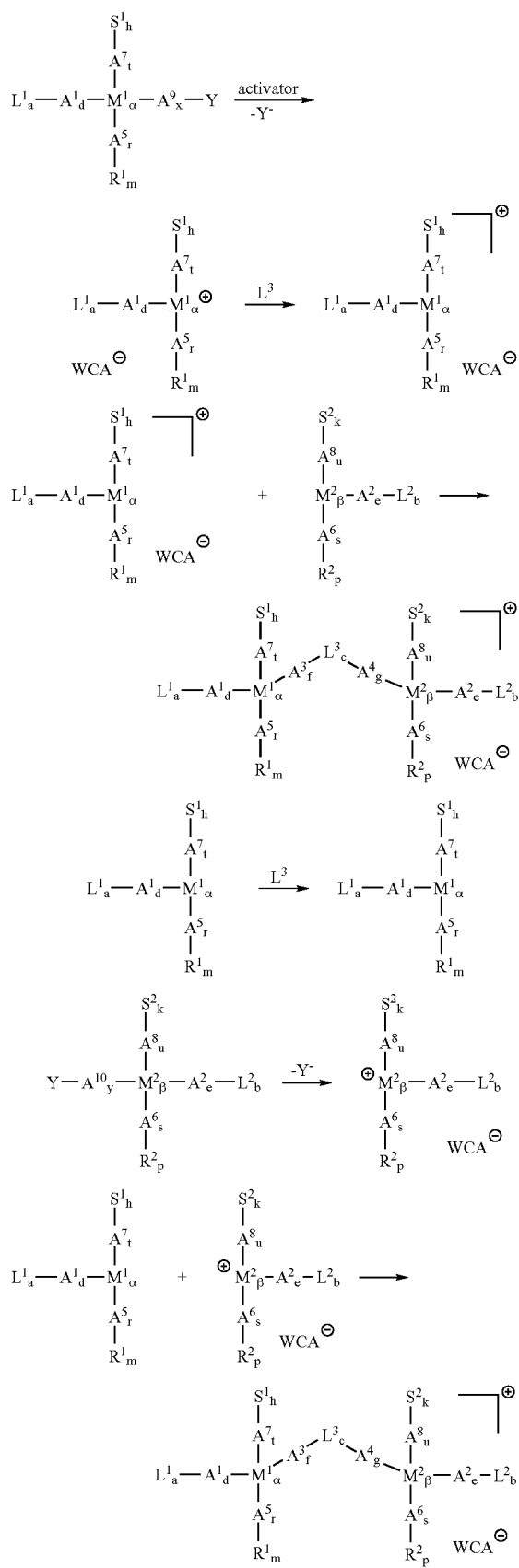

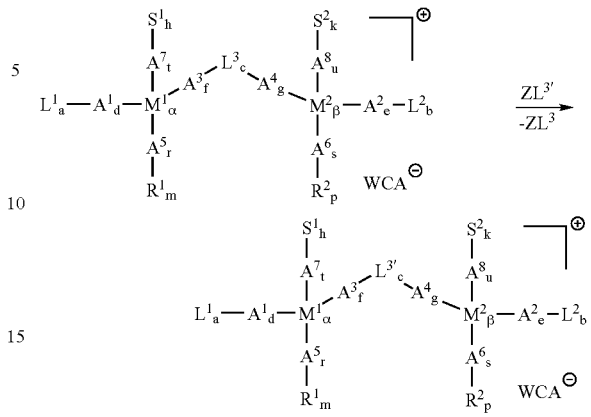

When $L^3$ or $L^{3-}$ appears over an arrow in an above equations, it will be understood that $L^3$ or $L^{\mu-}$ represents a ligand capable of forming at least one coordination bond with each of $M^1$ and $M^{2,}$ and which, upon formation of at least one coordination bond to each of $M^1$ and $M^{2,}$ will become a third ligand (bridging moiety) of the set $L^3$.

The following is an example of the reaction using $ZL^{3'}$ (immediately above):

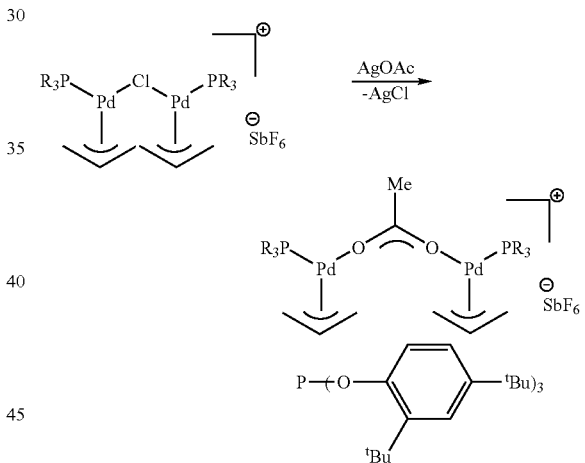

In another embodiment of the method of preparing the cationic metal-pair complex of the present invention, any of the preceding reaction schemes may be carried out in the presence of an inorganic support, an organic polymeric support, a pair-coupling moiety, or a combination thereof. Within this embodiment, a non-exhaustive list of ways in which a support or pair-coupling moiety may be utilized includes: combination with a precursor complex, followed by addition of an activator component; combination with of an activator component, followed by addition of a precursor component; when a first semi-(metal pair) precursor complex is involved and the first semi-(metal pair) precursor complex is not already associated with a support, combining the first semi-(metal pair) precursor complex with a support and then reacting it with the second semi-(metal pair) precursor complex, or combining the first semi-(metal pair) precursor complex with a supported second semi-(metal pair) precursor complex; or combining the cationic metal-pair complex and a support.

The addition polymers prepared using the catalytic composition of the present invention afford many new products and market opportunities currently unachievable. Applications for the polymers include polymers useful in preparation of photoresists, polymers useful in electronics, polymers useful in computer components and microcomponents, polymers useful as plastics additives (e.g., heat distortion temperature improvers, impact modifiers, and processing aids), UV stable thermoplastic elastomers, colorable (including dyeable) polyolefin plastics and other polymers, and new low-cost, high melting point, optical polymers. The polymers of the present invention include polymers that, while having polyolefin type attributes, are also paintable, or otherwise coatable without recourse to pretreatment which adds expense and often creates environmental hazard. Applications further include paint binders that can undergo film formation in the absence of coalescents while still providing paints that are both durable and dirt-resistant, enabling productions of, for example, aqueous and powder formulations having reduced or zero concentrations of volatile organic compounds (VOCs) without sacrificing paint properties. Polymers selected from those of the present invention may be the principal, sole, or minor components of coatings (paints, stains, varnishes, adhesives and mastics) for essentially any substrate, including non-polar and polar thermoplastics, thermoset plastics, other organic and inorganic polymers, glass, stone, ceramic, wood, particle board, paper, leather, concrete, asphalt, cement, and metal. Whether the polymers of the present invention are included in the coating, the substrate, or both, the resulting coated substrates can, for example, be decorative and/or of enhanced durability, attributes that are highly desirable in, for example, vehicular, appliance, architectural, household, device housing (including electronic), decorative design, and ornamental applications.

Polymers of the present invention are further useful as ionomers for applications requiring extreme toughness (e.g., golf ball covers) or superior sealing properties (e.g., bacon packaging). They find further utility as thermoplastics, as thermosets, and as compatibilizers, affording compatible blends of non-polar and polar polymers with enhanced properties compared with the component polymers. They find still further utility as impact and processing enhancing additives for thermoplastic and thermoset resins. When functionalized appropriately, these polymers behave as colorants, UV and other radiation absorbers, and photosensitizers. When combined with active ingredients of various types, they can enable delivery of those ingredients to targeted loci. Such active ingredients include, pharmaceutical, pesticides, other biologically active substances, colorants and other optically active substances, and analytical tags.

The polymers of the present invention are useful inter alia in electronic and optical applications. They are useful as components in resist materials utilized in the manufacture of integrated circuits (ICs). The patterning of IC's is carried out according to various lithography techniques known in the art. Polymers of the present invention that contain acid labile groups pendant from the backbone can be used in radiation sensitive photoresist compositions. (J. V. Crivello et al., Chemically Amplified Electron-Beam. Photoresists, *Chem. Mater.* 1996 8, 376–381). Electronic applications further include, but are not limited to, dielectric films (i.e., multichip modules and flexible circuits), chip attach adhesives, underfill adhesives, chip encapsulants, glob tops, near hermetic board and chip protective coatings, embedded passives, laminating adhesives, capacitor dielectrics, high frequency insulator/connectors, high voltage insulators, high temperature wire coatings, conductive adhesives, reworkable adhesives, photosensitive adhesives and dielectric film, resistors, inductors, capacitors, antennas and printed circuit board substrates. In optical applications uses include but are not limited to optical films, ophthalmic lenses, wave guides, optical fiber, photosensitive optical film, specialty lenses, windows, high refractive index film, laser optics, color filters, optical adhesives, and optical connectors.

Some embodiments of the invention will now be described in detail in the following Examples. Some of the chemicals used in the Examples are listed in Table II.

TABLE II

Chemicals used in the examples.

| Chemical (purity) | Source | CAS # |
|---|---|---|
| (Allyl)palladium(tricyclohexylphosphine)chloride: | (a) | |
| Allylpalladium chloride dimer (99%) | Strem, Newburyport, MA 01950-4098 | 12012-95-2 |
| Chlorobenzene | Aldrich | 108-90-7 |
| Methylene Chloride (99+%) | Aldrich | 75-09-2 |
| Hexanes (98+) | Aldrich | 73513-42-5 |
| Hexafluoroisopropanol norbornene, 5-R—NB (R = $CH_2C(CF_3)_2OH$) | | 196314-61-1 |
| Lithium tetrakis(pentafluorophenyl)borate etherate | Boulder Scientific, Boulder, CO BSC-353 | |
| Q-5 oxygen scavenger | Engelhard, Iselin, NJ 08830 | |
| Silver hexafluoroantimonate (98%) | Aldrich | 12005-82-2 |
| Silver hexafluorophosphate (99.99%) | Aldrich; Acros Organics, Belgium | 26042-63-7 |
| Sodium tetrakis[3,5-bis(trifluoromethyl)phenyl]borate(98+) | Aldrich | 79060-88-1 |
| Tricyclohexylphosphine (97%) | Strem | 2622-14-2 |

(a) Prepared according to the literature method of DiRenzo, G. M.; White, P. S.; Brookhart, M. J. Am. Chem. Soc. 1996, 118, 6225).;
(b) Prepared according to the literature method of Guzei, I. A., et al., S. F. Dalton Trans., 2003, 715–722.

General procedures. The polymerization reactions of Examples 2, 9, 11, 13, and 14 are carried out in a dry box under a nitrogen atmosphere. The polymerization reactions of Examples 1, 3–8, 10, and 12 are set up within a dry box under a nitrogen atmosphere. After the reaction is set up, the glass vessel is sealed, removed from the dry box, and heated using water bath in a fume hood.

Nitrogen is purified by passage through columns containing activated molecular sieves and Q-5 oxygen scavenger. Toluene is purified by passage through columns of activated molecular sieves (4 Å)/alumina/O2 remover (e.g., Q-5) and methylene chloride is purified by passage through columns of activated alumina. Lithium tetrakis(pentafluorophenyl) borate etherate is purchased from Boulder Scientific, allylpalladium chloride dimer (99%) and tricyclohexylphosphine (97%) are purchased from Strem, silver hexafluorophosphate (98%) is purchased from Acros, and all are used without further purification. Methyl acrylate (99%) is purchased from Aldrich and purified by passage through columns of MEHQ inhibitor remover and activated molecular sieves (4 Å), and purged with nitrogen for 0.5 hour. Norbornene (99%) is purchased from Acros and purified using one of the following two methods: 1) It is dried with calcium hydride at 60° C. overnight, degassed by freeze-pump-thaw twice and vacuum transferred at 50° C. to a dry glass receiver; 2) It is dissolved in a small amount of toluene to yield a clear colorless solution, which is passed through a column of activated molecular sieves (4 Å) and purged with nitrogen for 0.5 hour. The concentration of this toluene solution of norbornene is determined by $^1$H NMR analysis. Hexafluoroisopropanol norbornene and chlorobenzene are each sparged with nitrogen for 0.5 hours and then purified by passage over a column containing alumina and molecular sieves (3 Å).

Nuclear Magnetic Resonance (NMR) Spectroscopy. NMR spectra are recorded on Varian 600, Bruker DMX-400 or DRX-500 spectrometers at 23° C. unless otherwise indicated. 1H and 13C chemical shifts are reported vs. SiMe4 and are determined by reference to residual 1H and 13C solvent signals.

Molecular Weight Determination using Gel Permeation Chromatography (GPC). Gel Permeation Chromatography, otherwise known as size exclusion chromatography, actually separates the members of a distribution of polymer chains according to their hydrodynamic size in solution rather than their molar mass. The system is then calibrated with standards of known molecular weight and composition to correlate elution time with molecular weight. The techniques of GPC are discussed in detail in Modern Size Exclusion Chromatography, W. W. Yau, J. J Kirkland, D. D. Bly; Wiley-Interscience, 1979, and in A Guide to Materials Characterization and Chemical Analysis, J. P. Sibilia; VCH, 1988, p. 81–84.

All samples are prepared at concentration 2 mg/mL in THF or chloroform (HPLC grade) and gently stirred to dissolve the polymer sample completely. All polymer solutions are filtered using 1 μm PTFE filter. GPC separation are performed using 2 PL gel Mixed B columns and evaporative light scattering detector (ELSD). Typical chromatographic conditions: 2 PL gel MIXED B columns, particle size 5 μm; eluent: THF or CHCl3 (HPLC grade), 1.0 ml/min; injected volume of sample solution: 50 mL; PS standards with molecular weight ranging from 580 to 2 560 000 g/mol (0.5 mg/mL in THF or CHCl3) are used to construct calibration curve; ELS detection, (TN=40° C., TECH=80° C., Fnitrogen=1 L/min).

Liquid Chromatography—NMR. Typical LC-NMR experiment conditions: a sample is dissolved in CDCl$_3$ to form a solution (ca. 1%) and filtered through a 0.2 micron filter. The polymer separation is carried out on a SUPLECOSIL reverse-phase C-18 column (25 cm×4.6 mm), with a flow rate of 1 ml/min. The Evaporative Light Scattering detection (ELSD) and UV detectors are employed with a solvent gradient of acetonitrile/water/THF from 95/5/0 to 0/0/100 in 24 minutes. 1H LC-NMR spectra are acquired on a Varian UNITY INOVA 600 MHz NMR spectrometer.

Differential Scanning Calorimetry (DSC). Modulated Differential Scanning Calorimetry measurements are carried out on a Q-1000 Series DSC made by TA Instruments. Samples are run under an inert atmosphere of nitrogen at a flow rate of 25 mL/min. Samples are heated from −90° C. to +380° C. at a rate of 7° C./min with a modulation amplitude of 1° C. and a period of 40 s.

The following cationic metal-pair complexes are utilized in the examples:

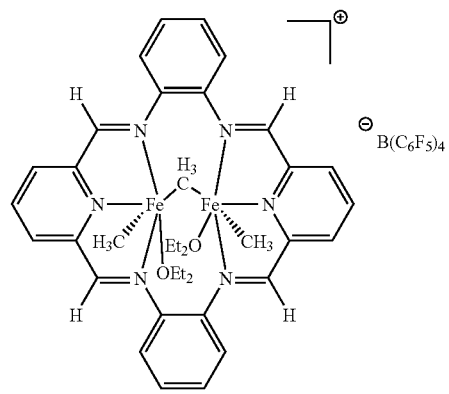

cationic metal-pair complex 1

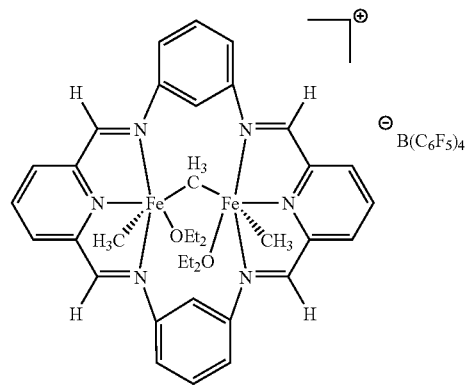

cationic metal-pair complex 2

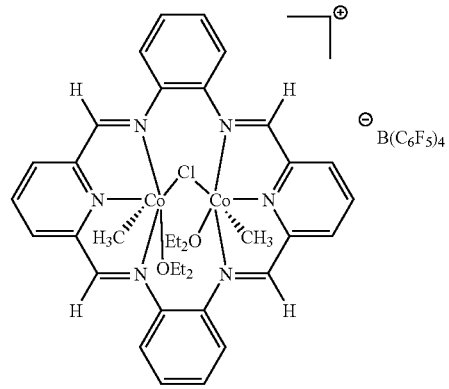

cationic metal-pair complex 3

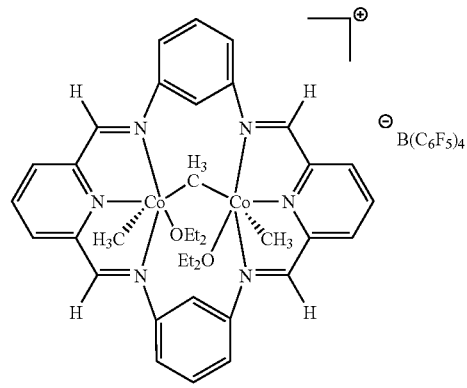

cationic metal-pair complex 4

-continued cationic metal-pair complex 5

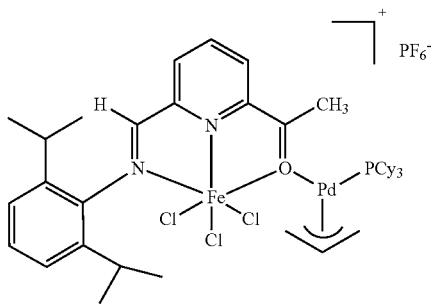

cationic metal-pair complex 6

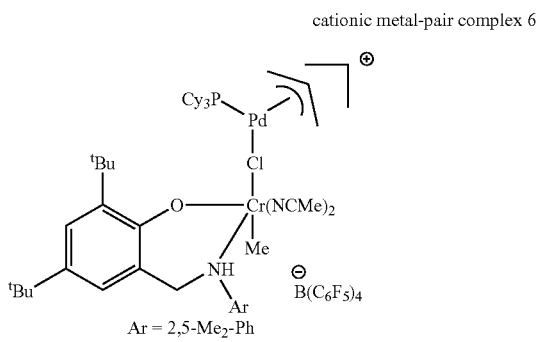

cationic metal-pair complex 7

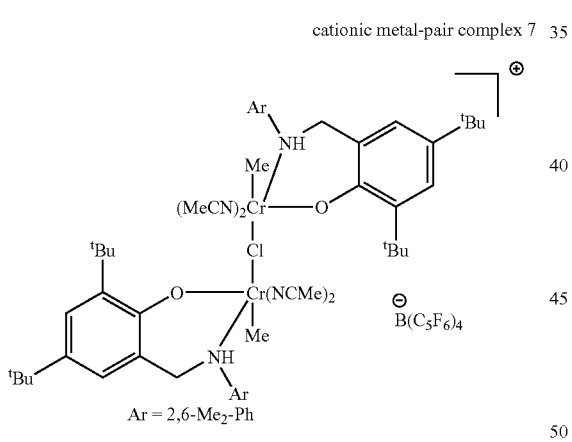

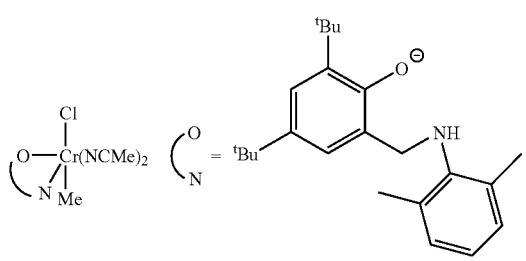

Precursor complex 1. (Source: Methylation of the (O^N)Cr (NCMe)$_2$Cl$_2$ precursor complex with Me$_4$Sn. Source of (O^N)Cr(NCMe)$_2$Cl$_2$: synthetic procedures published in Gibson, V. C.; Newton, C.; Redshaw, C.; Solan, G. A.; White, A. J. P.; Williams, D. J. J. Chem. Soc., Dalton Trans. 1999, 827.)

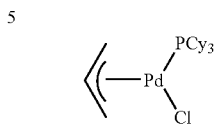

Precursor complex 2. (Reference: DiRenzo, G. M.; White, P. S.; Brookhart, M. J. Am. Chem. Soc. 1996, 118, 6225).

EXAMPLE A

Synthesis of Cationic Metal-Pair Complex 6. A 50 mL Schlenk is charged with precursor complex 2 (10 mmol). CH2Cl2 (20 mL) is added to form a clear pale yellow solution. A solution of thallium tetrakis(pentafluorophenyl) borate (10 mmol) in CH2Cl2 (20 mL) is added by syringe at 0° C. to form a pale yellow solution with a white precipitate. The reaction mixture is stirred at 0° C. for 15 min. A solution of precursor complex 1 (10 mmol) in CH2Cl2 (20 mL) is added by syringe at 0° C. to form a greenish-yellow solution. The reaction mixture is stirred at 0° C. for 20 min. The mixture is filtered to remove TlCl, and the product is dried under vacuum to afford a greenish-yellow solid, which is purified by crystallization in CH2Cl2 (2 mL) at −80° C. The experiment should afford a greenish-yellow solid (yield: 66%). NMR spectra should reveal that the product is Catalyst 6.

EXAMPLE B

Synthesis of Cationic Metal-Pair Complex 7. A 50 mL Schlenk is charged with Precursor complex 1 (10 mmol). CH2Cl2 (20 mL) is added to form a clear green solution. A solution of thallium tetrakis(pentafluorophenyl) borate (10 mmol) in CH2Cl2 (10 mL) is added by syringe at 0° C. to form a green solution with a white precipitate. The reaction mixture is stirred at 0° C. for 15 min. A solution of Precursor complex 1 (10 mmol) in CH2Cl2 (20 mL) is added by syringe at 0° C. to form a green solution. The reaction mixture is stirred at 0° C. for 20 min. The mixture is filtered to remove TlCl, and the product is dried under vacuum to afford a green solid, which is purified by crystallization in CH2Cl2 (2 mL) at −80° C. The experiment should afford a green solid (yield: 88%). NMR spectra should reveal that the product is Catalyst 7.

EXAMPLE 1

Utilizing a cationic metal-pair complex to prepare a homopolymer of norbornene, according to the method of the present invention. A 100 mL serum bottle is charged with toluene (20 mL) and norbornene (1.13 g, 12 mmol, pre-dissolved in toluene, 86 wt %) and sealed with a rubber septum. A solution of cationic metal-pair complex 1 (0.1 μmol) in CH2Cl2 (1 mL) is added by syringe at 50° C. The reaction mixture is stirred at 50° C. for 1 hour, which is then cooled to ambient temperature and quenched with methanol (50 mL) to yield an off-white slurry. The solid is isolated by filtration, washed with fresh methanol (3×15 mL) and dried under vacuum at 60° C. overnight, which should yield an off-white solid (0.95 g). NMR analysis should reveal that the product is polynorbornene. GPC analysis should reveal a unimodal pattern: Mw 1200000, Mn 1000000, Mw/Mn 1.2.

EXAMPLE 2

Utilizing a cationic metal-pair complex to prepare a homopolymer of ethylene, according to the method of the present invention. Toluene (3 mL) is charged to the glass liner of a steel pressure vessel (8 mL capacity) equipped with a mechanical stirrer. The pressure vessel is sealed and heated to 50° C. Ethylene pressure (350 psig) is introduced. Cationic metal-pair complex 1 (8 µmol in 0.25 mL of methylene chloride) is injected to the pressure vessel using an oven dried gas tight syringe. 0.75 mL of toluene is added via syringe to rinse the injection port. The polymerization is allowed to proceed under these reaction conditions for 2 h. After this time, the reactor is vented and the contents of the glass liner are added to methanol. After stirring overnight, the precipitated polymer is collected by vacuum filtration and washed with methanol. The polymer is dried in a vacuum oven heated to 60° C. overnight. The melting transitions measured by Differential Scanning Calorimetry (DSC) should be about 130° C. and the heat of fusion ($\Delta Hf$) should be greater than 100 J/g.

EXAMPLE 3

Utilizing a cationic metal-pair complex to prepare a homopolymer of methyl acrylate, according to the method of the present invention. A 100 mL serum bottle is charged with toluene (20 mL) and methyl acrylate (8.6 g, 0.1 mol) and sealed with a rubber septum. A solution of Cationic metal-pair complex 7 (10 µmol) in $CH_2Cl_2$ (1 mL) is added by syringe at 50° C. The reaction mixture is stirred at 50° C. for 4 hours and then cooled to ambient temperature and quenched with methanol (100 mL). The precipitated polymer is isolated by filtration, washed with fresh methanol (3×25 mL) and dried under vacuum at 65° C. overnight, which should yield a white solid (1.2 g). NMR analysis should reveal that the product is poly(methyl acrylate). GPC analysis should reveal a unimodal pattern: Mw 100000, Mn 58000, Mw/Mn 1.7.

EXAMPLE 4

Utilizing a cationic metal-pair complex to prepare a homopolymer of styrene, according to the method of the present invention. A 100 mL serum bottle is charged with toluene (20 mL) and styrene (10.4 g, 0.1 mol) and sealed with a rubber septum. A solution of Cationic metal-pair complex 2 (10 µmol) in $CH_2Cl_2$ (1 mL) is added by syringe at 50° C. The reaction mixture is stirred at 50° C. for 4 hours and then cooled to ambient temperature and quenched with methanol (100 mL). The precipitated polymer is isolated by filtration, washed with fresh methanol (3×25 mL) and dried under vacuum at 65° C. overnight, which should yield a white solid (5 g). NMR analysis should reveal that the product is polystyrene. GPC analysis should reveal a unimodal pattern: Mw 250000, Mn 125000, Mw/Mn 2.0.

EXAMPLE 5

Utilizing a cationic metal-pair complex to prepare a homopolymer of vinyl acetate, according to the method of the present invention. A 100 mL serum bottle is charged with toluene (20 mL) and vinyl acetate (8.6 g, 0.1 mol) and sealed with a rubber septum. A solution of Cationic metal-pair complex 2 (10 µmol) in $CH_2Cl_2$ (1 mL) is added by syringe at 50° C. The reaction mixture is stirred at 50° C. for 4 hours and then cooled to ambient temperature and quenched with methanol (100 mL). The precipitated polymer is isolated by filtration, washed with fresh methanol (3×25 mL) and dried under vacuum at 65° C. overnight, which should yield a white solid (2.0 g). NMR analysis should reveal that the product is poly(vinyl acetate). GPC analysis should reveal a unimodal pattern: Mw 170000, Mn 86000, Mw/Mn 2.0.

EXAMPLE 6

Utilizing a cationic metal-pair complex to prepare a homopolymer of vinyl chloride, according to the method of the present invention. A Fischer-Porter reactor, is charged with toluene (10 mL). Vinyl chloride (89 mmol, measured by a 800-mL glass bulb) is added by condensation at −196° C. The reactor is gradually warmed to −78° C. and Cationic metal-pair complex 3 (0.6 µmol) in $CH_2Cl_2$ (1 mL) is added by a syringe through a rubber septum. The reactor is sealed and gradually warmed to 55° C., at which temperature the reaction mixture is vigorously stirred. 6 hours later, the reactor is cooled to ambient temperature an excess pressure is released before the reaction mixture is poured into a beaker containing acidified methanol (1 v/v %, 250 mL) to yield a white slurry. The solid is collected by filtration, washed with fresh methanol (3×15 mL) and dried under vacuum at 60° C. for 18 hours, which should yield a white solid (4.8 g). NMR analysis should reveal that the product is poly(vinyl chloride). GPC analysis should reveal a unimodal pattern: Mw 220000, Mn 200000, Mw/Mn 1.1.

EXAMPLE 7

Utilizing a cationic metal-pair complex to prepare a homopolymer of methyl vinyl ether, according to the method of the present invention. A 100 mL serum bottle is charged with toluene (20 mL) and methyl vinyl ether (5.8 g, 0.1 mol, pre-dissolved in toluene, 74 wt %) and sealed with a rubber septum. A solution of Cationic metal-pair complex 4 (0.25 µmol) in $CH_2Cl_2$ (1 mL) is added by syringe at 50° C. The reaction mixture is stirred at 50° C. for 4 hours, which is then cooled to ambient temperature and quenched with methanol (100 mL) to yield a white slurry. The solid is isolated by filtration, washed with fresh methanol (3×25 mL) and dried under vacuum at 65° C. overnight, which should yield a white solid (5.1 g). NMR analysis should reveal that the product is poly(methyl vinyl ether). GPC analysis should reveal a unimodal pattern: Mw 140000, Mn 100000, Mw/Mn 1.4.

EXAMPLE 8

Utilizing a cationic metal-pair complex to prepare a copolymer of 5-R-norbornene (R=CH2C(CF3)2(OH)) and tert-butyl acrylate, according to the method of the present invention. The 100 mL serum bottle is charged with toluene (25 mL), 5-R-norbornene (13.7 g, 50 mmol), tert-butyl acrylate (6.4 g, 50 mmol), and sealed under N2 with a rubber septum. A solution of Cationic metal-pair complex 4 (0.15 µmol) in $CH_2Cl_2$ is added by syringe at 50° C. The reaction mixture is stirred at 50° C. 3.5 hours later, the reaction mixture is cooled to ambient temperature and quenched with hexane (250 mL) to form a white slurry immediately. The solid is isolated by filtration and all volatile species are removed under vacuum (0.5 mmHg) at 60° C. overnight.

The remaining solid is then re-dissolved in CHCl3 and the solution is passed through a column of ion exchange resin to remove catalyst residues. The purified solution is collected and CHCl3 is removed under vacuum at 50° C. overnight, which should yield a white powder (14.2 g). 13C NMR experiment should reveal that the product has a molar ratio of 55 (5-R-norbornene): 45 (tert-butyl acrylate). GPC analysis should reveal a unimodal pattern: Mw 25000, Mn 20000, Mw/Mn 1.25.

EXAMPLE 9

Utilizing a cationic metal-pair complex to prepare a copolymer of ethylene and methyl acrylate, according to the method of the present invention. Methyl acrylate (1 mL) and toluene (3 mL) are charged to the glass liner of a steel pressure vessel (8 mL capacity) equipped with a mechanical stirrer. The pressure vessel is sealed and heated to 50° C. Ethylene pressure (350 psig) is introduced. Cationic metal-pair complex 3 (8 µmol in 0.25 mL of methylene chloride) is injected to the pressure vessel using an oven dried gas tight syringe. 0.75 mL of toluene is added via syringe to rinse the injection port. The polymerization is allowed to proceed under these reaction conditions for 4 h. After this time, the reactor is vented and the contents of the glass liner are added to methanol. After stirring overnight, the precipitated polymer is collected by vacuum filtration and washed with methanol. The polymer is dried in a vacuum oven heated to 60° C. overnight. 1H NMR should reveal that the product is a copolymer with a molar ratio of 80 (ethylene): 20 (methyl acrylate). GPC analysis should reveal a unimodal pattern: Mw 80000, Mn 50500, Mw/Mn 1.6.

EXAMPLE 10

Utilizing a cationic metal-pair complex to prepare a copolymer of norbornene and methyl acrylate, according to the method of the present invention. A 100 mL serum bottle is charged with toluene (20 mL), norbornene (1.70 g, 18 mmol, pre-dissolved in toluene, 86 wt %), methyl acrylate (1.0 g, 12 mmol) and sealed with a rubber septum. A solution of Cationic metal-pair complex 5 (0.2 µmol) in CH$_2$Cl$_2$ is added by syringe at 50° C. The reaction mixture is vigorously stirred at 50° C. 5 hours later, the reaction mixture is cooled to ambient temperature and quenched with methanol (200 mL) to form a pale yellow slurry instantaneously. The solid is isolated by filtration, washed with fresh methanol (3×25 mL), and dried under vacuum at 60° C. overnight, which should yield a pale yellow solid (2.4 g). NMR analysis should reveal that the product has a molar ratio of 72 (norbornene): 28 (methyl acrylate). GPC analysis should reveal a unimodal pattern: Mw 60000, Mn 40000, Mw/Mn 1.25.

EXAMPLE 11

Utilizing a cationic metal-pair complex to prepare a copolymer of ethylene and norbornene, according to the method of the present invention. Norbornene (2 mL of a 79 wt % solution in toluene) and toluene (2 mL) are charged to the glass liner of a steel pressure vessel (8 mL capacity) equipped with a mechanical stirrer. The pressure vessel is sealed and heated to 50° C. Ethylene pressure (350 psig) is introduced. Cationic metal-pair complex 7 (8 µmol in 0.25 mL of methylene chloride) is injected to the pressure vessel using an oven dried gas tight syringe. 0.75 mL of toluene is added via syringe to rinse the injection port. The polymerization is allowed to proceed under these reaction conditions for 2 h. After this time, the reactor is vented and the contents of the glass liner are added to methanol. After stirring overnight, the precipitated polymer is collected by vacuum filtration and washed with methanol. The polymer is dried in a vacuum oven heated to 60° C. overnight. 1H NMR should reveal that the product is a copolymer with a molar ratio of 55 (ethylene): 45 (norbornene). GPC analysis should reveal a unimodal pattern: Mw 150000, Mn 80000, Mw/Mn 1.9.

EXAMPLE 12

Utilizing a catalytic cationic metal-pair complex to prepare a terpolymer of norbornene, 1-octene and methyl acrylate, according to the method of the present invention. A 100-mL serum bottle is charged with norbornene (12 mmol, pre-dissolved in toluene, 79 wt %), methyl acrylate (12 mmol), 1-octene (30 mmol) and toluene (20 mL), and sealed with a rubber septum. A solution of Cationic metal-pair complex 6 (0.34 µmol) in CH$_2$Cl$_2$ is added by syringe at 50° C. The reaction mixture is stirred at 50° C. 4 hours later, the reaction mixture is cooled to ambient temperature and methanol (250 mL). The solid is isolated by filtration, washed with fresh methanol (3×25 mL) and dried under vacuum at 70 deg C. overnight, which should yield a white solid (2.5 g). NMR analysis should reveal that the product has a molar ratio of 15 (norbornene): 30 (1-octene): 55 (methyl acrylate). GPC experiment should reveal a unimodal pattern: Mw 70000, Mn 43750, Mw/Mn 1.6.

EXAMPLE 13

Utilizing a cationic metal-pair complex to prepare a copolymer of ethylene and methyl methacrylate, according to the method of the present invention. Methyl methacrylate (1 mL) and toluene (2 mL) are charged to the glass liner of a steel pressure vessel (8 mL capacity) equipped with a mechanical stirrer. The pressure vessel is sealed and heated to 50° C. Ethylene pressure (350 psig) is introduced. Cationic metal-pair complex 5 (8 µmol in 0.25 mL of methylene chloride) is injected to the pressure vessel using an oven dried gas tight syringe. 0.75 mL of toluene is added via syringe to rinse the injection port. The polymerization is allowed to proceed under these reaction conditions for 1 h. After this time, the reactor is vented and the contents of the glass liner are added to methanol. After stirring overnight, the precipitated polymer is collected by vacuum filtration and washed with methanol. The polymer is dried in a vacuum oven heated to 60° C. overnight. 1H NMR should reveal that the product is a copolymer with a molar ratio of 90 (ethylene): 10 (methyl methacrylate). GPC analysis should reveal a unimodal pattern: Mw 25000, Mn 15000, Mw/Mn 1.7.

EXAMPLE 14

Utilizing a cationic metal-pair complex to prepare a copolymer of ethylene and styrene, according to the method of the present invention. Styrene (1 mL) and toluene (2 mL) are charged to the glass liner of a steel pressure vessel (8 mL capacity) equipped with a mechanical stirrer. The pressure vessel is sealed and heated to 50° C. Ethylene pressure (350 psig) is introduced. Cationic metal-pair complex 6 (8 µmol in 0.25 mL of methylene chloride) is injected to the pressure vessel using an oven dried gas tight syringe. 0.75 mL of toluene is added via syringe to rinse the injection port. The polymerization is allowed to proceed under these reaction conditions for 4 h. After this time, the reactor is vented and the contents of the glass liner are added to methanol. After stirring overnight, the precipitated polymer is collected by vacuum filtration and washed with methanol. The polymer is dried in a vacuum oven heated to 60° C. overnight. 1H NMR should reveal that the product is a copolymer with a molar ratio of 60 (ethylene): 40 (styrene). GPC analysis should reveal a unimodal pattern: Mw 95000, Mn 60000, Mw/Mn 1.6.

What is claimed is:

1. A catalytic composition comprising at least one cationic metal-pair complex, wherein:
   said cationic metal-pair complex comprises at least one metal atom pair, said pair comprising a first metal atom, $M^1$, and a second metal atom, $M^2$;
   said first metal atom and said second metal atom of said pair have a through-space internuclear distance of at least 1.5 Angstroms and no more than 20 Angstroms; and
   said cationic metal-pair complex is a complex according to formula I,

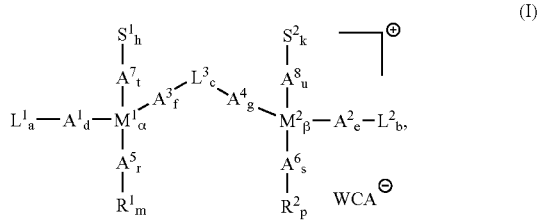
(I)

wherein:
$M^1$ represents a first metal atom selected from copper, iron, cobalt, ruthenium, rhodium, chromium, and manganese;
$L^1$ represents a set of first ligands;
$L^2$ represents a set of second ligands;
$L^3$ represents a set of third ligands;
$R^1$ represents a set of first anionic hydrocarbyl containing radicals;
$R^2$ represents a set of second anionic hydrocarbyl containing radicals;
$S^1$ represents a set of first labile ligands;
$S^2$ represents a set of second labile ligands;
$A^1-A^8$ each represent a set of coordination bonds;
WCA represents a weakly coordinating anion;
a, b, h, k, m, and p are each selected from 0 and 1;
$\alpha$, $\beta$, and c each equal 1;
d, r, and t are each selected from 0, 1, 2, 3, 4, and 5;
f is selected from 1, 2, 3, 4, 5, and 6;
$1 \leq m+p \leq 2$;
the sum d+f+r+t=6; and
sum e+g+s+u=4, 5, or 6; and
wherein:
when the sum e+g+s+u=4,
$M^2$ represents a second metal atom selected from nickel, palladium, copper, iron, cobalt, rhodium, chromium, and manganese;
e, s, and u are each selected from 0, 1, 2, and 3;
g is selected from 1, 2, 3, and 4;
$0 \leq d+e \leq 7$; $1 \leq r+s \leq 7$; $0 \leq t+u \leq 7$; and $2 \leq f+g \leq 9$;
or
when the sum e+g+s+u=6,
$M^2$ represents a second metal atom selected from copper, iron, cobalt, ruthenium, rhodium, chromium, and manganese;
e, s, and u are each selected from 0, 1, 2, 3, 4, and 5;
g is selected from 1, 2, 3, 4, 5, and 6;
$0 \leq d+e \leq 9$; $1 \leq r+s \leq 9$; $0 \leq t+u \leq 9$; and $2 \leq f+g \leq 11$.

2. The catalytic composition of claim 1, wherein said first metal atom and said second metal atom of said pair have a through-space internuclear distance of at least 2 Angstroms and no more than 10 Angstroms.

3. The catalytic composition of claim 1, wherein at least one of said first anionic hydrocarbyl containing radicals and said second anionic hydrocarbyl containing radicals is an addition polymer.

4. A method for preparing a catalytic composition, comprising:
   (i) providing a full-(metal pair) precursor complex according to said formula II

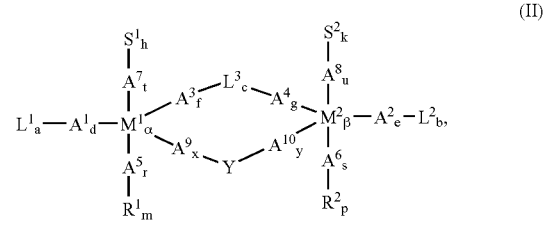
(II)

wherein:
$M^1$ represents a first metal atom selected from copper, iron, cobalt, ruthenium, rhodium, chromium, and manganese;
$L^1$ represents a set of first ligands;
$L^2$ represents a set of second ligands;
$L^3$ represents a set of third ligands;
$R^1$ represents a set of first anionic hydrocarbyl containing radicals;
$R^2$ represents a set of second anionic hydrocarbyl containing radicals;
$S^1$ represents a set of first labile ligands;
$S^2$ represents a set of second labile ligands;
$A^1-A^{10}$ each represents a set of coordination bonds;
Y represents a leaving group;
d+f+r+t+x=6; and
the sum e+g+s+u+y=4, or 6;

(ii) combining said full-(metal pair) precursor complex with at least one activator component;
(iii) removing said leaving group Y from said full-(metal pair) precursor complex; and
(iv) replacing said leaving group Y with at least one replacement moiety;
wherein for said full-(metal pair) precursor complex
$\alpha$, $\beta$, and c each equal 1;
a, b, h, k, m, p, x, and y are each selected from 0 and 1;
d, r, and t are each selected from 0, 1, 2, 3, 4, and 5;
f is selected from 1, 2, 3, 4, 5, and 6;
$1 \leq m+p \leq 2$; and
$1 \leq x+y \leq 2$;

wherein:
when the sum e+g+s+u+y=4,
M² represents a second metal atom selected from nickel, palladium, copper, iron, cobalt, rhodium, chromium, and manganese;
e, s, and u are selected from 0, 1, 2, and 3;
g is selected from 1, 2, 3, and 4;
0≦d+e≦6; 1≦r+s≦7; 0≦t+u≦6; and 2≦f+g≦8; or
when the sum e+g+s+u+y=6,
M² represents a second metal atom selected from copper, iron, cobalt, ruthenium, rhodium, chromium, and manganese;
e, s, and u are each selected from 0, 1, 2, 3, 4, and 5;
g is selected from 1, 2, 3, 4, 5, and 6;
0≦d+e≦8; 1≦r+s≦9; 0≦t+u≦8; and 2≦f+g≦10.

5. A method for preparing a catalytic composition, comprising:
(i) providing a first semi-(metal pair) precursor complex and a second semi-(metal pair) precursor complex both according to formula II

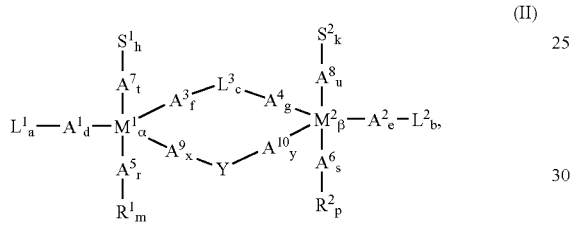

wherein:
M¹ represents a first metal atom selected from copper, iron, cobalt, ruthernium, rhodium, chromium, and manganese;
L¹ represents a set of first ligands;
L² represents a set of second ligands;
L³ represents a set of third ligands;
R¹ represents a set of first anionic hydrocarbyl containing radicals;
R² represents a set of second anionic hydrocarbyl containing radicals;
S¹ represents a set of first labile ligands;
S² represents a set of second labile ligands;
A¹–A¹⁰ each represents a set of coordination bonds;
Y represents a leaving group;
(ii) combining said first semi-(metal pair) precursor complex with at least one activator component;
(iii) removing said leaving group Y from said first semi-(metal pair) precursor complex; and
(iv) replacing said leaving group Y with said second semi-(metal pair) precursor complex;
wherein for said first semi-(metal pair) precursor complex
α and x each equal 1;
β, b, c, k, p, e, f, g, s, u, and y each equal 0;
a, h, and m are each selected from 0 and 1;
d, r, and t are each selected from 0, 1, 2, 3, 4, and 5; and the sum d+f+r+t+x=6; and
wherein for said second semi-(metal pair) precursor complex
β equals 1;
α, a, c, h, m, d, f, g, r, t, x, and y each equal 0;
b, k, and p are each selected from 0 and 1; and the sum e+g+s+u+y=4, or 6; and wherein:
when the sum e+g+s+U+y=4,
M² represents a second metal atom selected from nickel, palladium, copper, iron, cobalt, rhodium, chromium, and manganese;
e is selected from 0, 1, 2, 3, and 4; and
s and u are each selected from 0, 1, 2, and 3; or
when the sum e+g+s+u+y=6
M² represents a second metal atom selected from copper, iron, cobalt, ruthenium, rhodium, chromium, and manganese;
e is selected from 0, 1, 2, 3, 4, 5, and 6; and
s and u are each selected from 0, 1, 2, 3, 4, and 5; and
wherein the sum of m of said first semi-(metal pair) precursor complex+p of said second semi-(metal pair) precursor complex is selected from 1 or 2.

6. A method for preparing a catalytic composition, comprising:
(i) providing a first semi-(metal pair) precursor complex and a second semi-(metal pair) precursor complex both according to formula II

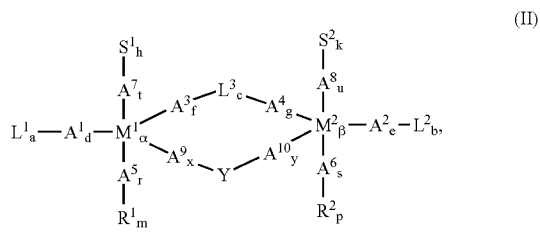

wherein:
M¹ represents a first metal atom selected from copper, iron, cobalt, ruthenium, rhodium, chromium, and manganese;
L¹ represents a set of first ligands;
L² represents a set of second ligands;
L³ represents a set of third ligands;
R¹ represents a set of first anionic hydrocarbyl containing radicals;
R² represents a set of second anionic hydrocarbyl containing radicals;
S¹ represents a set of first labile ligands;
S² represents a set of second labile ligands;
A¹–A¹⁰ each represents a set of coordination bonds;
Y represents a leaving group;
(ii) combining said first semi-(metal pair) precursor complex with at least one activator component;
(iii) removing said leaving group Y from said first semi-(metal pair) precursor complex; and
(iv) replacing said leaving group Y with said second semi-(metal pair) precursor complex;
wherein for said first semi-(metal pair) precursor complex
β and y each equal 1;
α, a, c, h, m, d, f, g, r, t, and x each equal 0;
b, k, and p are each selected from 0 and 1; and the sum e+g+s+u+y=4, or 6; and
wherein:
when the sum e+g+s+u+y=4,
M² represents a second metal atom selected from nickel, palladium, copper, iron, cobalt, rhodium, chromium, and manganese; and
e, s and u are each selected from 0, 1, 2, and 3;

when the sum $e+g+s+U+y=6$ $M^2$ represents a second metal atom selected from copper, iron, cobalt, ruthenium, rhodium, chromium, and manganese; and e, s and u are each selected from 0, 1, 2, 3, 4, and 5; and wherein for said second semi-(metal pair) precursor complex α equals 1;

β, b, c, k, p, e, f, g, s, u, x, and y each equal 0;

a, h, and m are each selected from 0 and 1;

d is selected from 0, 1, 2, 3, 4, 5, and 6;

r and t are each selected from 0, 1, 2, 3, 4, and 5; and the sum $d+f+r+t+x=6$; and wherein the sum of m of said first semi-(metal pair) precursor complex+p of said second semi-(metal pair) precursor complex is selected from 1 or 2.

7. A method for preparing at least one addition polymer comprising:

(a) combining:

(i) a catalytic composition according to claim 1; and (ii) at least one ethylenically unsaturated monomer; and (b) polymerizing said at least one ethylenically unsaturated monomer in the presence of said catalytic composition to form said addition polymer.

8. The method of claim 7, wherein said at least one addition polymer is selected from poly[(polar olefin)-(non-polar olefin)], poly(polar olefin), poly(non-polar olefin), and combinations thereof, wherein said at least one said ethylenically unsaturated monomer is selected from at least one polar olefinic monomer, at least one non-polar olefinic monomer, and combinations thereof.

9. The method of claim 8, wherein said poly[(polar olefin)-(non-polar olefin)] has a combined molar percentage of polar olefinic monomers and non-polar olefinic monomers present, as polymerized units, of at least 70 mole-% to 100 mole-%, based upon the total moles of all polar olefinic monomers and non-polar olefinic monomers present, as polymerized units, in said at least one addition polymer.

10. The method of claim 7, wherein said addition polymer comprises, as polymerized units, at least one (meth)acrylate monomer, wherein said (meth)acrylate monomers have a molar ratio to all said ethylenically unsaturated monomers, present as polymerized units, of at least 0.05:99.95 to 100:0.

11. The method of claim 7, wherein said addition polymer comprises, as polymerized units, at least one cyclic olefin monomer, wherein said cyclic olefin monomers have a molar ratio to all said ethylenically unsaturated monomers, present as polymerized units, of at least 0.05:99.95 to 100:0.

* * * * *